(12) United States Patent
Krieg et al.

(10) Patent No.: US 7,517,861 B2
(45) Date of Patent: Apr. 14, 2009

(54) IMMUNOSTIMULATORY NUCLEIC ACID MOLECULES

(75) Inventors: Arthur M. Krieg, Wellesley, MA (US); Joel N. Kline, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 195 days.

(21) Appl. No.: 10/888,785

(22) Filed: Jul. 9, 2004

(65) Prior Publication Data

US 2005/0032736 A1 Feb. 10, 2005

Related U.S. Application Data

(60) Continuation of application No. 09/818,918, filed on Mar. 27, 2001, now abandoned, which is a division of application No. 08/738,652, filed on Oct. 30, 1996, now Pat. No. 6,207,646, which is a continuation-in-part of application No. 08/386,063, filed on Feb. 7, 1995, now Pat. No. 6,194,388, which is a continuation-in-part of application No. 08/276,358, filed on Jul. 15, 1994, now abandoned.

(51) Int. Cl.
*A61K 39/00* (2006.01)
*A61K 39/38* (2006.01)
*A61K 45/00* (2006.01)
*A61K 47/00* (2006.01)
*A61K 9/127* (2006.01)
*A61K 9/52* (2006.01)
*A61K 9/16* (2006.01)
*A61K 9/50* (2006.01)
*A61K 31/70* (2006.01)
*A01N 25/08* (2006.01)
*A01N 43/04* (2006.01)
*A61F 13/00* (2006.01)

(52) U.S. Cl. .................. 514/44; 424/184.1; 424/282.1; 424/278.1; 424/409; 424/434; 424/450; 424/457; 424/490

(58) Field of Classification Search .............. 424/184.1, 424/278.1, 282.1, 409, 434, 450, 457, 490; 514/44
See application file for complete search history.

(56) References Cited

U.S. PATENT DOCUMENTS

| | | | |
|---|---|---|---|
| 4,452,775 A | 6/1984 | Kent | |
| 5,023,243 A | 6/1991 | Tullis | |
| 5,112,605 A | 5/1992 | Jardieu et al. | |
| 5,178,860 A | 1/1993 | MacKenzie et al. | |
| 5,498,410 A | 3/1996 | Gleich | |
| 5,595,756 A | 1/1997 | Bally et al. | |
| 5,663,153 A | 9/1997 | Hutcherson et al. | |
| 5,679,647 A | 10/1997 | Carson et al. | |
| 5,681,555 A | 10/1997 | Gleich | |
| 5,723,335 A | 3/1998 | Hutcherson et al. | |
| 5,726,160 A | 3/1998 | McMichael | |
| 5,753,613 A | 5/1998 | Ansell et al. | |
| 5,780,448 A | 7/1998 | Davis | |
| 5,804,566 A | 9/1998 | Carson et al. | |
| 5,849,719 A | 12/1998 | Carson et al. | |
| 5,908,620 A | 6/1999 | Tu et al. | |
| 5,955,059 A | 9/1999 | Gilchrest et al. | |
| 5,955,442 A | 9/1999 | McMichael | |
| 5,968,909 A | 10/1999 | Agrawal et al. | |
| 5,994,315 A | 11/1999 | Nyce et al. | |
| 6,025,339 A | 2/2000 | Nyce et al. | |
| 6,040,296 A | 3/2000 | Nyce et al. | |
| 6,086,898 A * | 7/2000 | DeKruyff et al. | ........ 424/275.1 |
| 6,090,791 A | 7/2000 | Sato et al. | |
| 6,096,721 A | 8/2000 | McMichael | |
| 6,100,244 A | 8/2000 | McMichael | |
| 6,107,062 A | 8/2000 | Hu et al. | |
| 6,110,745 A | 8/2000 | Zhang et al. | |
| 6,174,872 B1 | 1/2001 | Carson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,221,882 B1 | 4/2001 | Macfarlane | |
| 6,239,116 B1 | 5/2001 | Krieg et al. | |
| 6,339,068 B1 | 1/2002 | Krieg et al. | |
| 6,348,312 B1 | 2/2002 | Peyman et al. | |
| 6,399,630 B1 | 6/2002 | Macfarlane | |
| 6,406,705 B1 | 6/2002 | Davis et al. | |

(Continued)

FOREIGN PATENT DOCUMENTS

EP 0 468 520 A2 1/1992

(Continued)

OTHER PUBLICATIONS

National Institute of Health, Publication No. 97-4051, Jul. 1997.

(Continued)

*Primary Examiner*—N. M Minnifield
(74) *Attorney, Agent, or Firm*—Wolf, Greenfield & Sacks P.C.; Gregg C. Benson

(57) ABSTRACT

Nucleic acids containing unmethylated CpG dinucleotides and therapeutic utilities based on their ability to stimulate an immune response and to redirect a Th2 response to a Th1 response in a subject are disclosed. Methods for treating atopic diseases, including atopic dermatitis, are disclosed.

12 Claims, 19 Drawing Sheets

U.S. PATENT DOCUMENTS

| | | |
|---|---|---|
| 6,426,336 B1 | 7/2002 | Carson et al. |
| 6,429,199 B1 | 8/2002 | Krieg et al. |
| 6,479,504 B1 | 11/2002 | Macfarlane et al. |
| 6,498,148 B1 | 12/2002 | Raz |
| 6,514,948 B1 | 2/2003 | Raz et al. |
| 6,521,637 B2 | 2/2003 | Macfarlane |
| 6,552,006 B2 | 4/2003 | Raz et al. |
| 6,610,661 B1 | 8/2003 | Carson et al. |
| 6,620,805 B1 | 9/2003 | Takle et al. |
| 6,653,292 B1 | 11/2003 | Krieg et al. |
| 6,693,086 B1 | 2/2004 | Dow et al. |
| 6,727,230 B1 | 4/2004 | Hutcherson et al. |
| 6,787,524 B2 | 9/2004 | Chang et al. |
| 6,821,957 B2 | 11/2004 | Krieg et al. |
| 6,943,240 B2 | 9/2005 | Bauer et al. |
| 6,949,520 B1 | 9/2005 | Hartmann et al. |
| 6,951,845 B2 | 10/2005 | Carson et al. |
| 7,001,890 B1 | 2/2006 | Wagner et al. |
| 7,129,222 B2 * | 10/2006 | Van Nest et al. ............... 514/44 |
| 7,183,111 B2 * | 2/2007 | Van Nest et al. ............... 514/44 |
| 7,214,380 B1 * | 5/2007 | DeKruyff et al. ......... 424/275.1 |
| 7,223,741 B2 | 5/2007 | Krieg |
| 7,250,403 B2 * | 7/2007 | Van Nest et al. ............... 514/44 |
| 7,271,156 B2 | 9/2007 | Krieg et al. |
| 7,354,909 B2 * | 4/2008 | Klinman et al. ................ 514/44 |
| 7,402,572 B2 * | 7/2008 | Krieg et al. .................... 514/44 |
| 2001/0044416 A1 | 11/2001 | McCluskie et al. |
| 2001/0046967 A1 | 11/2001 | Van Nest et al. |
| 2002/0055477 A1 | 5/2002 | Van Nest et al. |
| 2002/0091097 A1 | 7/2002 | Bratzler et al. |
| 2002/0102255 A1 | 8/2002 | Chang |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0022852 A1 | 1/2003 | Van Nest et al. |
| 2003/0026782 A1 | 2/2003 | Krieg |
| 2003/0026801 A1 | 2/2003 | Weiner et al. |
| 2003/0027782 A1 | 2/2003 | Carson et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0059773 A1 | 3/2003 | Van Nest et al. |
| 2003/0064064 A1 | 4/2003 | Dina et al. |
| 2003/0078223 A1 | 4/2003 | Raz et al. |
| 2003/0091599 A1 | 5/2003 | Davis et al. |
| 2003/0092663 A1 | 5/2003 | Raz et al. |
| 2003/0100527 A1 | 5/2003 | Krieg et al. |
| 2003/0119773 A1 | 6/2003 | Raz et al. |
| 2003/0119774 A1 | 6/2003 | Foldvari et al. |
| 2003/0129251 A1 * | 7/2003 | Van Nest et al. ............ 424/493 |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0191079 A1 | 10/2003 | Krieg et al. |
| 2003/0212026 A1 | 11/2003 | Krieg et al. |
| 2003/0212028 A1 | 11/2003 | Raz et al. |
| 2003/0224010 A1 | 12/2003 | Davis et al. |
| 2003/0232074 A1 | 12/2003 | Lipford et al. |
| 2003/0232780 A1 | 12/2003 | Carson et al. |
| 2003/0232856 A1 | 12/2003 | Macfarlane |
| 2004/0006010 A1 | 1/2004 | Carson et al. |
| 2004/0009942 A1 | 1/2004 | Van Nest et al. |
| 2004/0009949 A1 | 1/2004 | Krieg |
| 2004/0030118 A1 | 2/2004 | Wagner et al. |
| 2004/0053880 A1 | 3/2004 | Krieg |
| 2004/0064064 A1 | 4/2004 | Zhou et al. |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Kreig et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0209184 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |

| | | |
|---|---|---|
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Kreig et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0113929 A1* | 5/2008 | Lipford et al. ............ 514/44 |
| 2008/0124366 A1* | 5/2008 | Ohlfest et al. ............ 424/278.1 |
| 2008/0131464 A1* | 6/2008 | Cohen et al. ............ 424/272.1 |
| 2008/0145375 A1* | 6/2008 | Bembridge et al. ...... 424/184.1 |
| 2008/0146488 A1* | 6/2008 | Wettstein et al. ............ 514/2 |
| 2008/0152662 A1* | 6/2008 | Agrawal et al. .......... 424/184.1 |
| 2008/0171716 A1* | 7/2008 | MacLachlan et al. ......... 514/44 |

FOREIGN PATENT DOCUMENTS

| | | |
|---|---|---|
| WO | WO 91/12811 A1 | 9/1991 |
| WO | WO 92/03456 A1 | 3/1992 |
| WO | WO 94/19945 A1 | 9/1994 |
| WO | WO 96/32138 A1 | 10/1996 |
| WO | WO 96/40162 A1 | 12/1996 |
| WO | WO 99/56755 A1 | 11/1999 |
| WO | WO 00/06588 A1 | 2/2000 |
| WO | WO 00/14217 A2 | 3/2000 |
| WO | WO 00/67023 A1 | 11/2000 |
| WO | WO 02/052002 A2 * | 7/2002 |
| WO | WO 03/014316 A2 * | 2/2003 |
| WO | WO 03/068169 A2 | 8/2003 |
| WO | WO 03/368169 A2 * | 8/2003 |
| WO | WO 2004/007743 A2 | 1/2004 |
| WO | WO 2004/026888 A2 | 4/2004 |
| WO | WO 2004/094671 A2 | 11/2004 |
| WO | WO 2006/080946 A2 | 8/2006 |
| WO | WO 2007/031877 A2 | 3/2007 |
| WO | WO 2007/038720 A2 | 4/2007 |

OTHER PUBLICATIONS

Agrawal et al., Pharmacokinetics of oligonucleotides. Ciba Found Symp. 1997;209:60-75; discussion 75-8.
Agrawal et al., Absorption, tissue distribution and in vivo stability in rats of a hybrid antisense oligonucleotide following oral administration. Biochem Pharmacol. 1995 Aug. 8;50(4):571-6.
Agrawal et al., Pharmacokinetics, biodistribution, and stability of oligodeoxynucleotide phosphorothioates in mice. Proc Natl Acad Sci U S A. Sep. 1, 1991;88(17):7595-9.
Agrawal et al., Pharmacokinetics of antisense oligonucleotides. Clin Pharmacokinet. Jan. 1995;28(1):7-16.
Agrawal et al., Antisense oligonucleotides: towards clinical trials. Trends in Biotechnology, 1996; 14: 376-87.
Alpar et al., Potential of particulate carriers for the mucosal delivery of DNA vaccines. Biochem Soc Trans. May 1997;25(2):337S.
Anderson et al., TH2 and 'TH2-like' cells in allergy and asthma: pharmacological perspectives. Trends Pharmacol Sci. Sep. 1994;15(9):324-32.
Anitescu et al., Interleukin-10 functions in vitro and in vivo to inhibit bacterial DNA-induced secretion of interleukin-12. J Interferon Cytokine Res. Dec. 1997;17(12):781-8.
Ballas et al., Induction of NK activity in murine and human cells by CpG motifs in oligodeoxynucleotides and bacterial DNA. J Immunol. Sep. 1, 1996;157(5):1840-5.
Boggs et al., Characterization and modulation of immune stimulation by modified oligonucleotides. Antisense Nucleic Acid Drug Dev. Oct. 1997;7(5):461-71.
Bowersock et al., Evaluation of an orally administered vaccine, using hydrogels containing bacterial exotoxins of *Pasteurella haemolytica*, in cattle. Am J Vet Res. Apr. 1994;55(4):502-9.
Branda et al., Immune stimulation by an antisense oligomer complementary to the rev gene of HIV-1. Biochem Pharmacol. May 25, 1993;45(10):2037-43.
Branda et al., Amplification of antibody production by phosphorothioate oligodeoxynucleotides. J Lab Clin Med. Sep. 1996;128(3):329-38.
Carson et al., Oligonucleotide adjuvants for T helper 1 (TH1)-specific vaccination. J Exp Med. Nov. 17, 1997;186(10):1621-2.
Chace et al., Bacterial DNA-induced NK cell IFN-gamma production is dependent on macrophage secretion of IL-12. Clin Immunol Immunopathol. Aug. 1997;84(2):185-93.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chu et al., CpG oligodeoxynucleotides act as adjuvants that switch on T helper I (Th1) immunity. J Exp Med. Nov. 17, 1997;186(10):1623-31.
Cohen, Selective anti-gene therapy for cancer: principles and prospects. Tohoku J Exp Med. Oct. 1992;168(2):351-9.
Cossum et al., Disposition of the 14C-labeled phosphorothioate oligonucleotide ISIS 2105 after intravenous administration to rats. J Pharmacol Exp Ther. Dec. 1993;267(3):1181-90.
Cowdery et al., Bacterial DNA induces NK cells to produce IFN-gamma in vivo and increases the toxicity of lipopolysaccharides. J Immunol. Jun. 15, 1996; 156(12):4570-5.
Cowsert et al., In vitro evaluation of phosphorothioate oligonucleotides targeted to the E2 mRNA of papillomavirus: potential treatment for genital warts. Antimicrob Agents Chemother. Feb. 1993;37(2):171-7.
Crooke et al., Phosphorothioate Oligonucleotides. Therapeut Apps. 1995;ch5:63-84.
Cryz et al., European Commission COST/STD Initiative. Report of the expert panel VII. Vaccine delivery systems. Vaccine. May 1996;14(7):665-90.
Davis et al., Plasmid DNA expression systems for the purpose of immunization. Curr Opin Biotechnol. Oct. 1997;8(5):635-46.
Delong et al., Characterization of complexes of oligonucleotides with polyamidoamine starburst dendrimers and effects on intracellular delivery. J Pharm Sci. Jun. 1997;86(6):762-4. Abstract Only.
Durham et al., Immunotherapy and allergic inflammation. Clin Exp Allergy. Jan. 1991;21 Suppl 1:206-10.
Eldridge et al., Biodegradable microspheres as a vaccine delivery system. Mol Immunol. Mar. 1991;28(3):287-94. Abstract Only.
Emi et al., Gene transfer mediated by polyarginine requires a formation of big carrier-complex of DNA aggregate. Biochem Biophys Res Commun. Feb. 13, 1997;231(2):421-4.
Etchart et al., Class I-restricted CTL induction by mucosal immunization with naked DNA encoding measles virus haemagglutinin. J Gen Virol. Jul. 1997;78 ( Pt 7):1577-80.
Fields et al., Fields' Virology. 2001;1:1153.

Fraley et al., New generation liposomes: the engineering of an efficient vehicle for intracellular delivery of nucleic acids. Trends Biochem Sci. 1981;6:77-80.

Gallichan et al., Specific secretory immune responses in the female genital tract following intranasal immunization with a recombinant adenovirus expressing glycoprotein B of herpes simplex virus. Vaccine. Nov. 1995;13(16);1589-95.

Garegg et al., Nucleoside H-phosphonates. IV. Automated solid phase synthesis of oligoribonucleotides by the hydrogenphosphonate approach. Tetrahedron Lett. 1986;27(34):4055-8.

Geissler et al., Enhancement of cellular and humoral immune responses to hepatitis C virus core protein using DNA-based vaccines augmented with cytokine-expressing plasmids. J Immunol. Feb. 1, 1997;158(3):1231-7.

Goodman et al., Selective modulation of elements of the immune system by low molecular weight nucleosides. J Pharmacol Exp Ther. Sep. 1995;274(3):1552-7.

Gregoriadis et al., Liposomes for drugs and vaccines. Trends Biotechnol. 1985;3:235-41.

Gregoriadis et al., Engineering liposomes for drug delivery: progress and problems. Trends Biotechnol. Dec. 1995;13(12):527-37.

Hadden et al., Immunostimulants. Trends Pharmacol Sci. May 1993;14(5):169-74.

Hahm et al., Efficacy of polyadenylic.polyuridylic acid in the treatment of chronic active hepatitis B. Int J Immunopharmacol. Mar. 1994;16(3):217-25.

Halpern et al., Bacterial DNA induces murine interferon-gamma production by stimulation of interleukin-12 and tumor necrosis factor-alpha. Cell Immunol. Jan. 10, 1996;167(1):72-8.

Haneberg et al., Induction of specific immunoglobulin A in the small intestine, colon-rectum, and vagina measured by a new method for collection of secretions from local mucosal surfaces. Infect Immun. Jan. 1994;62(1):15-23.

Harrington et al., Adjuvant effects of low doses of a nuclease-resistant derivative of polyinosinic acid . polycytidylic acid on antibody responses of monkeys to inactivated Venezuelan equine encephalomyelitis virus vaccine. Infect Immun. Apr. 1979;24(1):160-6.

Haynes et al., Particle-mediated nucleic acid immunization. J Biotechnol. Jan. 26, 1996;44(1-3):37-42.

Hinkula et al., Recognition of prominent viral epitopes induced by immunization with human immunodeficiency virus type 1 regulatory genes. J Virol. Jul. 1997;71(7):5528-39.

Hogg, The pathology of asthma. APMIS. Oct. 1997;105(10):735-45.

Holmgren et al., Cholera toxin and cholera B subunit as oral-mucosal adjuvant and antigen vector systems. Vaccine. Sep. 1993;11(12):1179-84.

Hornquist et al., Cholera toxin adjuvant greatly promotes antigen priming of T cells. Eur J Immunol. Sep. 1993;23(9):2136-43.

Hudson et al., Nucleic acid dendrimers: Novel biopolymer structures. J Am Chem Soc. 1993;115:2119-24.

Hussain et al., CpG oligodeoxynucleotides: a novel therapeutic approach for atopic disorders. Curr Drug Targets Inflamm Allergy. Sep. 2003;2(3):199-205.

Hussain et al., DNA, the immune system, and atopic disease. J Investig Dermatol Symp Proc. Jan. 2004;9(1):23-8.

Ikeda et al., Microbial DNA and Host Immunity. Chapter 23: Immunostimulatory DNA for allergic asthma. 2002: 289-99.

Iversen et al., In vivo studies with phosphorothioate oligonucleotides: pharmacokinetics prologue. Anticancer Drug Des. Dec. 1991;6(6):531-8.

Iversen et al., Pharmacokinetics of an antisense phosphorothioate oligodeoxynucleotide against rev from human immunodeficiency virus type 1 in the adult male rat following single injections and continuous infusion. Antisense Res Dev. 1994 Spring;4(1):43-52.

Jain et al., Mucosal immunotherapy with CpG oligodeoxynucleotides reverses a murine model of chronic asthma induced by repeated antigen exposure. Am J Physiol Lung Cell Mol Physiol. Nov. 2003;285(5):L1137-46.

Jain et al., CpG DNA and immunotherapy of allergic airway diseases. Clin Exp Allergy. Oct. 2003;33(10):1330-5.

Jain et al., CpG DNA: immunomodulation and remodelling of the asthmatic airway. Expert Opin Biol Ther. Sep. 2004;4(9):1533-40.

Jain et al., CpG-oligodeoxynucleotides inhibit airway remodeling in a murine model of chronic asthma. J Allergy Clin Immunol. Dec. 2002;110(6):867-72.

Jain et al., The promise of CpG DNA in the treatment of asthma. Recent Res Develop Resp Crit Care Med. 2002;2:7-18.

Jäschke et al., Automated incorporation of polyethylane glycol into synthetic oligonucleotides. Tetrahedron Lett. 1993;34(2):301-4.

Johnson et al., Non-specific resistance against microbial infections induced by polyribonucleotide complexes. In: Immunopharmacology of infection diseases: Vaccine adjuvants and modulators of non-specific resistance. 1987: 291-301.

Jones et al., Poly(DL-lactide-co-glycolide)-encapsulated plasmid DNA elicits systemic and mucosal antibody responses to encoded protein after oral administration. Vaccine. Jun. 1997;15(8):814-7.

Kataoka et al., Antitumor activity of synthetic oligonucleotides with sequences from cDNA encoding proteins of Mycobacterium bovis BCG. Jpn J Cancer Res. Mar. 1992;83(3):244-7.

Kataoka et al., Immunotherapeutic potential in guinea-pig tumor model of deoxyribonucleic acid from Mycobacterium bovis BCG complexed with poly-L-lysine and carboxymethylcellulose. Jpn J Med Sci Biol. Oct. 1990;43(5):171-82.

Kimura et al., Binding of oligoguanylate to scavenger receptors is required for oligonucleotides to augment NK cell activity and induce IFN. J Biochem (Tokyo). Nov. 1994;116(5):991-4.

Kline et al., Modulation of airway inflammation by CpG oligodeoxynucleotides in a murine model of asthma. J Immunol. Mar. 15, 1998;160(6):2555-9.

Kline et al., Induction of oral tolerance by CpG-ODNs in a murine model of asthma. J Allergy Clin Immunol. Feb. 2004;113(2):S254. Abstract 915.

Kline et al., Treatment of established asthma in a murine model using CpG oligodeoxynucleotides. Am J Physiol Lung Cell Mol Physiol. Jul. 2002;283(1):L170-9.

Kline et al., DNA therapy for asthma. Curr Opin Allergy Clin Immunol. Feb. 2002;2(1):69-73.

Kline et al., The American Federation for Clinical Research, Midwestern section and Eastern section annual meeting. 1996. Abstracts. J Investig Med. Sep. 1996;44(7): 380A.

Kline et al., Biomedicine '97. Medical research from bench to bedside. Washington, D.C., Apr. 25-27, 1997. Abstracts. J Investig Med. Mar. 1997;45(3): 282A.

Kline et al., American Federation for Medical Research Midwestern Regional Meeting. Chicago, Illinois, Sep. 25-27, 1997. Abstracts. J Investig Med. Sep. 1997;45(7): 298A.

Kline et al., CpG oligodeoxynucleotides do not require TH1 cytokines to prevent eosinophilic airway inflammation in a murine model of asthma. J Allergy Clin Immunol. Dec. 1999;104(6):1258-64.

Klinman et al., Contribution of CpG motifs to the immunogenicity of DNA vaccines. J Immunol. Apr. 15, 1997;158(8):3635-9.

Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.

Kou et al., [Analysis and regulation of interferon-gamma production by peripheral blood lymphocytes from patients with bronchial asthma] Arerugi. Mar. 1994;43(3):482-91. Japanese. Abstract Only.

Krieg et al., Lymphocyte activation mediated by oligodeoxynucleotides or DNA containig novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).

Krieg et al., Oligodeoxynucleotide modifications determine the magnitude of B cell stimulation by CpG motifs. Antisense Nucleic Acid Drug Dev. 1996 Summer;6(2):133-9.

Krieg et al., Phosphorothioate oligodeoxynucleotides: antisense or anti-protein? Antisense Res Dev. 1994 Winter;5(4):241.

Krieg et al., Leukocyte stimulation by oligodeoxynucleotides. In: Applied Antisense Oligonucleotide Technology. 1998:431-48.

Krieg, CpG DNA: a pathogenic factor in systemic lupus erythematosus? J Clin Immunol. Nov. 1995;15(6):284-92.

Krieg et al., CpG motifs in bacterial DNA trigger direct B-cell activation. Nature. Apr. 6, 1995;374(6522):546-9.

Krieg et al., Modification of antisense phosphodiester oligodeoxynucleotides by a 5' cholesteryl moiety increases cellular association and improves efficacy. Proc Natl Acad Sci U S A. Feb. 1, 1993;90(3):1048-52.

Krieg et al., The role of CpG dinucleotides in DNA vaccines. Trends Microbiol. Jan. 1998;6(1):23-7.

Krieg, An innate immune defense mechanism based on the recognition of CpG motifs in microbial DNA. J Lab Clin Med. Aug. 1996;128(2);128-33.

Krieg et al., Direct immunologic activities of CpG DNA and implications for gene therapy. J Gene Med. Jan.-Feb. 1999;1(1):56-63.

Krieg et al., CpG motifs in bacterial DNA and their immune effects. Annu Rev Immunol. 2002;20:709-60.

Krieg et al., Causing a commotion in the blood: immunotherapy progresses from bacteria to bacterial DNA. Immunol Today. Oct. 2000;21(10):521-6.

Krieg et al., Chapter 8: Immune Stimulation by Oligonucleotides. In: Antisense Research and Application. Crooke, Ed. 1998:243-62.

Krieg et al., A role for endogenous retroviral sequences in the regulation of lymphocyte activation. J Immunol. Oct. 15, 1989;143(8):2448-51.

Krieg et al., Bacterial DNA or oligonucleotides containing CpG motifs protect mice from lethal L. monocytogenes challenge. 1996 Meeting on Molecular Approaches to the Control of Infectious Diseases. Cold Spring Harbor Laboratory, Sep. 9-13, 1996:116.

Krieg et al., Enhancing vaccines with immune stimulatory CpG DNA. Curr Opin Mol Ther. Feb. 2001;3(1):15-24.

Krieg et al., Chapter 7: CpG oligonucleotides as immune adjuvants. Ernst Schering Research Found Workshop 2001; 30:105-18.

Krieg, Immune effects and mechanisms of action of CpG motifs. Vaccine. Nov. 8, 2000;19(6):618-22.

Krieg et al., Chapter 17:Immune stimulation by oligonucleotides. in Antisense Drug Tech. 2001;1394:471-515.

Krieg et al., Mechanisms and applications of immune stimulatory CpG oligodeoxynucleotides. Biochim Biophys Acta. Dec. 10, 1999;1489(1):107-16.

Krieg et al., The CpG motif: Implications for clinical immunology. BioDrugs. Nov. 1, 1998;10(5):341-6.

Krieg, The role of CpG motifs in innate immunity. Curr Opin Immunol. Feb. 2000;12(1):35-43.

Krieg et al., Mechanism of action of CpG DNA. Curr Top Microbiol Immunol. 2000;247:1-21.

Krieg et al., Mechanisms and therapeutic applications of immune stimulatory CpG DNA. Pharmacol Ther. Nov. 1999;84(2):113-20.

Krieg et al., CpG DNA induces sustained IL-12 expression in vivo and resistance to Listeria monocytogenes challenge. J Immunol. Sep. 1, 1998;161(5):2428-34.

Krieg et al., CpG DNA: a novel immunomodulator. Trends Microbiol. Feb. 1999;7(2):64-5.

Krieg, Signal transduction induced by immunostimulatory CpG DNA. Springer Semin Immunopathol. 2000;22(1-2):97-105.

Krieg et al., Unmethylated CpG DNA protects mice from lethal listeria monocytogenes challenge. Vaccines. 1997; 97:77-9.

Krieg et al., Infection. In: McGraw Hill Book. 1996:242-3.

Krieg et al., Lymphocyte activation by CpG dinucleotide motifs in prokaryotic DNA. Trends Microbiol. Feb. 1996;4(2):73-6.

Krieg, Therapeutic potential of Toll-like receptor 9 activation. Nat Rev Drug Discov. Jun. 2006;5(6):471-84.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Kukowska-Latallo et al., Efficient transfer of genetic material into mammalian cells using Starburst polyamidoamine dendrimers. Proc Natl Acad Sci U S A. May 14, 1996;93(10):4897-902.

Kulkarni et al., Effect of dietary nucleotides on response to bacterial infections. JPEN J Parenter Enteral Nutr. Mar.-Apr. 1986;10(2):169-71.

Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.

Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.

Kuramoto et al., Oligonucleotide sequences required for natural killer cell activation. Jpn J Cancer Res. Nov. 1992;83(11):1128-31.

Kuramoto et al., In situ infiltration of natural killer-like cells induced by intradermal injection of the nucleic acid fraction from BCG. Microbiol Immuno. 1989;33(11):929-40.

LeClerc et al., The preferential induction of a Th1 immune response by DNA-based immunization is mediated by the immunostimulatory effect of plasmid DNA. Cell Immunol. Aug. 1, 1997;179(2):97-106.

Lederman et al., Polydeoxyguanine motifs in a 12-mer phosphorothioate oligodeoxynucleotide augment binding to the v3 loop of HIV-1 gp 120 and potency of HIV-1 inhibition independency of G-tetrad formation. Antisense Nucleic Acid Drug Dev. 1996 Winter;6(4):281-9.

Leibson et al., Role of gamma-interferon in antibody-producing responses. Nature. Jun. 28-Jul. 4, 1984;309(5971):799-801.

Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.

Letsinger et al., Synthesis and properties of modified oligonucleotides. Nucleic Acids Symp Ser. 1991;(24):75-8.

Lipford et al., CpG-containing synthetic oligonucleotides promote B and cytotoxic T cell responses to protein antigen: a new class of vaccine adjuvants. Eur J Immunol. Sep. 1997;27(9):2340-4.

Lipford et al., Immunostimulatory DNA: sequence-dependent production of potentially harmful or useful cytokines. Eur J Immunol. Dec. 1997;27(12):3420-6.

Litzinger et al., Fate of cationic liposomes and their complex with oligonucleotide in vivo, Biochim Biophys Acta. Jun. 11, 1996;1281(2):139-49.

Liu et al., Recombinant interleukin-6 protects mice against experimetnal bacterial infection. Infect Immun. Oct. 1992;60(10):4402-6.

Liu et al., CpG ODN is an effective adjuvant in immunization with tumor antigen. J Invest Med. Sep. 7, 1997;45(7):333A.

Liu et al., Immunization of non-human primates with DNA vaccines. Vaccine. Jun. 1997;15(8):909-12.

Lukacs et al., Interleukin-4-dependent pulmonary eosinophil infiltration in a murine model of asthma. Am J Respir Cell Mol Biol. May 1994;10(5):526-32.

Lukacs et al., C-C chemokine-induced eosinophil chemotaxis during allergic airway inflammation. J Leukoc Biol. Nov. 1996;60(5);573-8.

Mackellar et al., Synthesis and physical properties of anti-HIV antisense oligonucleotides bearing terminal lipophilic groups. Nucleic Acids Res. Jul. 11, 1992;20(13):3411-7.

Maloy et al., Induction of Th1 and Th2 CD4+ T cell repsonses by oral or parenteral immunization with ISCOMS. Eur J Immunol. Oct. 1995;25(10):2835-41.

Mancilla-Ramirez et al., [Phosphatidylcholine induces an increase in the production of interleukin-6 and improves survival of rats with neonatal sepsis caused by Klebsiella pneumoniae] Gac Med Mex. Jan.-Feb. 1995;131(1):14-22. Spanish.

Matsukura et al., Regulation of viral expression of human immunodeficiency virus in vitro by an antisense phosphorothioate oligodeoxynucleotide against rev (art/trs) in chronically infected cells. Proc Natl Acad Sci U S A. Jun. 1989;86(11):4244-8.

McGhee et al., The mucosal immune system: from fundamental concepts to vaccine development. Vaccine. 1992;10(2):75-88.

Messina et al., The influence of DNA structure on the in vitro stimulation of murine lymphocytes by natural and synthetic polynucleotide antigens. Cell Immunol. Mar. 1993;147(1):148-57.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Mosmann et al., The expanding universe of T-cell subsets: Th1, Th2 and more. Immunol Today. Mar. 1996;17(3):138-46.

Nielsen et al., Peptide nucleic acid (PNA). A DNA mimic with a peptide backbone. Bioconjug Chem. Jan.-Feb. 1994;5(1):3-7.

Nyce et al., DNA antisense therapy for asthma in an animal model. Nature. Feb. 20, 1997;385(6618):721-5.

Pisetsky et al., The immunologic properties of DNA. J Immunol. Jan. 15, 1996;156(2):421-3.

Pisetsky et al., Immunological properties of bacterial DNA. Ann NY Acad Sci. Nov. 27, 1995;772:152-63.

Pisetsky et al., Stimulation of murine lymphocyte proliferation by a phosphorothioate oligonucleotide with antisense activity for herpes simplex virus. Life Sci. 1994;54(2):101-7.

Pisetsky, Immunologic consequences of nucleic acid therapy. Antisense Res Dev. 1995 Fall;5(3):219-25.

Pisetsky et al., Stimulation of in vitro proliferation of murine lymphocytes by synthetic oligodeoxynucleotides. Mol Biol Rep. Oct. 1993;18(3):217-21.

Pisetsky et al., Immune activation by bacterial DNA: a new genetic code. Immunity. Oct. 1996;5(4):303-10.

Raz et al., Potential role of immunostimulatory DNA sequences (ISS) in genetic immunization and autoimmunity. ACR Poster Session C: Cytokines and Inflammatory Mediators. Oct. 20, 1996; Abstract 615.

Raz et al., Preferential induction of a Th1 immune response and inhibition of specific IgE antibody formation by plasmid DNA immunization. Proc Natl Acad Sci U S A. May 14. 1996;93(10);5141-5.

Reitz et al., Small-molecule immunostimulants. Synthesis and activity of 7,8-disubstituted guanosines and structurally related compounds. J Med Chem. Oct. 14. 1994;37(21):3561-78.

Ricci et al., T cells, cytokines, IgE and allergic airways inflammation. J Investig Allergol Clin Immunol. Sep.-Oct. 1994;4(5):214-20.

Robertson et al., Crohn's trial shows the pros of antisense. Nat Biotechnol. Mar. 1997;15(3):209.

Robinson et al., Predominant TH2-like bronchoalveolar T-lymphocyte population in atopic asthma. N Engl J Med. Jan. 30, 1992;326(5):298-304.

Robinson, Nucleic acid vaccines: an overview. Vaccine. Jun. 1997;15(8):785-7.

Rodgers et al., Effects of acute administration of O,S,S-trimethyl phosphorodithioate on the generation of cellular and humoral immune responses following in vitro stimulation. Toxicology. Oct. 1988;51(2-3):241-3.

Roman et al., Immunostimulatory DNA sequences function as T helper-1-promoting adjuvants. Nat Med. Aug. 1997;3(8):849-54.

Sands et al., Biodistribution and metabolism of internally 3H-labeled oligonucleotides. I. Comparison of a phosphodiester and a phosphorothioate. Mol Pharmacol. May 1994;45(5):932-43.

Sato et al., Immunostimulatory DNA sequences necessary for effective intradermal gene immunization. Science. Jul. 19, 1996;273(5273):352-4.

Schwartz et al., CpG motifs in bacterial DNA cause inflammation in the lower respiratory tract. J Clin Invest. Jul. 1, 1997;100(1):68-73.

Sedegah et al., Interleukin 12 induction of interferon gamma-dependent protection against malaria. Proc Natl Acad Sci U S A. Oct. 25, 1994;91(22):10700-2.

Sidman et al., Gamma-interferon is one of several direct B cell-maturing lymphokines. Nature. Jun. 28-Jul. 4, 1984;309(5971):801-4.

Sjölander et al., Kinetics, localization and isotype profile of antibody responses to immune stimulating complexes (iscoms) containing human influenza virus envelope glycoproteins. Scand J Immunol. Feb. 1996;43(2):164-72.

Sjölander et al., Iscoms containing purified *Quillaja saponins* upregulate both Th1-like and Th2-like immune responses. Cell Immunol. Apr. 10, 1997;177(1):69-76.

Sonehara et al., Hexamer palindromic oligonucleotides with 5'-CG-3' motif(s) induce production of interferon. J Interferon Cytokine Res. Oct. 1996;16(10):799-803.

Sparwasser et al., Bacterial DNA causes septic shock. Nature. Mar. 27, 1997;386(6623):336-7.

Sparwasser et al., Macrophages sense pathogens via DNA motifs: induction of tumor necrosis factor-alpha-mediated shock. Eur J Immunol. Jul. 1997;27(7):1671-9.

Staats et al., Mucosal immunity to infection with implications for vaccine development. Curr Opin Immunol. Aug. 1994;6(4):572-83.

Stein et al., Problems in interpretation of data derived from in vitro and in vivo use of antisense oligodeoxynucleotides. Antisense Res Dev. 1994 Summer;4(2):67-9.

Stein et al., Physicochemical properties of phosphorothioate oligodeoxynucleotides. Nucleic Acids Res. Apr. 25, 1988;16(8):3209-21.

Stein et al., Non-antisense effects of oligodeoxynucleotides. Antisense Technology. 1997; ch11:241-64.

Stein et al., Antisense oligonucleotides as therapeutic agents—is the bullet really magical? Science. Aug. 20, 1993;261(5124):1004-12.

Stirchak et al., Uncharged stereoregular nucleic acid analogs: 2. Morpholino nucleoside oligomers with carbamate internucleoside linkages. Nucleic Acids Res. Aug. 11, 1989;17(15):6129-41.

Tarköy et al., Nucleic-Acid Analogues with Constraint Conformational Flexibility in the Sugar-Phosphate Backbone ('Bicyclo-DNA'). Part 1, Preparation of (3S,5'R)-2'-Deoxy-3',5'-ethano-$\alpha\beta$-D-ribonucleosides ('Bicyclonucleosides'). Helv Chim Acta. Feb. 10, 1993;76(1): 481-510.

Threadgill et al., Mitogenic synthetic polynucleotides suppress the antibody response to a bacterial polysaccharide. Vaccine. Jan. 1998;16(1):76-82.

Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.

Tokunaga et al., Synthetic oligonucleotides with particular base sequences from the cDNA encoding proteins of Mycobacterium bovis BCG induce interferons and activate natural killer cells. Microbiol Immunl. 1992;36(1):55-66.

Vlassov et al., In Vivo pharmocokinetics of oligonucleotides following administration by different routes. CRC Press, Inc. Chapter 5. 1995:71-83.

Waag et al., Injection of inactivated phase 1 *Coxiella burnetii* increases non-specific resistance to infection and stimulates lymphokine production in mice. Ann N Y Acad Sci. 1990;590:203-14.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Whitesell et al., Stability, clearance, and disposition of intraventricularly administered oligodeoxynucleotides: implications for therapeutic application within the cental nervous system. Proc Natl Acad Sci U S A. May 15, 1993;90(10):4665-9.

Wu et al., Receptor-mediated gene delivery and expression in vivo. J Biol Chem. Oct. 15, 1988;263(29):14621-4.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.

Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4. Japanese.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8);775-9. Abstract Only.

Yamamoto, Cytokine production inducing action of oligo DNA. Rinsho Meneki. 1997; 29(9):1178-854. Japanese.

Yi et al., Rapid immune activation by CpG motifs in bacterial DNA. Systemic induction of IL-6 transcription through an antioxidant-sensitive pathway. J Immunol. Dec. 15, 1996;157(12):5394-402.

Yi et al., IFN-gamma promotes IL-6 and IgM secretion in response to CpG motifs in bacterial DNA and oligodeoxynucleotides. J Immunol. Jan. 15, 1996;156(2):558-64.

Yi et al., CpG DNA rescue of murine B lymphoma cells from anti-IgM-induced growth arrest and programmed cell death is associated with increased expression of c-myc and bcl-xL. J Immunol. Dec. 1, 1996;157(11):4918-25.

Zhao et al., Pattern and kinetics of cytokine production following administration of phosphorothioate oligonucleotides in mice. Antisense Nucleic Acid Drug Dev. Oct. 1997;7(5):495-502.

Zhao et al., Modulation of oligonucleotide-induced immune stimulation by cyclodextrin analogs. Biochem Pharmacol. Nov. 22, 1996;52(10):1537-44.

Zhao et al., Effect of different chemically modified oligodeoxynucleotides on immune stimulation. Biochem Pharmacol. Jan. 26, 1996;51(2):173-82.

Patent Interference No. 105,171. Iowa Preliminary Motion 3 (for judgment based on failure to comply with 35 U.S.C. 135(b)). (Electronically filed, unsigned). Jun. 7, 2004.

Patent Interference No. 105,171. Iowa Preliminary Motion 4 (for judgment of no interference in fact). (Electronically filed, unsigned). Jun. 7, 2004.

Patent Interference No. 105,171. Iowa Preliminary Motion 5 (for judgment based on lack of enablement). (Electronically filed, unsigned). Jun. 7, 2004.

Patent Interference No. 105,171. Iowa Preliminary Motion 6 (for judgment based on lack of adequate written description). (Electronically filed, unsigned). Jun. 7, 2004.

Patent Interference No. 105,171. Iowa Preliminary Motion 7 (motion to redefine interference to designate claims as not corresponding to the Count). (Electronically filed, unsigned). Jun. 7, 2004.

Patent Interference No. 105,171. Iowa Preliminary Motion 8 (contingent motion to redefine the Count). (Electronically filed, unsigned). Jun. 7, 2004.

Patent Interference No. 105,171. Iowa Preliminary Motion 9 (motion for benefit of earlier application). (Electronically filed, unsigned). Jun. 7, 2004.

Patent Interference No. 105,171. Iowa Preliminary Motion 10 (contingent motion to redefine the interference by adding a continuation application). (Electronically filed, unsigned). Jul. 2, 2004.

Patent Interference No. 105,171. Regents of the University of California Opposition 3 (to Iowa Preliminary Motion 3 for judgment under 35 USC 135(b)). Sep. 9, 2004.

Patent Interference No. 105,171. Regents of the University of California Opposition 4 (to Iowa Preliminary Motion 4 for judgment of no interference in fact). Sep. 9, 2004.

Patent Interference No. 105,171. Regents of the University of California Opposition 5 (to Iowa Preliminary Motion 5 for judgment that UC's claim is not enabled). Sep. 9, 2004.

Patent Interference No. 105,171. Regents of the University of California Opposition 6 (to Iowa Preliminary Motion 6 for judgment based on lack of adequate written description). Sep. 9, 2004.

Patent Interference No. 105,171. Regents of the University of California Opposition 7 (to Iowa Preliminary Motion 7 to redefine the interference). Sep. 9, 2004.

Patent Interference No. 105,171. Regents of the University of California Opposition 8 (to Iowa Preliminary Motion 8 to redefine the Count). Sep. 9, 2004.

Patent Interference No. 105,171. Regents of the University of California Response 9 (to Iowa Contingent Motion 9 for benefit). Sep. 9, 2004.

Patent Interference No. 105,171. Regents of the University of California Opposition 10 (to Iowa Contingent Motion 10 to redefine the interference). Sep. 9, 2004.

Patent Interference No. 105,171. Regents of the University of California Opposition 11 (to Iowa Contingent Motion 11 to suppress). Oct. 15, 2004.

Patent Interference No. 105,171. Iowa Reply 3 (in support of Iowa Preliminary Motion 3 for judgment under 35 U.S.C. § 135(b)) (Electronically filed, unsigned). Oct. 15, 2004.

Patent Interference No. 105,171. Iowa Reply 4 (in support of Iowa Preliminary Motion for judgment of no interference in fact) (Electronically filed, unsigned). Oct. 15, 2004.

Patent Interference No. 105,171. Iowa Reply 5 (in support of Iowa Preliminary Motion 5 for judgment that UC's claim 205 is not enabled) (Electronically filed, unsigned). Oct. 15, 2004.

Patent Interference No. 105,171. Iowa Reply 6 (in support of Iowa Preliminary Motion 6 for judgment based on lack of adequate written description) (Electronically filed, unsigned). Oct. 15, 2004.

Patent Interference No. 105,171. Iowa Reply 7 (in support of Iowa Preliminary Motion 7 to redefine the interference) (Electronically filed, unsigned). Oct. 15, 2004.

Patent Interference No. 105,171. Iowa Reply 8 (in support of Iowa Preliminary Motion 8 to redefine the count) (Electronically filed, unsigned). Oct. 15, 2004.

Patent Interference No. 105,171. Iowa Reply 10 (in support of Iowa Preliminary Motion 10 to redefine the interference) (Electronically filed, unsigned). Oct. 15, 2004.

Patent Interference No. 105,171. Iowa Reply 11 (in support of Iowa Miscellaneous Motion to suppress). (Electronically filed, unsigned). Oct. 18, 2004.

Patent Interference No. 105,171. Regents of the University of California Preliminary Statement. Jun. 7, 2004.

Patent Interference No. 105,171. Regents of the University of California Preliminary Motion 1 (to designate additonal claims to Iowa patent as corresponding to the Count). Jun. 7, 2004.

Patent Interference No. 105,171. Regents of the University of California Preliminary Motion 2 (for judgment based on lack of written description support and introducing new matter). Jun. 7, 2004.

Patent Interference No. 105,171. Regents of the University of California Preliminary Motion 3 (for judgment based on anticipation). Jun. 7, 2004.

Patent Interference No. 105,171. Regents of the University of California Preliminary Motion 4 (for judgment based on obviousness). Jun. 7, 2004.

Patent Interference No. 105,171. Regents of the University of California Preliminary Motion 5 (for judgment based on anticipation). Jun. 7, 2004.

Patent Interference No. 105,171. Regents of the University of California Preliminary Motion 6 (for judgment based on inequitable conduct). Jun. 7, 2004.

Patent Interference No. 105,171. Regents of the University of California Contingent Preliminary Motion 7 (for benefit of an earlier application under 37 CFR 1.633(j)). Jul. 2, 2004.

Patent Interference No. 105,171. Regents of the University of California Contingent Preliminary Motion 8 (to additional claims under 37 CFR 1.633(c)(2) and (i)). Jul. 2, 2004.

Amended Claims for U.S. Appl. No. 09/265,191, filed Mar. 10, 1999.

Patent Interference No. 105,171. Iowa Opposition 1 (opposition to motion to designate additional claims as corresponding to the Count) (Electronically filed, unsigned). Sep. 9, 2004.

Patent Interference No. 105,171. Iowa Opposition 2 (opposition to motion for judgment based on lack of written description support and introducing new matter) ( Electronically filed, unsigned). Sep. 9, 2004.

Patent Interference No. 105,171. Iowa Opposition 3 (opposition to motion for judgment based on anticipation) (Electronically filed, unsigned). Sep. 9, 2004.

Patent Interference No. 105,171. Iowa Opposition 4 (opposition to motion for judgment based on obviousness) (Electronically filed, unsigned). Sep. 9, 2004.

Patent Interference No. 105,171. Iowa Opposition 5 (opposition to motion for judgment based on anticipation) ( Electronically filed, unsigned). Sep. 9, 2004.

Patent Interference No. 105,171. Iowa Opposition 6 (opposition to motion for judgment based on inequitable conduct) (Electronically filed, unsigned). Sep. 9, 2004.

Patent Interference No. 105,171. Iowa Opposition 7 (opposition to motion for benefit of an earlier application under 7 CFR 1.633(j)) (Electronically filed, unsigned). Sep. 9, 2004.

Patent Interference No. 105,171. Iowa Opposition 8 (opposition to motion to add additional claims under 37 CFR 1.633 (2) and (i)) (Electronically filed, unsigned). Sep. 9, 2004.

Patent Interference No. 105,171. Regents of the University of California Reply 1 (to Iowa's opposition to UC's motion to designate Iowa claims as corresponding to the Count). Oct. 15, 2004.

Patent Interference No. 105,171. Regents of the University of California Reply 2 (to Iowa's opposition to UC Preliminary Motion 2 for Judgment). Oct. 15, 2004.
Patent Interference No. 105,171. Regents of the University of California Reply 3 (to Iowa's Opposition to UC Preliminary Motion 3 for Judgment). Oct. 15, 2004.
Patent Interference No. 105,171. Regents of the University of California Reply 4 (to Iowa's Opposition to UC Preliminary Motion 4 for Judgment). Oct. 15, 2004.
Patent Interference No. 105,171. Regents of the University of California Reply 5 (to Iowa's Opposition to UC Preliminary Motion 5 for Judgment). Oct. 15, 2004.
Patent Interference No. 105,171. Regents of the University of California Reply 6 (to Iowa's opposition to UC Preliminary Motion 6 for judgment). Oct. 15, 2004.
Patent Interference No. 105,171. Regents of the University of California Reply 7 (to Iowa's Opposition to UC Preliminary Motion 7 for Benefit). Oct. 15, 2004.
Patent Interference No. 105,171. Regents of the University of California Reply 8 (to Iowa's Opposition to UC Preliminary Motion 8 to add additional claims). Oct. 15, 2004.
Patent Interference No. 105,171. Decision on Motion under 37 CFR §41.125. Mar. 10, 2005.
Patent Interference No. 105,171. Judgment and Order. Mar. 10, 2005.
Patent Interference No. 105,171. Regents of the University of California. Brief of Appellant. Jul. 5, 2005.
Patent Interference No. 105,171. University of Iowa and Coley Pharmaceutical Group, Inc. Brief of Appellees. Aug. 17, 2005.
Patent Interference No. 105,171. Regents of the University of California. Reply Brief of Appellant. Sep. 6, 2005.
Patent Interference No. 105,171. Regents of the University of California. Decision of CAFC. Jul. 17, 2006.
Press Release, Jan. 2007, "Coley Pharmaceutical Group Updates Hepatitis C Drug Development Strategy".
Press Release, Jun. 2007, "Coley Pharmaceutical Group Announces Pfizer's Discontinuation of Clinical Trial for PF-3512676 Combined with Cytotoxic Chemotherapy in Advanced Non Small Cell Lung Cancer".
Bennett, Intracellular delivery of oligonucleotides with cationic liposomes. In: Delivery Strategies for Antisense Oligonucleotide Therapeutics. Akthar, Ed. 1995:223-32. Abstract Only.
Kline et al., T-lymphocyte dysregulation in asthma. Proc Soc Exp Biol Med. Dec. 1994;207(3):243-53.
Kline et al., Effects of CpG DNA on Th1/Th2 balance in asthma. Curr Top Microbiol Immunol. 2000;247:211-25.
Patent Interference No. 105,526. Krieg Substantive Motion 1 (for unpatentability based on interference estoppel). (Electronically filed, unsigned).
Patent Interference No. 105,526.. Krieg Substantive Motion 2 (for judgment based on inadequate written description and/or enablement). (Electronically filed, unsigned). Jun. 18, 2007.
Patent Interference No. 105,526. Krieg Contingent Responsive Motion (to add new claims 104 and 105). (Electronically filed, unsigned). Jul. 25, 2007.
Patent Interference No. 105,526. Krieg Substantive Motion 3 (for judgment based on prior art). (Electronically filed, unsigned). Jun. 18, 2007.
Patent Interference No. 105,526. Raz Motion 1 (Unpatentability of Krieg Claims under 35 U.S.C. § 112, First Paragraph). (Electronically filed, unsigned). Jun. 18, 2007.
Patent Interference No. 105,526. Raz Motion 2 (Raising a Threshold Issue of No Interference-in-Fact). (Electronically filed, unsigned). Jun. 18, 2007.
Patent Interference No. 105,526.. Raz Motion 3 ( Krieg's Claims are Unpatentable Over Prior Art Under 35 U.S.C. § 102(b)) (Electronically filed, unsigned). Jun. 18, 2007.
Patent Interference No. 105,526. Raz Motion 4 (To Designate Krieg Claims 46 and 82-84 as Corresponding to Count 1). (Electronically filed, unsigned). Jun. 18, 2007.
Patent Interference No. 105,526. Raz Responsive Miscellaneous Motion 5 ( To revive the Raz Parent Application) (Electronically filed, unsigned) Jul. 25, 2007.
Patent Interference No. 105,526. Raz Contingent Responsive Motion 6 (To Add a New Claim 58) (Electronically filed, unsigned) Jul. 25, 2007.
Patent Interference No. 105,526. Krieg Opposition 1 (Opposition to Motion for Lack of Enablement and Written Description) (Electronically filed, unsigned) Sep. 10, 2007.
Patent Interference No. 105,526. Krieg Opposition 2 (to Raz Motion 2) (Electronically filed, unsigned) Sep. 10, 2007.
Patent Interference No. 105,526. Krieg Opposition 3 (To Raz Motion 3) (Electronically filed, unsiged) Sep. 10, 2007.
Patent Interference No. 105,526. Krieg Opposition 4 (Oppostion to Motion for Designating Claims 46 and 82-84 as Corresponding to the Court) (Electronically filed, unsigned) Sep. 10, 2007.
Patent Interference No. 105,526. Krieg Opposition 6 (Opposition to Raz Contingent Responsive Motion 6) (Electronically filed, unsigned) Sep. 10, 2007.
Patent Interference No. 105,526. Raz Opposition 1 (Opposing Krieg Substantive Motion 1) (Electronically filed, unsigned) Sep. 10, 2007.
Patent Interference No. 105,526. Raz Opposition 2 (Opposing Krieg Substantive Motion 2) (Electronically filed, unsigned) Sep. 10, 2007.
Patent Interference No. 105,526. Raz Opposition 4 (Opposing Krieg Contingent Responsive Motion to Add New Claims 104 and 105) (Electronically filed, unsigned) Sep. 10, 2007.
Patent Interference No. 105,526. Krieg Reply 1 (Reply to Raz opposition 1) Oct. 5, 2007.
Patent Interference No. 105,526. Krieg Reply 2 (Reply to Raz opposition 2) Oct. 5, 2007.
Patent Interference No. 105,526. Krieg Reply 4 (Reply to Raz opposition 4) Oct. 5, 2007.
Patent Interference No. 105,526. Raz Reply 1 (Reply to Krieg opposition 1) Oct. 5, 2007.
Patent Interference No. 105,526. Raz Reply 2 (Reply to Krieg opposition 2) Oct. 5, 2007.
Patent Interference No. 105,526. Raz Reply 3 (Reply to Krieg opposition 3) Oct. 5, 2007.
Patent Interference No. 105,526. Raz Reply 4 (Reply to Krieg opposition 4) Oct. 5, 2007.
Patent Interference No. 105,526. Raz Reply 6 (Reply to Krieg opposition 6) Oct. 5, 2007.
Patent Interference No. 105,526. Krieg Miscellaneous Motion 5 (To exclude exhibits 2066, 2070, 2071, 2072, 2073, 2074, 2075, 2076 and 2078) Oct. 9, 2007.
Patent Interference No. 105,526. Raz Opposition 5 (Opposing Krieg Miscellaneous Motion 5) Oct. 25, 2007.
Patent Interference No. 105,526. Raz Miscellaneous Motion 7 (To exclude evidence) Oct. 19, 2007.
Patent Interference No. 105,526. Krieg Opposition 7 (To Raz Miscellaneous Motion 7) Oct. 25, 2007.
Patent Interference No. 105,526. Krieg Reply 5 (Reply to Raz opposition 5) Oct. 30, 2007.
Patent Interference No. 105,526. Raz Reply 7 (Reply To Krieg opposition 7) Oct. 30, 2007.

* cited by examiner

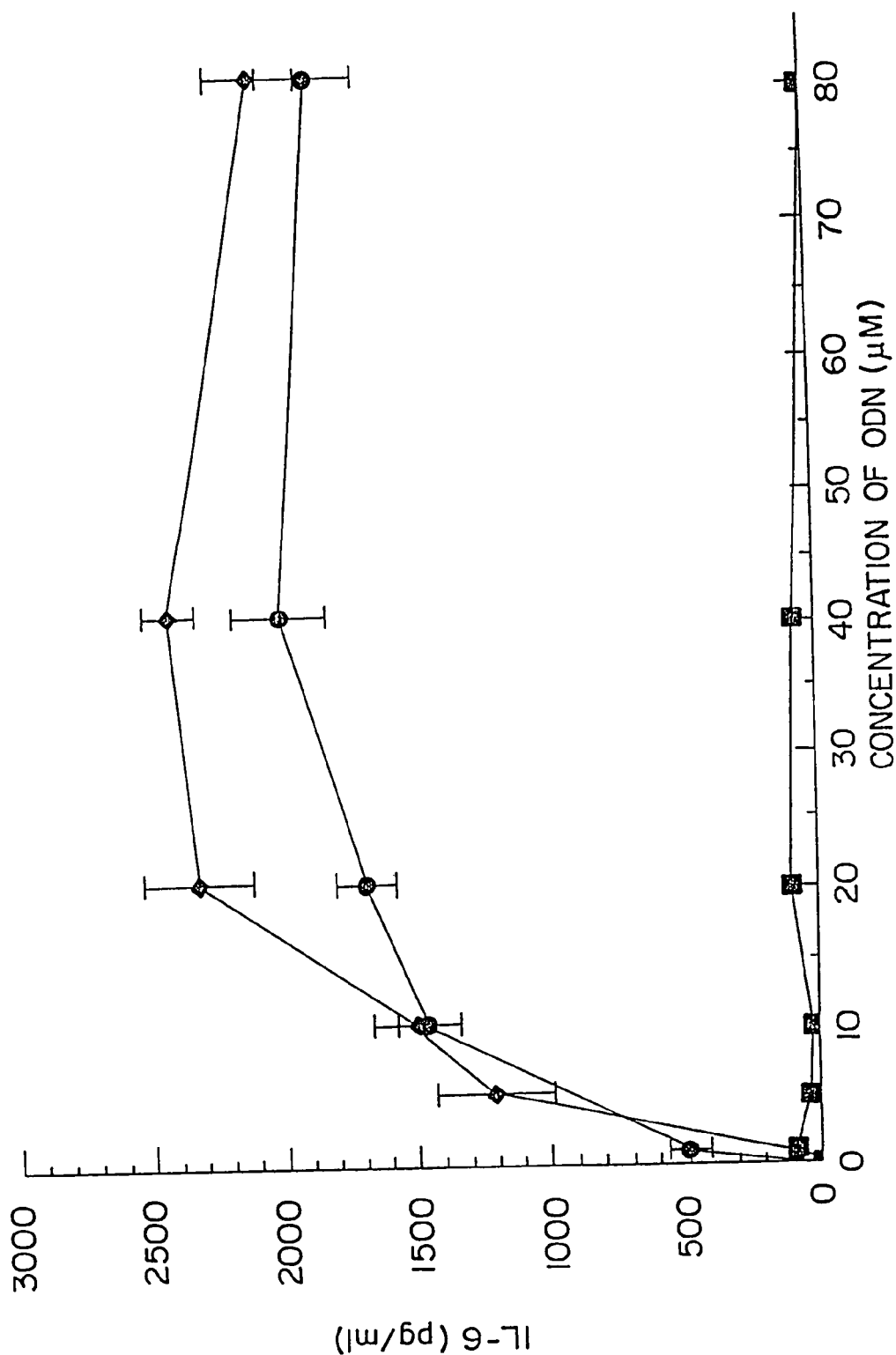

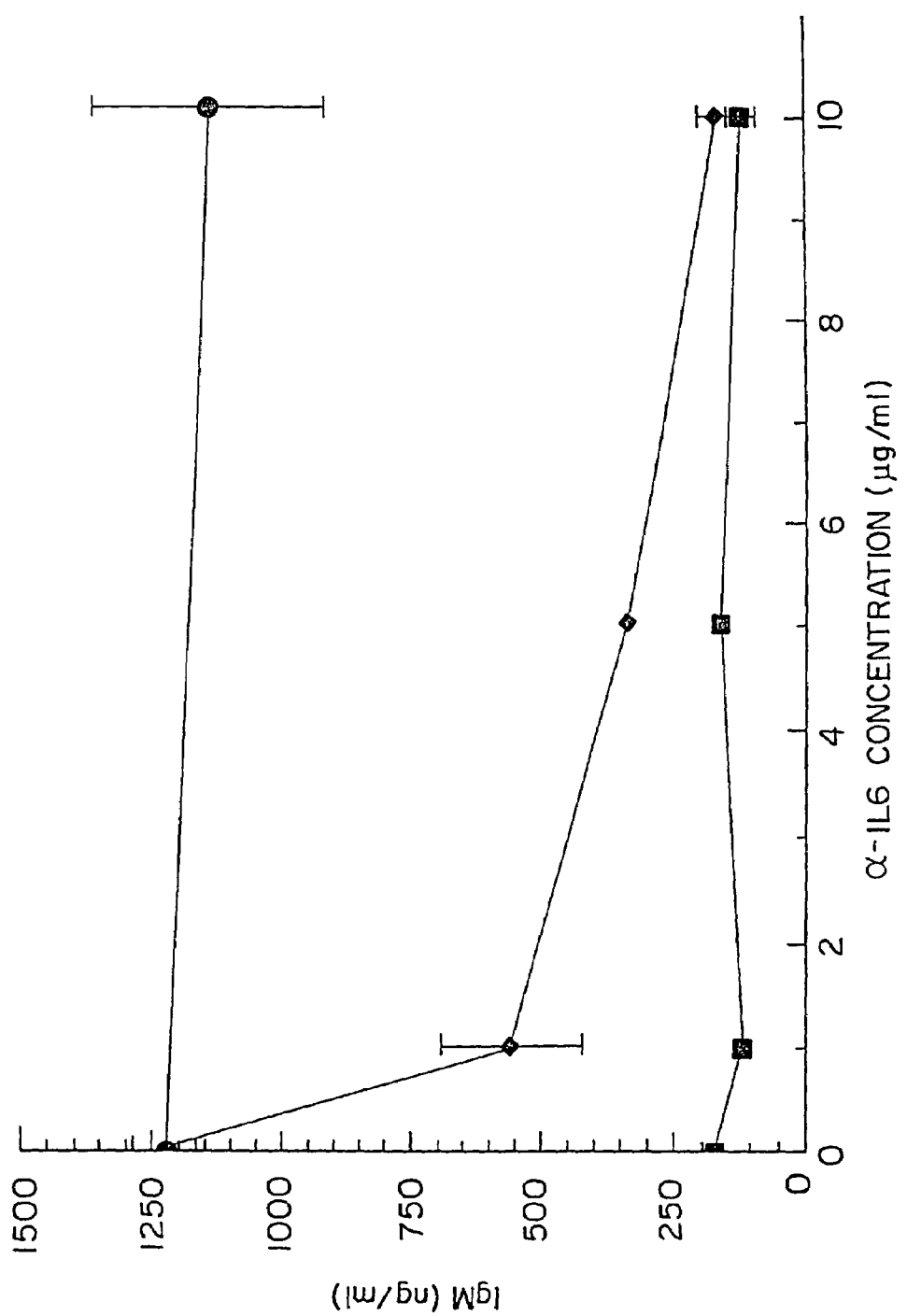

IMMUNOSTIMULATORY NUCLEIC ACID MOLECULES

RELATED APPLICATIONS

This application is a continuation of U.S. patent application Ser. No. 09/818,918 filed Mar. 27, 2001, which is divisional of U.S. patent application Ser. No. 08/738,652, filed Oct. 30, 1996, now issued as U.S. Pat. No. 6,207,646 B1, which is a continuation-in-part of U.S. patent application Ser. No. 08/386,063, filed Feb. 7, 1995, now issued as U.S. Pat. No. 6,194,388 B1, which is a continuation-in-part of U.S. patent application Ser. No. 08/276,358, filed Jul. 15, 1994, now abandoned.

GOVERNMENT SUPPORT

The work resulting in this invention was supported in part by National Institute of Health Grant No. R29-AR42556-01. The U.S. Government may therefore be entitled to certain rights in the invention.

BACKGROUND OF THE INVENTION

DNA Binds to Cell Membranes and is Internalized

In the 1970's, several investigators reported the binding of high molecular weight DNA to cell membranes (Lerner, R. A., W. Meinke, and D. A. Goldstein. 1971. "Membrane-associated DNA in the cytoplasm of diploid human lymphocytes". *Proc. Natl. Acad. Sci. USA* 68:1212; Agrawal, S. K., R. W. Wagner, P. K. McAllister, and B. Rosenberg. 1975. "Cell-surface-associated nucleic acid in tumorigenic cells made visible with platinum-pyrimidine complexes by electron microscopy". *Proc. Natl. A cad. Sci. USA* 72:928). In 1985, Bennett et al. presented the first evidence that DNA binding to lymphocytes is similar to a ligand receptor interaction: binding is saturable, competitive, and leads to DNA endocytosis and degradation into oligonucleotides (Bennett, R. M., G. T. Gabor, and M. M. Merritt. 1985. "DNA binding to human leukocytes. Evidence for a receptor-mediated association, internalization, and degradation of DNA". *J. Clin. Invest.* 76:2182). Like DNA, oligodeoxyribonucleotides (ODNs) are able to enter cells in a saturable, sequence independent, and temperature and energy dependent fashion (reviewed in Jaroszewski, J. W., and J. S. Cohen. 1991. "Cellular uptake of antisense oligodeoxynucleotides". *Advanced Drug Delivery Reviews* 6:235; Akhtar, S., Y. Shoji, and R.L. Juliano. 1992. "Pharmaceutical aspects of the biological stability and membrane transport characteristics of antisense oligonucleotides". In: *Gene Regulation: Biology of Antisense RNA and DNA*. R. P. Erickson, and J. G. Izant, eds. Raven Press, Ltd. New York, pp. 133; and Zhao, Q., T. Waldschmidt, E. Fisher, C. J. Herrera, and A. M. Krieg., 1994. "Stage specific oligonucleotide uptake in murine bone marrow B cell precursors". *Blood,* 84:3660). No receptor for DNA or ODN uptake has yet been cloned, and it is not yet clear whether ODN binding and cell uptake occurs through the same or a different mechanism from that of high molecular weight DNA.

Lymphocyte ODN uptake has been shown to be regulated by cell activation. Spleen cells stimulated with the B cell mitogen LPS had dramatically enhanced ODN uptake in the B cell population, while spleen cells treated with the T cell mitogen Con A showed enhanced ODN uptake by T but not B cells (Krieg, A. M., F. Gmelig-Meyling, M. F. Gourley, W. J. Kisch, L. A. Chrisey, and A.D. Steinberg. 1991. "Uptake of oligodeoxyribonucleotides by lymphoid cells is heterogeneous and inducible". *Antisense Research and Development* 1:161).

Immune Effects of Nucleic Acids

Several polynucleotides have been extensively evaluated as biological response modifiers. Perhaps the best example is poly (I,C) which is a potent inducer of IFN production as well as a macrophage activator and inducer of NK activity (Talmadge, J. E., J. Adams, H. Phillips, M. Collins, B. Lenz, M. Schneider, E. Schlick, R. Ruffmann, R. H.. Wiltrout, and M. A. Chirigos. 1985. "Immunomodulatory effects in mice of polyinosinic-polycytidylic acid complexed with poly-L-lysine and carboxymethylcellulose". *Cancer Res.* 45:1058; Wiltrout, R. H., R. R. Salup, T. A. Twilley, and J. E. Talmadge. 1985. "Immunomodulation of natural killer activity by polyribonucleotides". *J. Bid. Resp. Mod.* 4:512; Krown, S. E. 1986. "Interferons and interferon inducers in cancer treatment". *Sem. Oncol.* 13:207; and Ewel, C. H., S. J. Urba, W. C. Kopp, J. W. Smith II, R. G. Steis, J. L. Rossio, D. L. Longo, M. J. Jones, W. G. Alvord, C. M. Pinsky, J. M. Beveridge; K. L. McNitt, and S. P. Creekmore. 1992. "Polyinosinic-polycytidylic acid complexed with poly-L-lysine and carboxymethylcellulose in combination with interleukin-2 in patients with cancer: clinical and immunological effects". *Canc. Res.* 52:3005). It appears that this murine NK activation may be due solely to induction of IFN-β secretion (Ishikawa, R., and C. A. Biron. 1993. "IFN induction and associated changes in splenic leukocyte distribution". *J. Immunol.* 150:3713). This activation was specific for the ribose sugar since deoxyribose was ineffective. Its potent in vitro antitumor activity led to several clinical trials using poly (I,C) complexed with poly-L-lysine and carboxymethylcellulose (to reduce degradation by RNAse) (Talmadge, J. E., et al., 1985. cited supra; Wiltrout, R. H., et al., 1985. cited supra); Krown, S. E., 1986. cited supra); and Ewel, C. H., et al., 1992. cited supra). Unfortunately, toxic side effects have thus far prevented poly (I,C) from becoming a useful therapeutic agent.

Guanine ribonucleotides substituted at the C8 position with either a bromine or a thiol group are B cell mitogens and may replace "B cell differentiation factors" (Feldbush, T. L., and Z. K. Ballas. 1985. "Lymphokine-like activity of 8-mercaptoguanosine: induction of T and B cell differentiation". *J. Immunol.* 134:3204; and Goodman, M. G. 1986. "Mechanism of synergy between T cell signals and C8-substituted guanine nucleosides in humoral immunity: B lymphotropic cytokines induce responsiveness to 8-mercaptoguanosine". *J. Immunol.* 136:3335). 8-mercaptoguanosine and 8-bromoguanosine also can substitute for the cytokine requirement for the generation of MHC restricted CTL (Feldbush, T. L., 1985. cited supra), augment murine NK activity (Koo, G. C., M. E. Jewell, C. L. Manyak, N. H. Sigal, and L. S. Wicker. 1988. "Activation of murine natural killer cells and macrophages by 8-bromoguanosine". *J. Immunol.* 140:3249), and synergize with IL-2 in inducing murine LAK generation (Thompson, R. A., and Z. K. Ballas. 1990. "Lymphokine-activated killer (LAK) cells. V. 8-Mercaptoguanosine as an IL-2-sparing agent in LAK generation". *J. Immunol.* 145:3524). The NK and LAX augmenting activities of these C8-substituted guanosines appear to be due to their induction of IFN (Thompson, R. A., et al. 1990. cited supra). Recently, a 5'0 triphosphorylated thymidine produced by a mycobacterium was found to be mitogenic for a subset of human γδ T cells (Constant, P., F. Davodeau, M.-A. Peyrat, Y. Poquet, G. Puzo, M. Bonneville, and J.-J. Fournie. 1994. "Stimulation of human γδ T cells by nonpeptidic mycobacterial ligands" *Science* 264:267). This report indicated the possibility that the immune system may have evolved ways to preferentially respond to microbial nucleic acids.

Several observations suggest that certain DNA structures may also have the potential to activate lymphocytes. For example, Bell et al. reported that nucleosomal protein-DNA complexes (but not naked DNA) in spleen cell supernatants caused B cell proliferation and immunoglobulin secretion (Bell, D. A., B. Morrison, and P. VandenBygaart. 1990. "Immunogenic DNA-related factors". *J. Clin. Invest.* 85:1487). In other cases, naked DNA has been reported to have immune effects. For example, Messina et al. have recently reported that 260 to 800 bp fragments of poly (dG)•(dC) and poly (dG•dC) were mitogenic for B cells (Messina, J. P., G. S. Gilkeson, and D. S. Pisetsky. 1993. "The influence of DNA structure on the in vitro stimulation of murine lymphocytes by natural and synthetic polynucleotide antigens". *Cell. Immunol.* 147:148). Tokunaga, et al. have reported that dG•dC induces IFN-γ and NK activity (Tokunaga, S. Yamamoto, and K. Namba. 1988. "A synthetic single-stranded DNA, poly(dG,dC), induces interferon-α/ β and -γ, augments natural killer activity, and suppresses tumor growth" *Jpn. J. Cancer Res.* 79:682). Aside from such artificial homopolymer sequences, Pisetsky et al. reported that pure mammalian DNA has no detectable immune effects, but that DNA from certain bacteria induces B cell activation and immunoglobulin secretion (Messina, J. P., G. S. Gilkeson, and D. S. Pisetsky. 1991. "Stimulation of in vitro murine lymphocyte proliferation by bacterial DNA". *J. Immunol.* 147:1759). Assuming that these data did not result from some unusual contaminant, these studies suggested that a particular structure or other characteristic of bacterial DNA renders it capable of triggering B cell activation. Investigations of mycobacterial DNA sequences have demonstrated that ODN which contain certain palindrome sequences can activate NK cells (Yamamoto, S., T. Yamamoto, T. Kataoka, E. Kuramoto, O. Yano, and T. Tokunaga. 1992. "Unique palindromic sequences in synthetic oligonucleotides are required to induce INF and augment INF-mediated natural killer activity". *J. Immunol.* 148:4072; Kuramoto, E., O. Yano, Y. Kimura, M. Baba, T. Makino, S. Yamamoto, T. Yamamoto, T. Kataoka, and T. Tokunaga. 1992"Oligonucleotide sequences required for natural killer cell activation". *Jpn. J. Cancer Res.* 83:1128).

Several phosphorothioate modified ODN have been reported to induce in vitro or in vivo B cell stimulation (Tanaka, T., C. C. Chu, and W. E. Paul. 1992. "An antisense oligonucleotide complementary to a sequence in Iγ2b increases γ2b germline transcripts, stimulates B cell DNA synthesis, and inhibits immunoglobulin secretion". *J. Exp. Med.* 175:597; Branda, R. F., A. L. Moore, L. Mathews, J. J. McCormack, and G. Zon. 1993. "Immune stimulation by an antisense oligomer complementary to the rev gene of HIV-1". *Biochem. Pharmacol.* 45:2037; McIntyre, K. W., K. Lombard-Gillooly, J. R. Perez, C. Kunsch, U. M. Sarmiento, J. D. Larigan, K. T. Landreth, and R. Narayanan. 1993. "A sense phosphorothioate oligonucleotide directed to the initiation codon of transcription factor NFκB T65 causes sequence-specific immune stimulation". *Antisense Res. Develop.* 3:309; and Pisetsky, D. S., and C. F. Reich. 1993. "Stimulation of murine lymphocyte proliferation by a phosphorothioate oligonucleotide with antisense activity for herpes simplex virus". *Life Sciences* 54:101). These reports do not suggest a common structural motif or sequence element in these ODN that might explain their effects.

The CREB/ATF Family of Transcription Factors and their Role in Replication

The cAMP response element binding protein (CREB) and activating transcription factor (ATF) or CREB/ATF family of transcription factors is a ubiquitously expressed class of transcription factors of which 11 members have so far been cloned (reviewed in de Groot, R. P., and P. Sassone-Corsi: "Hormonal control of gene expression: Multiplicity and versatility of cyclic adenosine 3',5'-monophosphate-responsive nuclear regulators". *Mol. Endocrin.* 7:145, 1993; Lee, K. A. W., and N. Masson: "Transcriptional regulation by CREB and its relatives". *Biochim. Biophys. Acta* 1174:221, 1993.). They all belong to the basic region/leucine zipper (bZip) class of proteins. All cells appear to express one or more CREB/ATE proteins, but the members expressed and the regulation of mRNA splicing appear to be tissue-specific. Differential splicing of activation domains can determine whether a particular CREB/ATF protein will be a transcriptional inhibitor or activator. Many CREB/ATF proteins activate viral transcription, but some splicing variants which lack the activation domain are inhibitory. CREB/ATF proteins can bind DNA as homo- or hetero- dimers through the cAMP response element, the CRE, the consensus form of which is the unmethylated sequence TGACGTC (binding is abolished if the CpG is methylated) (Iguchi-Ariga, S. M. M., and W. Schaffner: "CpG methylation of the cAMP-responsive enhancer/promoter sequence TGACGTCA abolishes specific factor binding as well as transcriptional activation". *Genes & Develop.* 3:612, 1989.).

The transcriptional activity of the CRE is increased during B cell activation (Xie, H. T. C. Chiles, and T. L. Rothstein: "Induction of CREB activity via the surface Ig receptor of B cells". *J. Immunol.* 151:880, 1993.). CREB/ATF proteins appear to regulate the expression of multiple genes through the CRE including immunologically important genes such as fos, jun B, Rb-1, IL-6, IL-1 (Tsukada, J., K. Saito, W. R. Waterman, A. C. Webb, and P. E. Auron: "Transcription factors NF-IL6 and CREB recognize a common essential site in the human prointerleukin 1β gene". *Mol. Cell. Bid.* 14:7285, 1994; Gray, G. D., O. M. Hernandez, D. Hebel, M. Root, J. M. Pow-Sang, and E. Wickstrom: "Antisense DNA inhibition of tumor growth induced by c-Ha-ras oncogene in nude mice". *Cancer Res.* 53:577, 1993), IFN-β (Du, W., and T. Maniatis: "An ATF/CREB binding site protein is required for virus induction of the human interferon B gene". *Proc. Natl. Acad. Sci. USA* 89:2150, 1992), TGF-β1 (Asiedu, C. K., L. Scott, R. K. Assoian, M. Ehrlich: "Binding of AP-1/CREB proteins and of MDBP to contiguous sites downstream of the human TGF-B1 gene". *Biochim. Biophys. Acta* 12 19:55, 1994.), TGF-β2, class II MHC (Cox, P. M., and C. R. Goding: "An ATF/CREB binding motif is required for aberrant constitutive expression of the MHC class II DRa promoter and activation by SV40 T-antigen". *Nucl. Acids Res.* 20:4881, 1992.), E-selectin, GM-CSF, CD-8α, the germline Igα constant region gene, the TCR Vβ gene, and the proliferating cell nuclear antigen (Huang, D., P. M. Shipman-Appasamy, D. J. Orten, S. H. Hinrichs, and M. B. Prystowsky: "Promoter activity of the proliferating-cell nuclear antigen gene is associated with inducible CRE-binding proteins in interleukin 2-stimulated T lymphocytes". *Mol. Cell. Biol.* 14:4233, 1994.). In addition to activation through the cAMP pathway, CREB can also mediate transcriptional responses to changes in intracellular $Ca^{++}$ concentration (Sheng, M., G. McFadden, and M. E. Greenberg: "Membrane depolarization and calcium induce c-fos transcription via phosphorylation of transcription factor CREB". *Neuron* 4:571, 1990).

The role of protein-protein interactions in transcriptional activation by CREB/ATF proteins appears to be extremely important. There are several published studies reporting direct or indirect interactions between NFKB proteins and CREB/ATF proteins (Whitley, et. al., (1994) *Mol. & Cell. Biol.* 14:6464; Cogswell, et al., (1994) *J. Immun.* 153:712; Hines, et al., (1993) Oncogene 8:3189; and Du, et al., (1993) *Cell* 74:887. Activation of CREB through the cyclic AMP pathway requires protein kinase A (PKA), which phosphorylates CREB[341] on ser[133] and allows it to bind to a recently cloned protein, CBP (Kwok, R. P. S., J. R. Lundblad, J. C. Chrivia, J.P. Richards, H. P. Bachinger, R. G. Brennan, S. G. E. Roberts, M. R. Green, and R. H. Goodman: "Nuclear protein CBP is a coactivator for the transcription factor CREB". *Nature* 370:223, 1994; Arias, J., A. S. Alberts, P. Brindle, F. X. Claret, T. Smea, M. Karin, J. Feramisco, and M. Montminy: "Activation of cAMP and mitogen responsive genes relies on a common nuclear factor". *Nature* 370:226, 1994.). CBP in turn interacts with the basal transcription factor TFIIB causing increased transcription. CREB also has been reported to interact with dTAFII 110, a TATA binding protein-associated factor whose binding may regulate transcription (Ferreri, K., G. Gill, and M. Montminy: "The cAMP-regulated transcription factor CREB interacts with a component of the TFIID complex". *Proc. Natl. Acad. Sci. USA* 91:1210, 1994.). In addition to these interactions, CREB/ATF proteins can specifically bind multiple other nuclear factors (Hoeffler, J. P., J. W. Lustbader, and C.-Y. Chen: "Identification of multiple nuclear factors that interact with cyclic adenosine 3',5'-monophosphate response element-binding protein and activating transcription factor-2 by protein-protein interactions". *Mol. Endocrinol.* 5:256, 1991) but the biologic significance of most of these interactions is unknown. CREB is normally thought to bind DNA either as a homodimer or as a heterodimer with several other proteins. Surprisingly, CREB monomers constitutively activate transcription (Krajewski, W., and K. A. W. Lee: "A monomeric derivative of the cellular transcription factor CREB functions as a constitutive activator". *Mol. Cell. Biol.* 14:7204, 1994.).

Aside from their critical role in regulating cellular transcription, it has recently been shown that CREB/ATF proteins are subverted by some infectious viruses and retroviruses, which require them for viral replication. For example, the cytomegalovirus immediate early promoter, one of the strongest known mammalian promoters, contains eleven copies of the CRE which are essential for promoter function (Chang, Y.-N., S. Crawford, J. Stall, D. R. Rawlins, K.-T. Jeang, and G. S. Hayward: "The palindromic series I repeats in the simian cytomegalovirus major immediate-early promoter behave as both strong basal enhancers and cyclic AMP response elements". *J. Virol.* 64:264, 1990). At least some of the transcriptional activating effects of the adenovirus E1A protein, which induces many promoters, are due to its binding to the DNA binding domain of the CREB/ATF protein, ATF-2, which mediates E1A inducible transcription activation (Liu, F., and M. R. Green: "Promoter targeting by adenovirus E1a through interaction with different cellular DNA-binding domains". *Nature* 368:520, 1994). It has also been suggested that E1A binds to the CREB-binding protein, CBP (Arany, Z., W. R. Sellers, D. M. Livingston, and R. Eckner: "E1A-associated p300 and CREB-associated CBP belong to a conserved family of coactivators". *Cell* 77:799, 1994). Human T lymphotropic virus-I (HTLV-1), the retrovirus which causes human T cell leukemia and tropical spastic paresis, also requires CREB/ATF proteins for replication. In this case, the retrovirus produces a protein, Tax, which binds to CREB/ATF proteins and redirects them from their normal cellular binding sites to different DNA sequences (flanked by G- and C-rich sequences) present within the HTLV transcriptional enhancer (Paca-Uccaralertkun, S., L.-J. Zhao, N. Adya, J. V. Cross, B. R. Cullen, I. M. Boros, and C.-Z. Giam: "In vitro selection of DNA elements highly responsive to the human T-cell lymphotropic virus type I transcriptional activator, Tax". *Mol. Cell. Biol.* 14:456, 1994; Adya, N., L.-J. Zhao, W. Huang, I. Boros, and C.-Z. Giam: "Expansion of CREB's DNA recognition specificity by Tax results from interaction with Ala-Ala-Arg at positions 282-284 near the conserved DNA-binding domain of CREB". *Proc. Natl. Acad. Sci. USA* 91:5642, 1994).

SUMMARY OF THE INVENTION

The instant invention is based on the finding that certain nucleic acids containing unmethylated cytosine-guanine (CpG) dinucleotides activate lymphocytes in a subject and redirect a subject's immune response from a Th2 to a Th1 (e.g. by inducing monocytic cells and other cells to produce Th1 cytokines, including IL-12, IFN-γ and GM-CSF). Based on this finding, the invention features, in one aspect, novel immunostimulatory nucleic acid compositions.

In a preferred embodiment, the immunostimulatory nucleic acid contains a consensus mitogenic CpG motif represented by the formula:

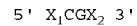

wherein $X_1$ is selected from the group consisting of A,G and T; and $X_2$ is C or T.

In a particularly preferred embodiment an immunostimulatory nucleic acid molecule contains a consensus mitogenic CpG motif represented by the formula:

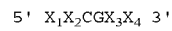

wherein C and G are unmethylated; and $X_1$, $X_2$, $X_3$ and $X_4$ are nucleotides.

Enhanced immunostimulatory activity of human cells occurs where $X_1X_2$ is selected from the group consisting of GpT, GpG, GpA and ApA and/or $X_3X_4$ is selected from the group consisting of TpT, CpT and GpT (Table 5). For facilitating uptake into cells, CpG containing immunostimulatory nucleic acid molecules are preferably in the range of 8 to 40 base pairs in size. However, nucleic acids of any size (even many kb long) are immunostimulatory if sufficient immunostimulatory motifs are present, since such larger nucleic acids are degraded into oligonucleotides inside of cells. Preferred synthetic oligonucleotides do not include a GCG trinucleotide sequence at or near the 5' and/or 3' terminals and/or the consensus mitogenic CpG motif is not a palindrome. Prolonged immunostimulation can be obtained using stabilized oligonucleotides, particularly phosphorothioate stabilized oligonucleotides.

In a second aspect, the invention features useful therapies, which are based on the immunostimulatory activity of the nucleic acid molecules. For example, the immunostimulatory nucleic acid molecules can be used to treat, prevent or ameliorate an immune system deficiency (e.g., a tumor or cancer or a viral, fungal, bacterial or parasitic infection in a subject). In addition, immunostimulatory nucleic acid molecules can be administered to stimulate a subject's response to a vaccine.

Further, by redirecting a subject's immune response from Th2 to Th1, the instant claimed nucleic acid molecules can be administered to treat or prevent the symptoms of asthma. In addition, the instant claimed nucleic acid molecules can be administered in conjunction with a particular allergen to a subject as a type of desensitization therapy to treat .or prevent the occurrence of an allergic reaction.

Further, the ability of immunostimulatory nucleic acid molecules to induce leukemic cells to enter the cell cycle supports the use of immunostimulatory nucleic acid molecules in treating leukemia by increasing the sensitivity of chronic leukemia cells and then administering conventional ablative chemotherapy, or combining the immunostimulatory nucleic acid molecules with another immunotherapy.

Other features and advantages of the invention will become more apparent from the following detailed description and claims.

BRIEF DESCRIPTION OF THE FIGURES

FIG. 1A-C are graphs plotting dose-dependent IL-6 production in response to various DNA sequences in T cell depleted spleen cell cultures. A. E. coli DNA (●) and calf thymus DNA (■) sequences and LPS (at 10× the concentration of E. coli and calf thymus DNA)(♦). B. Control phosphodiester oligodeoxynucleotide (ODN) 5'ATGGAAGGTC-CAGTGTTCTC3' (SEQ ID NO:1) (■) and two phosphodiester CpG ODN 5'ATCGACCTACGTGCGT-TCTC3' (SEQ ID NO:2) (♦) and 5'TCCATAACGTTCCT-GATGCT3' (SEQ ID NO:3) (●). C. Control phosphorothioate ODN 5'GCTAGATGTTAGCGT3' (SEQ ID NO:4) (■) and two phosphorothioate CpG ODN 5'GAGAACGTCGAC-CTTCGAT3' (SEQ ID NO:5) (♦) and 5'GCATGACGT-TGAGCT3' (SEQ ID NO:6) (●). Data present the mean±standard deviation of triplicates.

FIG. 4A is a graph plotting dose-dependent inhibition of CpG-induced IgM production by anti-IL-6. Splenic B-cells from DBA/2 mice were stimulated with CpG ODN 5'TCCAAGACGTTCCTGATGCT3' (SEQ ID NO:9) in the presence of the indicated concentrations of neutralizing anti-IL-6 (♦) or isotype control Ab (●) and IgM levels in culture supernatants determined by ELISA. In the absence of CpG ODN, the anti-IL-6 Ab had no effect on IgM secretion (■).

DETAILED DESCRIPTION OF THE INVENTION

Definitions

Figure 1A:
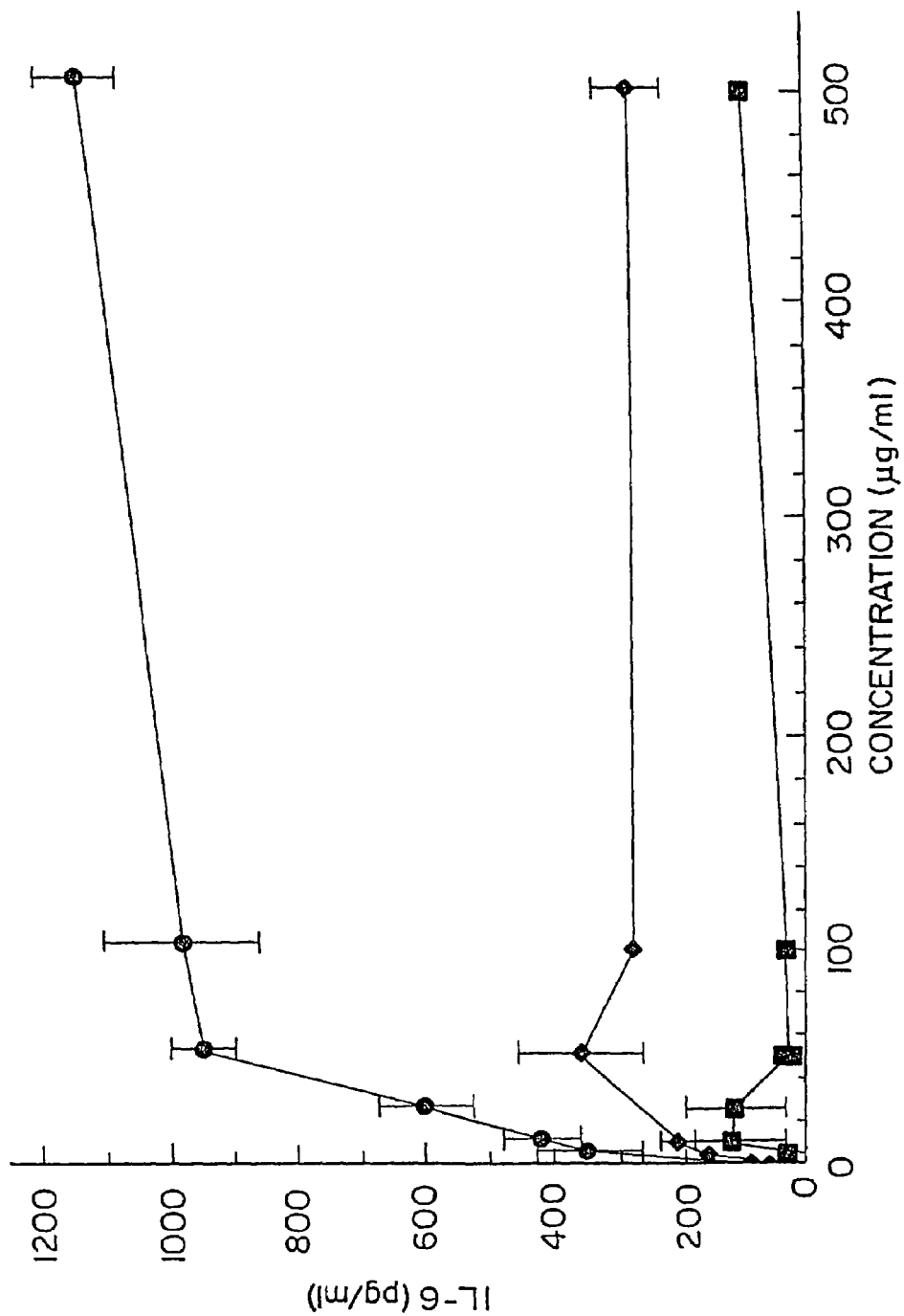

As used herein, the following terms and phrases shall have the meanings set forth below:

An "allergen" refers to a substance that can induce an allergic or asthmatic response in a susceptible subject. The list of allergens is enormous and can include pollens, insect venoms, animal dander, dust, fungal spores and drugs (e.g. penicillin). Examples of natural, animal and plant allergens include proteins specific to the following genera: *Canine (Canis familiaris); Dermatophagoides* (e.g. *Dermatophagoides farinae); Felis (Felis domesticus); Ambrosia (Ambrosia artemiisfolia; Lolium* (e.g. *Lolium perenne* or *Lolium multiflorum); Cryptomeria (Cryptomeria japonica); Alternaria (Alternaria alternata); Alder; Alnus (Alnus gultinosa); Betula (Betula verrucosa); Quercus (Quercus alba); Olea (Olea europa); Artemisia (Artemisia vulgaris); Plantago* (e.g. *Plantago lanceolata); Parietaria* (e.g. *Parietaria officinalis* or *Parietaria judaica); Blattella* (e.g. *Blattella germanica); Apis* (e.g. *Apis multiflorum); Cupressus* (e.g. *Cupressus sempervirens, Cupressus arizonica* and *Cupressus macrocarpa); Juniperus* (e.g. *Juniperus sabinoides, Juniperus virginiana, Juniperus communis* and *Juniperus ashei); Thuya* (e.g. *Thuya orientalis); Chamaecyparis* (e.g. *Chamaecyparis obtusa); Periplaneta* (e.g. *Periplaneta americana); Agropyron* (e.g. *Agropyron repens); Secale* (e.g. *Secale cereale); Triticum* (e.g. *Triticum aestivum); Dactylis* (e.g. *Dactylis glomerata); Festuca* (e.g. *Festuca elatior); Poa* (e.g. *Poa pratensis* or *Poa compressa); Avena* (e.g. *Avena sativa); Holcus* (e.g. *Holcus lanatus); Anthoxanthum* (e.g. *Anthoxanthum odoratum); Arrhenatherum* (e.g. *Arrhenatherum elatius); Agrostis* (e.g. *Agrostis alba); Phleum* (e.g. *Phleum pratense); Phalaris* (e.g. *Phalaris arundinacea); Paspalum* (e.g. *Paspalum notatum); Sorghum* (e.g. *Sorghum halepensis);* and *Bromus* (e.g. *Bromus inermis).*

An "allergy" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma"—refers to a disorder of the respiratory system characterized by inflammation, narrowing of the airways and increased reactivity of the airways to inhaled agents. Asthma is frequently, although not exclusively associated with atopic or allergic symptoms.

An "immune system deficiency" shall mean a disease or disorder in which the subject's immune system is not functioning in normal capacity or in which it would be useful to boost a subject's immune response for example to eliminate a tumor or cancer (e.g. tumors of the brain, lung (e.g. small cell and non-small cell), ovary, breast, prostate, colon, as well as other carcinomas and sarcomas) or an infection in a subject.

Examples of infectious virus include: *Retroviridae* (e.g., human immunodeficiency viruses, such as HIV-1 (also referred to as HTLV-III, LAV or HTLV-III/LAV, or HIV-III; and other isolates, such as HIV-LP; *Picornaviridae* (e.g., polio viruses, hepatitis A virus; enteroviruses, human coxsackie viruses, rhinoviruses, echoviruses); *Calciviridae* (e.g., strains that cause gastroenteritis); *Togaviridae* (e.g., equine encephalitis viruses, rubella viruses); *Flaviridae* (e.g., dengue viruses, encephalitis viruses, yellow fever viruses); *Coronaviridae* (e.g., coronaviruses); *Rhabdoviridae* (e.g., vesicular stomatitis viruses, rabies viruses); *Filoviridae* (e.g., ebola viruses); *Paramnyxoviridae* (e.g., parainfluenza viruses, mumps virus, measles virus, respiratory syncytial virus); *Orthomyxoviridae* (e.g., influenza viruses); *Bungaviridae* (e.g., Hantaan viruses, bunga viruses, phleboviruses and Nairo viruses); Arena viridae (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenoviridae* (most adenoviruses); *Herpesviridae* (herpes simpléx virus (HSV) 1 and 2, varicella zoster virus, cytomegalovirus (CMV), herpes viruses'); *Poxviridae* (variola viruses, vaccinia viruses, pox viruses); and *Iridoviridae* (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* spp. (e.g., *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic spp.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacte-* rium nucleatum, Streptobacillus moniliformis, Treponema pallidum, Treponema pertenue, Leptospira, and Actinomyces israeli.

Examples of infectious fungi include: Cryptococcus neoformans, Histoplasma capsulatum, Coccidioides immitis, Blastomyces dermatitidis, Chlamydia trachomatis, Candida albicans. Other infectious organisms (i.e., protists) include: Plasmodium falciparum and Toxoplasma gondii.

An "immunostimulatory nucleic acid molecule" refers to a nucleic acid molecule, which contains an unmethylated cytosine, guanine dinucleotide sequence. (i.e. "CpG DNA" or DNA containing a cytosine followed by guanosine and linked by a phosphate bond) and stimulates (e.g. has a mitogenic effect on, or induces or increases cytokine expression by) a vertebrate lymphocyte. An immunostimulatory nucleic acid molecule can be double-stranded or single-stranded. Generally, double-stranded molecules are more stable in vivo, while single-stranded molecules have increased immune activity.

In a preferred embodiment, the immunostimulatory nucleic acid contains a consensus mitogenic CpG motif represented by the formula:

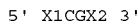

wherein $X_1$ is selected from the group consisting of A,G and T; and $X_2$ is C or T.

In a particularly preferred embodiment, immunostimulatory nucleic acid molecules are between 2 to 100 base pairs in size and contain a consensus mitogenic CpG motif represented by the formula:

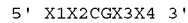

wherein C and G are unmethylated, $X_1$, $X_2$, $X_3$ and $X_4$ are nucleotides.

For economic reasons, preferably the immunostimulatory CpG DNA is in the range of between 8 to 40 base pairs in size if it is synthesized as an oligonucleotide. Alternatively, CpG dinucleotides can be produced on a large scale in plasmids, which after being administered to a subject are degraded into oligonucleotides. Preferred immunostimulatory nucleic acid molecules (e.g. for use in increasing the effectiveness of a vaccine or to treat an immune system deficiency by stimulating an antibody [humoral] response in a subject) have a relatively high stimulation index with regard to B cell, monocyte and/or natural killer cell responses (e.g. cytokine, proliferative, lytic or other responses).

The stimulation index of a particular immunostimulatory CpG DNA can be tested in various immune cell assays. Preferably, the stimulation index of the immunostimulatory CpG DNA with regard to B-cell proliferation is at least about 5, preferably at least about 10, more preferably at least about 15 and most preferably at least about 20 as determined by incorporation of $^3$H uridine in a murine B cell culture, which has been contacted with a 2 µM of ODN for 20 h at 37° C. and has been pulsed with 1 µCi of $^3$H uridine; and harvested and counted 4h later as described in detail in Example 1. For use in vivo, for example to treat an immune system deficiency by stimulating a cell-mediated (local) immune response in a subject, it is important that the immunostimulatory CpG DNA be capable of effectively inducing cytokine secretion by monocytic cells and/or Natural Killer (NK) cell lytic activity.

Preferred immunostimulatory CpG nucleic acids should effect at least about 500 pg/ml of TNF-α, 15 pg/ml IFN-γ, 70 pg/ml of GM-CSF 275 pg/ml of IL-6, 200 pg/ml IL-12, depending on the therapeutic indication, as determined by the assays described in Example 12. Other preferred immunostimulatory CpG DNAs should effect at least about 10%, more preferably at least about 15% and most preferably at least about 20% YAC-1 cell specific lysis or at least about 30, more preferably at least about 35 and most preferably at least about 40% 2C11 cell specific lysis as determined by the assay described in detail in Example 4.

A "nucleic acid" or "DNA" shall mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the term refers to ribonucleotides as well as oligodeoxyribonucleotides. The term shall also include polynucleosides (i.e. a polynucleotide minus the phosphate) and any other organic base containing polymer. Nucleic acid molecules can be obtained from existing nucleic acid sources (e.g. genomic or cDNA), but are preferably synthetic (e.g. produced by oligonucleotide synthesis).

A "nucleic acid delivery complex" shall mean nucleic acid molecule associated with (e.g. ionically or covalently bound to; or encapsulated within) a targeting means (e.g. a molecule that results in higher affinity binding to target cell (e.g. B-cell and natural killer (NK) cell) surfaces and/or increased cellular uptake by target cells). Examples of nucleic acid delivery complexes include nucleic acids associated with: a sterol (e.g. cholesterol), a lipid (e.g. a cationic lipid, virosome or liposome), or a target cell specific binding agent (e.g. a ligand recognized by target cell specific receptor). Preferred complexes must be sufficiently stable in vivo to prevent significant uncoupling prior to internalization by the target cell. However, the complex should be cleavable under appropriate conditions within the cell so that the nucleic acid is released in a functional form.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double stranded structures.

A "stabilized nucleic acid molecule" shall mean a nucleic acid molecule that is relatively resistant to in vivo degradation (e.g. via an exo- or endo-nuclease). Stabilization can be a function of length or secondary structure. Unmethylated CpG containing nucleic acid molecules that are tens to hundreds of kbs long are relatively resistant to in vivo degradation. For shorter immunostimulatory nucleic acid molecules, secondary structure can stabilize and increase their effect. For example, if the 3' end of a nucleic acid molecule has self-complementarity to an upstream region, so that it can fold back and form a sort of stem loop sturcture, then the nucleic acid molecule becomes stabilized and therefore exhibits more activity.

Preferred stabilized nucleic acid molecules of the instant invention have a modified backbone. For use in immune stimulation, especially preferred stabilized nucleic acid molecules are phosphorothioate modified nucleic acid molecules (i.e. at least one of the phosphate oxygens of the nucleic acid molecule is replaced by sulfur). Preferably the phosphate modification occurs at or near the 5' and/or 3' end of the nucleic acid molecule. In addition to stabilizing nucleic acid molecules, as reported further herein, phosphorothioate-modified nucleic acid molecules (including phosphorodithioate-modified) can increase the extent of immune stimulation of the nucleic acid molecule, which contains an unmethylated CpG dinucleotide as shown herein. International Patent Application Publication Number: WO 95/26204 entitled "immune Stimulation By Phosphorothioate Oligonucleotide Analogs" also reports on the non-sequence specific immunostimulatory effect of phosphorothioate modified oligonucleotides. As reported herein, unmethylated CpG containing nucleic acid molecules having a phosphorothioate backbone have been found to preferentially activate B-cell activity, while unmethylated CpG containing nucleic acid molecules having a phosphodiester backbone have been found to preferentially activate monocytic (macrophages, dendritic cells and monocytes) and NK cells. Phosphorothioate CpG oligonucleotides with preferred human motifs are also strong activators of monocytic and NK cells.

Other stabilized nucleic acid molecules include: nonionic DNA analogs, such as alkyl- and aryl-phosphonates (in which the charged phosphonate oxygen is replaced by an alkyl or aryl group), phosphodiester and alkyphosphotriesters, in which the charged oxygen moiety is alkylated. Nucleic acid molecules which contain a diol, such as tetraethyleneglycol or hexaethyleneglycol, at either or both termini have also been shown to be substantially resistant to nuclease degradation.

A "subject" shall mean a human or vertebrate animal including a dog, cat, horse, cow, pig, sheep, goat, chicken, monkey, rat, mouse, etc.

As used herein, the term "vector" refers to a nucleic acid molecule capable of transporting another nucleic acid to which it has been linked. Preferred vectors are those capable of autonomous replication and expression of nucleic acids to which they are linked (e.g., an episome). Vectors capable of directing the expression of genes to which they are operatively linked are referred to herein as "expression vectors." In general, expression vectors of utility in recombinant DNA techniques are often in the form of "plasmids" which refer genre rally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Certain Unmethylated CpG Containing Nucleic Acids have B Cell Stimulatory Activity As Shown In vitro and In vivo In the course of investigating the lymphocyte stimulatory effects of two antisense oligonucleotides specific for endogenous retroviral sequences, using protocols described in the attached Examples 1 and 2, it was surprisingly found that two out of twenty-four "controls" (including various scrambled, sense, and mismatch controls for a panel of "antisense" ODN) also mnediated B cell activation and IgM secretion, while the other "controls" had no effect.

Two observations suggested that the mechanism of this B cell activation by the "control" ODN may not involve antisense effects 1) comparison of vertebrate DNA sequences listed in GenBank showed no greater homology than that seen with non-stimulatory ODN and 2) the two controls showed no hybridization to Northern blots with 10 µg of spleen poly A+RNA. Resynthesis of these ODN on a different synthesizer or extensive purification by polyacrylamide gel electrophoresis or high pressure liquid chromatography gave identical stimulation, eliminating the possibility of an impurity. Similar stimulation was seen using B cells from C3H/HeJ mice, eliminating the possibility that lipopolysaccharide (LPS) contamination could account for the results.

The fact that two "control" ODN caused B cell activation similar to that of the two "antisense" ODN raised the possibility that all four ODN were stimulating B cells through some non-antisense mechanism involving a sequence motif that was absent in all of the other nonstimulatory control ODN. In comparing these sequences, it was discovered that all of the four stimulatory ODN contained CpG dinucleotides that were in a different sequence context from the nonstimulatory control.

To determine whether the CpG motif present in the stimulatory ODN was responsible for the observed stimulation, over 300 ODN ranging in length from 5 to 42 bases that contained methylated, unmethylated, or no CpG dinucleotides in various sequence contexts were synthesized. These ODNs, including the two original "controls" (ODN 1 and 2) and two originally synthesized as "antisense" (ODN 3D and 3M; Krieg, A. M. J. Immunol. 143:2448 (1989)), were then examined for in vitro effects on spleen cells (representative sequences are listed in Table 1). Several ODN that contained CpG dinucleotides induced B cell activation and IgM secretion; the magnitude of this stimulation typically could be increased by adding more CpG dinucleotides (Table 1; compare ODN 2 to 2a or 3D to 3Da and 3Db). Stimulation did not appear to result from an antisense mechanism or impurity. ODN caused no detectable proliferation of γδ or other T cell populations.

Mitogenic ODN sequences uniformly became nonstimulatory if the CpG dinucleotide was mutated (Table 1; compare ODN 1 to 1a; 3D to 3Dc; 3M to 3Ma; and 4 to 4a) or if the cytosine of the CpG dinucleotide was replaced by 5-methylcytosine (Table 1; ODN 1b, 2b, 3Dd, and 3Mb). Partial methylation of CpG motifs caused a partial loss of stimulatory effect (compare 2a to 2c, Table 1). In contrast, methylation of other cytosines did not reduce ODN activity (ODN 1c, 2d, 3De and 3Mc). These data confirmed that a CpG motif is the essential element present in ODN that activate B cells.

In the course of these studies, it became clear that the bases flanking the CpG dinucleotide played an important role in determining the murine B cell activation induced by an ODN. The optimal stimulatory motif was determined to consist of a CpG flanked by two 5' purines (preferably a GpA dinucleotide) and two 3' pyrimidines (preferably a TpT or TpC dinucleotide). Mutations of ODN to bring the CpG motif closer to this ideal improved stimulation (e.g. Table 1, compare ODN 2 to 2e; 3M to 3Md) while mutations that disturbed the motif reduced stimulation (e.g. Table 1, compare ODN 3D to 3Df; 4 to 4b, 4c and 4d). On the other hand, mutations outside the CpG motif did not reduce stimulation (e.g. Table 1, compare ODN 1 to 1d; 3D to 3Dg; 3M to 3Me). For activation of human cells, the best flanking bases are slightly different (See Table 5).

Of those tested, ODNs shorter than 8 bases were nonstimulatory (e.g. Table 1, ODN 4e). Among the forty-eight 8 base ODN tested, the most stimulatory sequence identified was TCAACGTT (ODN 4) which contains the self complementary "palindrome" AACGTT. In further optimizing this motif, it was found that ODN containing Gs at both ends showed increased stimulation, particularly if the ODN were rendered nuclease resistant by phosphorothioate modification of the terminal internucleotide linkages. ODN 1585 (5'GGGGTCAACGTTGAGGGGGG3' (SEQ ID NO:12)), in which the first two and last five internucleotide linkages are phosphorothioate modified caused an average 25.4 fold increase in mouse spleen cell proliferation compared to an average 3.2 fold increase in proliferation induced by ODN 1638, which has the same sequence as ODN 1585 except that the 10 Gs at the two ends are replaced by 10 As. The effect of the G-rich ends is cis; addition of an ODN with poly G ends but no CpG motif to cells along with 1638 gave no increased proliferation. For nucleic acid molecules longer than 8 base pairs, non-palindromic motifs containing an unmethylated CpG were found to be more immunostimulatory.

Other octamer ODN containing a 6 base palindrome with a TpC dinucleotide at the 5' end were also active (e.g. Table 1, ODN 4b, 4c). Other dinucleotides at the 5' end gave reduced stimulation (e.g. ODN 4f; all sixteen possible dinucleotide were tested). The presence of a 3' dinucleotide was insufficient to compensate for the lack of a 5' dinucleotide (e.g. Table 1, ODN 4g). Disruption of the palindrome eliminated stimulation in octamer ODN (e.g. Table 1, ODN 4h), but palindromes were not required in longer ODN.

TABLE 1

Oligonucleotide Stimulation of Mouse B Cells

| ODN | | | Stimulation Index' | |
|---|---|---|---|---|
| | Production | Sequence (5' to 3')† | $^3$H Uridine | IgM |
| 1 | (SEQ ID NO:13) | GCTAGACGTTAGCGT | 6.1 ± 0.8 | 17.9 ± 3.6 |
| 1a | (SEQ ID NO:4) | ......T........ | 1.2 ± 0.2 | 1.7 ± 0.5 |
| 1b | (SEQ ID NO:14) | ......Z........ | 1.2 ± 0.1 | 1.8 ± 0.0 |
| 1c | (SEQ ID NO:15) | ..........Z.. | 10.3 ± 4.4 | 9.5 ± 1.8 |
| 1d | (SEQ ID NO:16) | ..AT......GAGC. | 13.0 ± 2.3 | 18.3 ± 7.5 |
| 2 | (SEQ ID NO:17) | ATGGAAGGTCCAGCGTTCTC | 2.9 ± 0.2 | 13.6 ± 2.0 |
| 2a | (SEQ ID NO:18) | ..C..CTC..G........ | 7.7 ± 0.8 | 24.2 ± 3.2 |
| 2b | (SEQ ID NO:19) | ..Z..CTC.ZG..Z...... | 1.6 ± 0.5 | 2.8 ± 2.2 |
| 2c | (SEQ ID NO:20) | ..Z..CTC..G........ | 3.1 ± 0.6 | 7.3 ± 1.4 |
| 2d | (SEQ ID NO:21) | ..C..CTC..G....Z.. | 7.4 ± 1.4 | 27.7 ± 5.4 |
| 2e | (SEQ ID NO:22) | ............A...... | 5.6 ± 2.0 | ND |
| 3D | (SEQ ID NO:23) | GAGAACGCTGGACCTTCCAT | 4.9 ± 0.5 | 19.9 ± 3.6 |
| 3Da | (SEQ ID NO:24) | ........C......... | 6.6 ± 1.5 | 33.9 ± 6.8 |
| 3Db | (SEQ ID NO:25) | ........C......G.. | 10.1 ± 2.8 | 25.4 ± 0.8 |
| 3Dc | (SEQ ID NO:26) | ...C.A............ | 1.0 ± 0.1 | 1.2 ± 0.5 |
| 3Dd | (SEQ ID NO:27) | .....Z............ | 1.2 ± 0.2 | 1.0 ± 0.4 |
| 3De | (SEQ ID NO:28) | ............Z...... | 4.4 ± 1.2 | 18.8 ± 4.4 |
| 3Df | (SEQ ID NO:29) | ......A............ | 1.6 ± 0.1 | 7.7 ± 0.4 |
| 3Dg | (SEQ ID NO:30) | ........CC.G.ACTG.. | 6.1 ± 1.5 | 18.6 ± 1.5 |
| 3M | (SEQ ID NO:31) | TCCATGTCGGTCCTGATGCT | 4.1 ± 0.2 | 23.2 ± 4.9 |
| 3Ma | (SEQ ID NO:32) | ......CT............ | 0.9 ± 0.1 | 1.8 ± 0.5 |
| 3Mb | (SEQ ID NO:33) | .......Z............ | 1.3 ± 0.3 | 1.5 ± 0.6 |
| 3Mc | (SEQ ID NO:34) | ..........Z........ | 5.4 ± 1.5 | 8.5 ± 2.6 |
| 3Md | (SEQ ID NO:35) | ......A...T.......... | 17.2 ± 9.4 | ND |
| 3Me | (SEQ ID NO:36) | ..............C..A. | 3.6 ± 0.2 | 14.2 ± 5.2 |
| 4 | | TCAACGTT | 6.1 ± 1.4 | 19.2 ± 5.2 |
| 4a | | ....GC.. | 1.1 ± 0.2 | 1.5 ± 1.1 |
| 4b | | ...GCGC. | 4.5 ± 0.2 | 9.6 ± 3.4 |
| 4c | | ...TCGA. | 2.7 ± 1.0 | ND |
| 4d | | ..TT..AA | 1.3 ± 0.2 | ND |
| 4e | | -....... | 1.3 ± 0.2 | 1.1 ± 0.5 |
| 4f | | C....... | 3.9 ± 1.4 | ND |

TABLE 1-continued

Oligonucleotide Stimulation of Mouse B Cells

| ODN Production | Sequence (5' to 3')† | Stimulation Index' $^3$H Uridine | IgM |
|---|---|---|---|
| 4g | --...._.._..CT | 1.4 ± 0.3 | ND |
| 4h | ......_.._.C | 1.2 ± 0.2 | ND |
| LPS | | 7.8 ± 2.5 | 4.8 ± 1.0 |

'Stimulation indexes are the means and std. dev. derived from at least 3 separate experiments, and are compared to wells cultured with no added ODN.
ND = not done.
CpG dinucleotides are underlined.
Dots indicate identity; dashes indicate deletions.
Z indicates 5 methyl cytosine.

TABLE 2

Identification of the optimal CpG motif for Murine IL-6 production and B cell activation.

| ODN | SEQUENCE (5'-3') | IL-6 (pg/ml)$^a$ CH12.LX | SPLENIC B CELL | SI$^b$ | IgM (ng/ml)$^c$ |
|---|---|---|---|---|---|
| 512 (SEQ ID NO:37) | TCCATGTCGGTCCTGATGCT | 1300 ± 106 | 627 ± 43 | 5.8 ± 0.3 | 7315 ± 1324 |
| 1637 (SEQ ID NO:38) | ......C............ | 136 ± 27 | 46 ± 6 | 1.7 ± 0.2 | 770 ± 72 |
| 1615 (SEQ ID NO:39) | ......G............ | 1201 ± 155 | 850 ± 202 | 3.7 ± 0.3 | 3212 ± 617 |
| 1614 (SEQ ID NO:40) | ......A............ | 1533 ± 321 | 1812 ± 103 | 10.8 ± 0.6 | 7558 ± 414 |
| 1636 (SEQ ID NO:41) | ........A.......... | 1181 ± 76 | 947 ± 132 | 5.4 ± 0.4 | 3983 ± 485 |
| 1634 (SEQ ID NO:42) | ........C.......... | 1049 ± 223 | 1671 ± 175 | 9.2 ± 0.9 | 6256 ± 261 |
| 1619 (SEQ ID NO:43) | ........T.......... | 1555 ± 304 | 2908 ± 129 | 12.5 ± 1.0 | 8243 ± 698 |
| 1618 (SEQ ID NO:44) | ......A..T......... | 2109 ± 291 | 2596 ± 166 | 12.9 ± 0.7 | 10425 ± 674 |
| 1639 (SEQ ID NO:45) | .....AA..T......... | 1827 ± 83 | 2012 ± 132 | 11.5 ± 0.4 | 9489 ± 103 |
| 1707 (SEQ ID NO:46) | ......A..TC........ | ND | 1147 ± 175 | 4.0 ± 0.2 | 3534 ± 217 |
| 1708 (SEQ ID NO:47) | .....CA..TG........ | ND | 59 ± 3 | 1.5 ± 0.1 | 466 ± 109 |

Dots indicate identity; CpG dinucleotides are underlined; ND = not done
$^a$The experiment was done at least three times with similar results. The level of IL-6 of unstimulated control cultures of both CH12.LX and splenic B cells was ≦10 pg/ml. The IgM level of unstimulated culture was 547 ± 82 ng/ml. CpG dinucleotides are underlined and dots indicate identity.
$^b$[$^3$H] Uridine uptake was indicated as a fold increase (SI: stimulation index) from unstimulated control (2322.67 ± 213.68 cpm). Cells were stimulated with 20 μM of various CpG O-ODN. Data present the mean ± SD of triplicates
$^c$Measured by ELISA.

The kinetics of lymphocyte activation were investigated using mouse spleen cells. When the cells were pulsed at the same time as ODN addition and harvested just four hours later, there was already a two-fold increase in $^3$H uridine incorporation. Stimulation peaked at 12-48 hours and then decreased. After 24 hours, no intact ODN were detected, perhaps accounting for the subsequent fall in stimulation when purified B cells with or without anti-IgM (at a submitogenic dose) were cultured with CpG ODN, proliferation was found to synergistically increase about 10-fold by the two mitogens in combination after 48 hours. The magnitude of stimulation was concentration dependent and consistently exceeded that of LPS under optimal conditions for both. Oligonucleotides containing a nuclease resistant phosphorothioate backbone were approximately two hundred times more potent than unmodified oligonucleotides.

Cell cycle analysis was used to determine the proportion of B cells activated by CpG-ODN. CpG-ODN induced cycling in more than 95% of B cells. Splenic B lymphocytes sorted by flow cytometry into CD23−(marginal zone) and CD23+(follicular) subpopulations were equally responsive to ODN-induced stimulation, as were both resting and activated populations of B cells isolated by fractionation over Percoll gradients. These studies demonstrated that CpG-ODN induce essentially all B cells to enter the cell cycle.

Immunostimulatory Nucleic Acid Molecules Block Murine B Cell Apoptosis

Certain B cell lines such as WEHI-231 are induced to undergo growth arrest and/or apoptosis in response to crosslinking of their antigen receptor by anti-IgM (Jakway, J .P. et al., "Growth regulation of the B lymphoma cell line WEHI-231 by anti-immunoglobulin, lipopolysaccharide and other bacterial products" *J. Immunol.* 137: 2225 (1986); Tsubata, T., J. Wu and T. Honjo: B-cell apoptosis induced by antigen receptor crosslinking is blocked by a T-cell signal through CD40." *Nature* 364: 645 (993)). WEHI-231 cells are rescued from this growth arrest by certain stimuli such as LPS and by the CD40 ligand. ODN containing the CpG motif were also found to protect WEHI-231 from anti-IgM induced growth arrest, indicating that accessory cell populations are not required for the effect. Subsequent work indicates that CpG ODN induce Bcl-x and myc expression, which may account for the protection from apoptosis. Also, CpG nucleic acids have been found to block apoptosis in human cells. This inhibition of apoptosis is important, since it should enhance and prolong immune activation by CpG DNA.

shown in Table 3, IL-6 production was markedly increased in cells cultured with *E. coli* DNA but not in cells cultured with calf thymus DNA. To confirm that the increased IL-6 production observed with *E. coli* DNA was not due to contamination by other bacterial products, the DNA was digested with DNAse prior to analysis. DNAse pretreatment abolished IL-6 production induced by *E. coli* DNA (Table 3). In addition, spleen cells from LPS-nonrespbnseive C3H/HeJ mouse produced similar levels of IL-6 in response to bacterial DNA. To analyze whether the IL-6 secretion induced by *E. coli* DNA was mediated by the unmethylated CpG dinucleotides in bacterial DNA, methylated *E. coli* DNA and a panel of synthetic ODN were examined. As shown in Table 3, CpG ODN significantly induced IL-6 secretion (ODN 5a, 5b, 5c) while CpG methylated *E. coli* DNA, or ODN containing methylated CpG (ODN 5f) or no CpG (ODN 5d) did not. Changes at sites other than CpG dinucleotides (ODN 5b) or methylation of other cytosines (ODN 5g) did not reduce the effect of CpG ODN. Methylation of a single CpG in an ODN with three CpGs resulted in a partial reduction in the stimulation (compare ODN 5c to 5e; Table 3).

TABLE 3

Induction of Murine IL-6 secretion by CpG motifs in bacterial DNA or oligonucleotides.

| Treatment | | | | IL-6 (pg/ml) |
|---|---|---|---|---|
| calf thymus DNA | | | | ≦10 |
| calf thymus DNA + DNase | | | | ≦10 |
| E. coli DNA | | | | 1169.5 ± 94.1 |
| E. coli DNA + DNase | | | | ≦10 |
| CpG methylated E. coli DNA | | | | ≦10 |
| LPS | | | | 280.1 ± 17.1 |
| Media (no DNA) | | | | ≦10 |
| ODN 5a | SEQ ID NO:1 | ATGGACTCTCCAGCGTTCTC | | 1096.4 ± 372.0 |
| 5b | SEQ ID NO:2 | .....AGG....A........ | | 1124.5 ± 126.2 |
| 5c | SEQ ID NO:3 | ..C.......G.......... | | 1783.0 ± 189.5 |
| 5d | SEQ ID NO:4 | .....AGG...C..T...... | | ≦10 |
| 5e | SEQ ID NO:5 | ..C.......G..Z....... | | 851.1 ± 114.4 |
| 5f | SEQ ID NO:6 | ..Z......ZG..Z....... | | ≦10 |
| 5g | SEQ ID NO:7 | ..C.......G......Z.. | | 1862.3 ± 87.26 |

T cell depleted spleen cells from DBA/2 mice were stimulated with phosphodiester modified oligonucleotides (O-ODN) (20 µM), calf thymus DNA (50 µg/ml) or E. coli DNA (50 µg/ml) with or without enzyme treatment, or LPS (10 µg/ml) for 24 hr.
Data represent the mean (pg/ml) ± SD of triplicates.
CpG dinucleotides are underlined and dots indicate identity.
Z indicates 5-methylcytosine.

Induction of Murine Cytokine Secretion by CpG Motifs in Bacterial DNA or Oligonucleotides.

As described in Example 9, the amount of IL-6 secreted by spleen cells after CpG DNA stimulation was measured by ELISA. T cell depleted spleen cell cultures rather than whole spleen cells were used for in vitro studies following preliminary studies showing that T cells contribute little or nothing to the IL-6 produced by CpG DNA-stimulated spleen cells. As Identification of the Optimal CpG Motif for Induction of Murine IL-6 and IgM Secretion and B Cell Proliferation.

To evaluate whether the optimal B cell stimulatory CpG motif was identical with the optimal CpG motif for IL-6 secretion, a panel of ODN in which the bases flanking the CpG dinucleotide were progressively substituted was studied. This ODN panel was analyzed for effects on B cell proliferation, Ig production, and IL-6 secretion, using both splenic B cells and CH12.LX cells. As shown in Table 2, the optimal stimulatory motif is composed of an unmethylated CpG flanked by two 5' purines and two 3' pyrimidines. Generally a mutation of either 5' purine to pyrimidine or 3' pyrimidine to purine significantly reduced its effects. Changes in 5' purines to C were especially deleterious, but changes in 5' purines to T or 3' pyrimidines to purines had less marked effects. Based on analyses of these and scores of other ODN, it was determined that the optimal CpG motif for induction of IL-6 secretion is TGACGTT, which is identical with the optimal mitogenic and IgM-inducing CpG motif (Table 2). This motif was more stimulatory than any of the palindrome containing sequences studied (1639, 1707 and 1708).

Titration of Induction of Murine IL-6 Secretion by CpG Motifs.

Figure 1C:
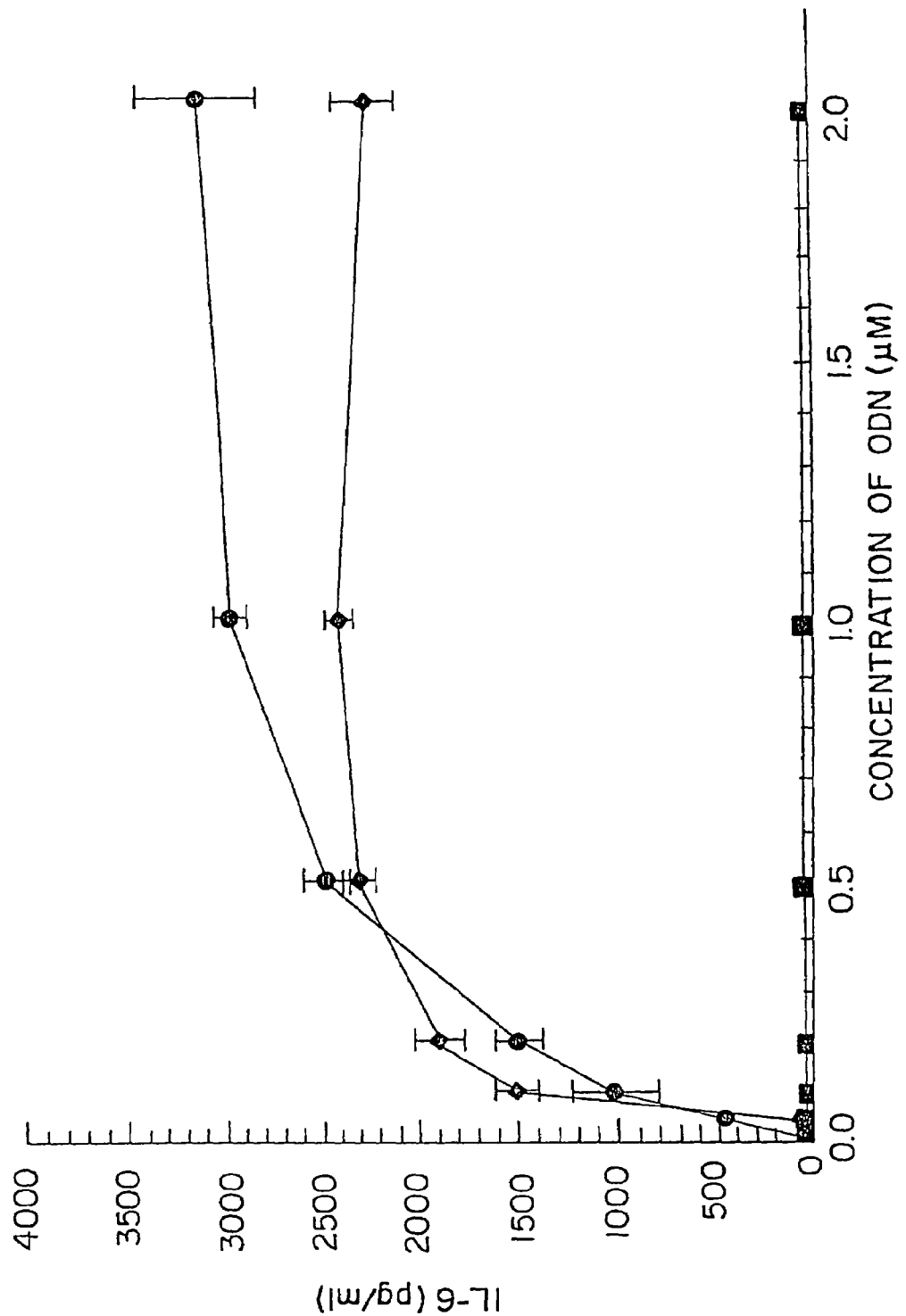

Bacterial DNA and CpG ODN induced IL-6 production in T cell depleted murine spleen cells in a dose-dependent manner, but vertebrate DNA and non-CpG ODN did not (FIG. 1). IL-6 production plateaued at approximately 50 µg/ml of bacterial DNA or 40 µM of CpG O-ODN. The maximum levels of IL-6 induced by bacterial DNA and CpG ODN were 1-1.5 ng/ml and 2-4 ng/ml respectively. These levels were significantly greater, than those seen after stimulation by LPS (0.35 ng/ml) (FIG. 1A). To evaluate whether CpG ODN with a nuclease-resistant DNA backbone would also induce IL-6 production, S-ODN were added to T cell depleted murine spleen cells. CpG S-ODN also induced IL-6 production in a dose-dependent manner to approximately the same level as CpG O-ODN while non-CpG S-ODN failed to induce IL-6 (FIG. 1C). CpG S-ODN at a concentration of 0.05 µM could induce maximal IL-6 production in these cells. This result indicated that the nuclease-resistant DNA backbone modification retains the sequence specific ability of CpG DNA to induce IL-6 secretion and that CpG S-ODN are more than 80-fold more potent than CpG O-ODN in this assay system.

Induction of Murine IL-6 Secretion by CpG DNA In vivo.

To evaluate the ability of bacterial DNA and CpG S-ODN to induce IL-6 secretion in vivo, BALB/c mice were injected iv. with 100 µg of E. coli DNA, calf thymus DNA, or CpG or non-stimulatory S-ODN and bled 2 hr after stimulation. The level of IL-6 the sera from the E. coli DNA injected group was approximately 13 ng/ml while IL-6 was not detected in the sera from calf thymus DNA or PBS injected groups (Table 4). CpG S-ODN also induced IL-6 secretion in vivo. The IL-6 level in the sera from CpG S-ODN injected groups was approximately 20 ng/ml. In contrast, IL-6 was not detected in the sera from non-stimulatory S-ODN stimulated group (Table 4).

TABLE 4

Secretion of Murine IL-6 induced by CpG DNA stimulation in vivo.

| Stimulant | IL-6 (pg/ml) |
| --- | --- |
| PBS | <50 |
| E. coli DNA | 13858 ± 3143 |
| Calf Thymus DNA | <50 |
| CpG S-ODN | 20715 ± 606 |
| non-CpG S-ODN | <50 |

Mice (2 mice/group) were i.v. injected with 100 µl of PBS, 200 µg of E. coli DNA or calf thymus DNA, or 500 µg of CpG S-ODN or non-CpG control S-ODN. Mice were bled 2 hr after injection and 1:10 dilution of each serum was analyzed by IL-6 ELISA. Sensitivity limit of IL-6 ELISA was 5 pg/ml. Sequences of the CpG S-ODN is 5'GCATGACGT-TGAGCT3' (SEQ ID NO:48) and of the non-stimulatory S-ODN is 5'GCTAGATGTTAGCGT3' (SEQ ID NO:49). Note that although there is a CpG in sequence 48, it is too close to the 3' end to effect stimulation, as explained herein. Data represent mean±SD of duplicates. The experiment was done at least twice with similar results.

Kinetics of Murine IL-6 Secretion After Stimulation by CpG Motifs In vivo.

Figure 2:
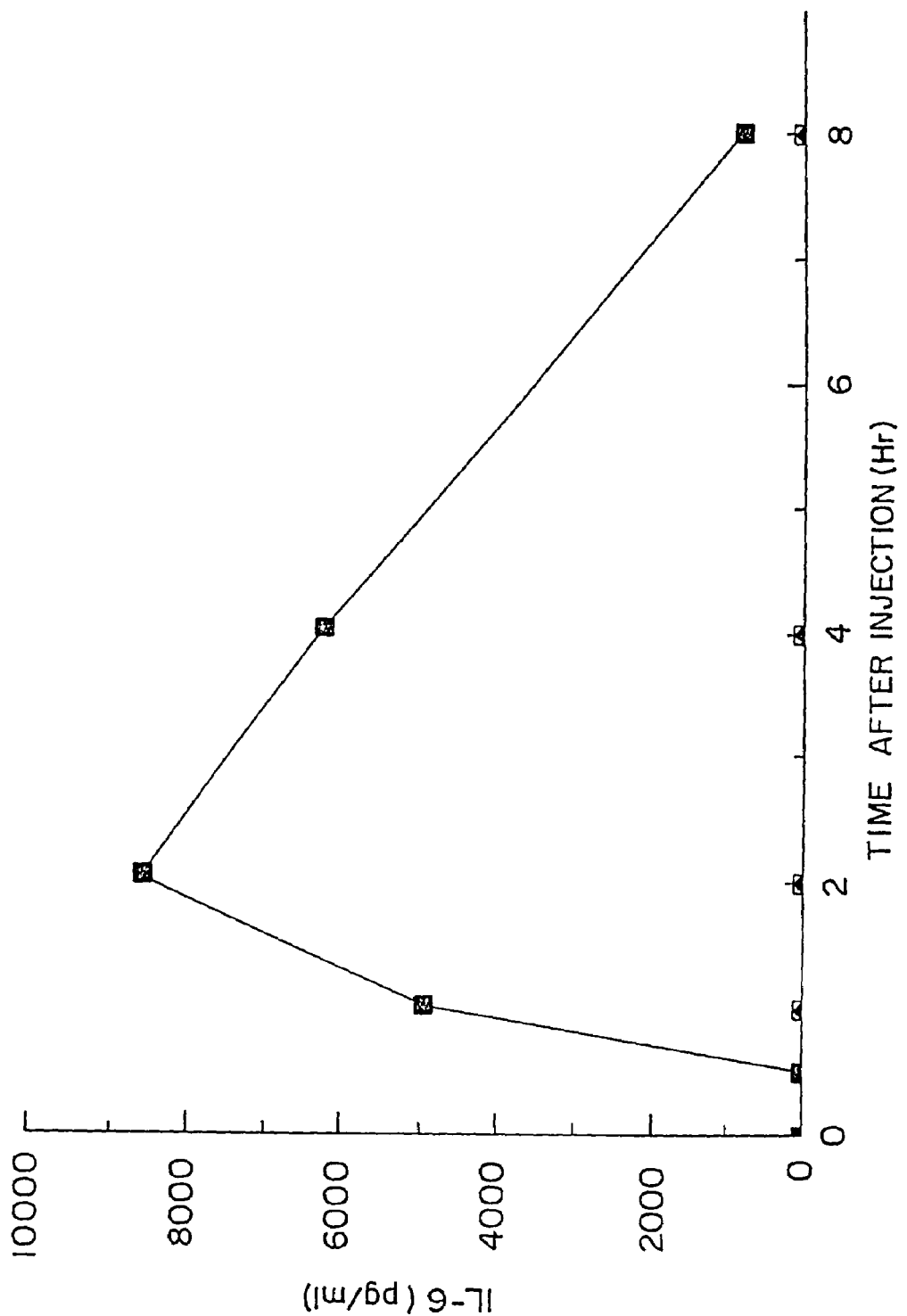
FIG. 2 is a graph plotting IL-6 production induced by CpG DNA in vivo as determined 1-8 hrs after injection. Data represent the mean from duplicate analyses of sera from two mice. BALB/c mice (two mice/group) were injected iv. with 100 µl of PBS (□) or 200 µg of CpG phosphorothioate ODN 5' TCCATGACGTTCCTGATGCT 3' (SEQ ID NO:7) (■) or non-CpG phosphorothioate ODN 5' TCCATGAGCTTCCT-GAGTCT 3' (SEQ ID NO:8) (♦).

To evaluate the kinetics of induction of IL-6 secretion by CpG DNA in vivo, BALB/c mice were injected iv. with CpG or control non-CpG S-ODN. Serum L-6 levels were significantly increased within 1 hr and peaked at 2 hr to a level of approximately 9 ng/ml in the CpG S-ODN injected group (FIG. 2). IL-6 protein in sera rapidly decreased after 4 hr and returned to basal level by 12 hr after stimulation. In contrast to CpG DNA stimulated groups, no significant increase of IL-6 was observed in the sera from the non-stimulatory S-ODN or PBS injected groups (FIG. 2).

Tissue Distribution and Kinetics of IL-6 mRNA Expression Induced by CpG Motifs In vivo.

As shown in FIG. 2, the level of serum IL-6 increased rapidly after CpG DNA stimulation. To investigate the possible tissue origin of his serum IL-6, and the kinetics of IL-6 gene expression in vivo after CpG DNA stimulation, BALB/c mice were injected iv with CpG or non-CpG S-ODN and RNA was extracted from liver, spleen, thymus, and bone marrow at various time points after stimulation. As shown in FIG. 3A, the level of IL-6 mRNA in liver, spleen, and thymus was increased within 30 min. after injection of CpG S-ODN. The liver IL-6 mRNA peaked at 2 hr post-injection and rapidly decreased and reached basal level 8 hr after stimulation (FIG. 3A). Splenic IL-6 mRNA peaked at 2 hr after stimulation and then gradually decreased (FIG. 3A). Thymus IL-6 mRNA peaked at 1 hr post-injection and then gradually decreased (FIG. 3A). EL-6 mRNA was significantly increased in bone marrow within 1 hr after CpG S-ODN injection but then returned to basal level. In response to CpG S-ODN, liver, spleen and thymus showed more substantial increases in IL-6 mRNA expression than the bone marrow.

Patterns of Murine Cytokine Expression Induced by CpG DNA

In vivo or in whole spleen cells, no significant increase in the protein levels of the following interleukins: IL-2, IL-3, IL-4, IL-5, or IL-10 was detected within the first six hours (Klinman, D. M. et al., (1996) Proc. Natl. Acad. Sci. USA 93:2879-2883). However, the level of TNF-α is increased within 30 minutes and the level of IL-6 increased strikingly within 2 hours in the serum of mice injected with CpG ODN. Increased expression of IL-12 and interferon gamma (IFN-γ) mRNA by spleen cells was also detected within the first two hours.

TABLE 5

Induction of human PBMC cytokine secretion by CpG oligos

| ODN | Sequence (5'-3') | IL-6[1] | TNF-α[1] | IFN-γ[1] | GM-CSF | IL-12 |
|---|---|---|---|---|---|---|
| 512 SEQ ID NO:37 | TCCATGTCGGTCCTGATGCT | 500 | 140 | 15.6 | 70 | 250 |
| 1637 SEQ ID NO:38 | ......C............ | 550 | 16 | 7.8 | 15.6 | 35 |
| 1615 SEQ ID NO:39 | ......G............ | 600 | 145 | 7.8 | 45 | 250 |
| 1614 SEQ ID NO:40 | ......A............ | 550 | 31 | 0 | 50 | 250 |
| 1636 SEQ ID NO:41 | ........A.......... | 325 | 250 | 35 | 40 | 0 |
| 1634 SEQ ID NO:42 | ........C.......... | 300 | 400 | 40 | 85 | 200 |
| 1619 SEQ ID NO:43 | ........T.......... | 275 | 450 | 200 | 80 | >500 |
| 1618 SEQ ID NO:44 | ......A..T.......... | 300 | 60 | 15.6 | 15.6 | 62 |
| 1639 SEQ ID NO:45 | .....AA..T.......... | 625 | 220 | 15.6 | 40 | 60 |
| 1707 SEQ ID NO:46 | ......A..TC......... | 300 | 70 | 17 | 0 | 0 |
| 1708 SEQ ID NO:47 | .....CA..TG......... | 270 | 10 | 17 | 0 | 0 | dots indicate identity; CpG dinucleotides are underlined
[1]measured by ELISA using Quantikine kits from R&D Systems (pg/ml)
Cells were cultured in 10% autologous serum with the indicated oligodeoxynucleotides (12 µg/ml) for 4 hr in the case of TNF-α or 24 hr for the other cytokines before supernatant harvest and assay. Data are presented as the level of cytokine above that in wells with no added oligodeoxynucleotide.

CpG DNA Induces Cytokine Secretion by Human PBMC, Specifically Monocytes

The same panels of ODN used for studying mouse cytokine expression were used to determine whether human cells also are induced by CpG motifs to express cytokine (or proliferate), and to identify the CpG motif(s) responsible. Oligonucleotide 1619 (GTCGTT) was the best inducer of TNF-α and IFN-γ secretion, and was closely followed by a nearly identical motif in oligonucleotide 1634 (GTCGCT) (Table 5). The motifs in oligodeoxynucleotides 1637 and 1614 (GCCGGT and GACGGT) led to strong IL-6 secretion with relatively little induction of other cytokines. Thus, it appears that human lymphocytes, like murine lymphocytes, secrete cytokines differentially in response to CpG dinucleotides, depending on the surrounding bases. Moreover, the motifs that stimulate murine cells best differ from those that are most effective with human cells. Certain CpG oligodeoxynucleotides are poor at activating human cells (oligodeoxynucleotides 1707, 1708, which contain the palindrome forming sequences GACGTC and CACGTG respectively).

The cells responding to the DNA appear to be monocytes, since the cytokine secretion is abolished by treatment of the cells with L-leucyl-L-leucine methyl ester (L-LME), which is selectively toxic to monocytes (but also to cytotoxic T lymphocytes and NK cells), and does not affect B cell Ig secretion (Table 6, and data not shown). The cells surviving L-LME treatment had >95% viability by trypan blue exclusion, indicating that the lack of a cytokine response among these cells did not simply reflect a nonspecific death all all cell types. Cytokine secretion in response to E. coli (C) DNA requires unmethylated CpG motifs, since it is abolished by methylation of the EC DNA (next to the bottom row, Table 6). LPS contamination of the DNA cannot explain the results since the level of contamination was identical in the native and methylated DNA, and since addition of twice the highest amount of contaminating LPS had no effect (not shown).

TABLE 6

CpG DNA induces cytokine secretion by human PBMC

| DNA | TNF-α (pg/ml)[1] | IL-6 (pg/ml) | IFN-γ (pg/ml) | RANTES (pg/ml) |
|---|---|---|---|---|
| EC DNA (50 µg/ml) | 900 | 12,000 | 700 | 1560 |
| EC DNA (5 µg/ml) | 850 | 11,000 | 400 | 750 |
| EC DNA (0.5 µg/ml) | 500 | ND | 200 | 0 |
| EC DNA (0.05 µg/ml) | 62.5 | 10,000 | 15.6 | 0 |
| EC DNA (50 µg/ml) + L-LME[2] | 0 | ND | ND | ND |

TABLE 6-continued

CpG DNA induces cytokine secretion by human PBMC

| DNA | TNF-α (pg/ml)[1] | IL-6 (pg/ml) | IFN-γ (pg/ml) | RANTES (pg/ml) |
|---|---|---|---|---|
| EC DNA (10 µg/ml) Methyl.[3] | 0 | 5 | ND | ND |
| CT DNA (50 µg/ml) | 0 | 600 | 0 | 0 |

[1]Levels of all cytokines were determined by ELISA using Quantikine kits from R&D Systems as described in the previous table. Results are representative using PBMC from different donors.
[2]Cells were pretreated for 15 min. with L-leucyl-L-leucine methyl ester (M-LME) to determine whether the cytokine production under these conditions was from monocytes (or other L-LME-sensitive cells).
[3]EC DNA was methylated using 2 U/µg DNA of CpG methylase (New England Biolabs) according to the manufacturer's directions, and methylation confirmed by digestion with Hpa-II and Msp-I. As a negative control, samples were included containing twice the maximal amount of LPS contained in the highest concentration of EC DNA which failed to induce detectable cytokine production under these experimental conditions.
ND = not done The loss of cytokine production in the PBMC treated with L-LME suggested that monocytes may be responsible for cytokine production in response to CpG DNA. To test this hypothesis more directly, the effects of CpG DNA on highly purified human monocytes and macrophages was tested. As hypothesized, CpG DNA directly activated production of the cytokines IL-6, GM-CSF, and TNF-α by human macrophages, whereas non-CpG DNA did not (able 7).

TABLE 7

CpG DNA induces cytokine expression in purified human macrophages

|  | IL-6 (pg/ml) | GM-CSF (pg/ml) | TNF-α (pg/ml) |
|---|---|---|---|
| Cells alone | 0 | 0 | 0 |
| CT DNA (50 µg/ml) | 0 | 0 | 0 |
| EC DNA (50 µg/ml) | 2000 | 15.6 | 1000 |

Biological Role of IL-6 in Inducing Murine IgM Production in Response to CpG Motifs.

Figure 4B:
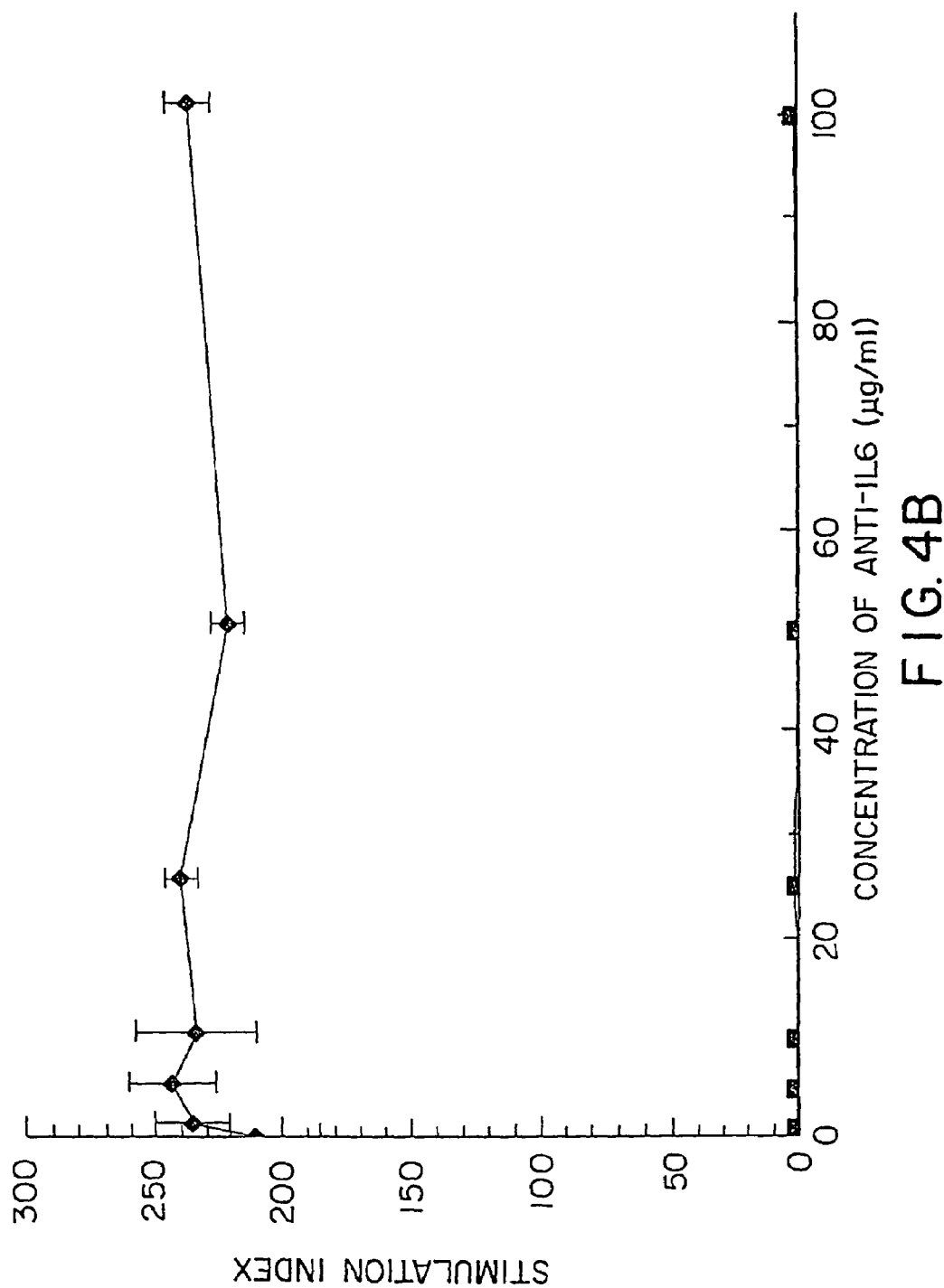
FIG. 4B is a graph plotting the stimulation index of CpG-induced splenic B cells cultured with anti-IL-6 and CpG S-ODN 5' TCCATGACGTTCCTGATGCT 3' (SEQ ID NO:7) (♦) or anti-IL-6 antibody only (■). Data present the mean±standard deviation of triplicates.

The kinetic studies described above revealed that induction of IL-6 secretion, which occurs within 1 hr post CpG stimulation, precedes IgM secretion. Since the optimal CpG motif for ODN inducing secretion of IL-6 is the same as that for IgM (Table 2), whether the CpG motifs independently induce IgM and IL-6 production or whether the IgM production is dependent on prior IL-6 secretion was examined. The addition of neutralizing anti-IL-6 antibodies inhibited in vitro IgM production mediated by CpG ODN in a dose-dependent manner but a control antibody did not (FIG. 4A). In contrast, anti-IL-6 addition did not affect either the basal level or the CpG-induced B cell proliferation (FIG. 4B).

Increased Transcriptional Activity of the IL-6 Promoter in Response to CpG DNA.

Figure 5:
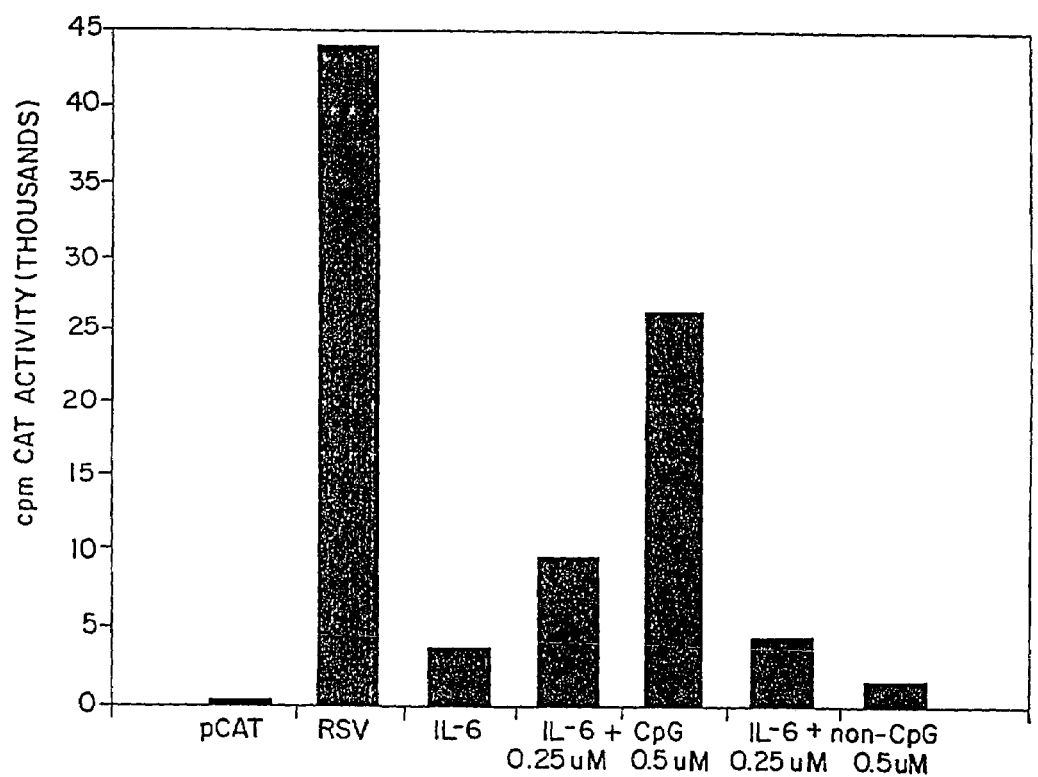
FIG. 5 is a bar graph plotting chloramphenicol acetyltransferase (CAT) activity in WEHI-231 cells transfected with a promoter-less CAT construct (pCAT), positive control plasmid (RSV), or IL-6 promoter-CAT construct alone or cultured with CpG 5' TCCATGACGTTCCTGATGCT 3' (SEQ ID NO:7) or non-CpG 5' TCCATGAGCTTCCTGAGTCT 3' (SEQ ID NO:8) phosphorothioate ODN at the indicated concentrations. Data present the mean of triplicates.

The increased level of IL-6 mRNA and protein after CpG DNA stimulation could result from transcriptional or post-transcriptional regulation. To determine if the transcriptional activity of the IL-6 promoter was upregulated in B cells cultured with CpG ODN, a murine B cell line, WEHI-231, which produces IL-6 in response to CpG DNA, was transfected with an IL-6 promoter-CAT construct (pIL-6/CAT) (Pottratz, S. T. et al., 17B-estradiol) inhibits expression of human interleukin-6-promoter-reporter constructs by a receptor-dependent mechanism. J. Clin. Invest. 93:944). CAT assays were performed after stimulation with various concentrations of CpG or non-CpG ODN. As shown in FIG. 5, CpG ODN induced increased CAT activity in dose-dependent manner while non-CpG ODN failed to induce CAT activity. This confirms that CpG induces the transcriptional activity of the IL-6 promoter.

Dependence of B Cell Activation by CpG ODN on the Number of 5' and 3' Phosphorothioate Internucleotide Linkages.

To determine whether partial sulfur modification of the ODN backbone would be sufficient to enhance B cell activation, the effects of a series of ODN with the same sequence, but with differing numbers of S internucleotide linkages at the 5' and 3' ends were tested. Based on previous studies of nuclease degradation of ODN, it was determined that at least two phosphorothioate linkages at the 5' end of ODN were required to provide optimal protection of the ODN from degradation by intracellular exo- and endo-nucleases. Only chimeric ODN containing two 5' phosphorothioate-mnodified linkages, and a variable number of 3' modified linkages were therefore examined.

The lymphocyte stimulating effects of these ODN were tested at three concentrations (3.3, 10, and 30 µM) by measuring the total levels of RNA synthesis (by $^3$H uridine incorporation) or DNA synthesis (by $^3$H thymidine incorporation) in treated spleen cell cultures (Example 10). O-ODN (0/0 phosphorothioate modifications) bearing a CpG motif caused no spleen cell stimulation unless added to the cultures at concentrations of at least 10 µM (Example 10). However, when this sequence was modified with two S linkages at the 5' end and at least three S linkages at the 3' end, significant stimulation was seen at a dose of 3.3 µM. At this low dose, the level of stimulation showed a progressive increase as the number of 3' modified bases was increased, until this reached or exceeded six, at which point the stimulation index began to decline. In general, the optimal number of 3' S linkages for spleen cell stimulation was five. At all three concentrations tested in these experiments, the S-ODN was less stimulatory than the optimal chimeric compounds.

Dependence of CpG-mediated Lymphocyte Activation on the Type of Backbone Modification.

Phosphorothioate modified ODN (S-ODN) are far more nuclease resistant than phosphodiester modified ODN (O-ODN). Thus, the increased immune stimulation caused by S-ODN and S-O-ODN (i.e. chimeric phosphorothioate ODN in which the central linkages are phosphodiester but the two 5' and five 3' linkages are phosphorothioate modified) compared to O-ODN may result from the nuclease resistance of the former. To determine the role of ODN nuclease resistance in immune stimulation by CpG ODN, the stimulatory effects of chimeric ODN in which the 5' and 3' ends were rendered nuclease resistant with either methylphosphonate (MP-), methylphosphorothioate (MPS-), phosphorothioate (S-), or phosphorodithioate ($S_2$-) internucleotide linkages were tested (Example 10). These studies showed that despite their nuclease resistance, MP-O-ODN were actually less immune stimulatory than O-ODN. However, combining the MP and S modifications by replacing both nonbridging O molecules with 5' and 3' MPS internucleotide linkages restored immune stimulation to a slightly higher level than that triggered by O-ODN.

S-O-ODN were far more stimulatory than O-ODN, and were even more stimulatory than S-ODN, at least at concentrations above 3.3 µM. At concentrations below 3 µM, the S-ODN with the 3M sequence was more potent than the corresponding S-O-ODN, while the S-ODN with the 3D sequence was less potent than the corresponding S-O-ODN (Example 10). In comparing the stimulatory CpG motifs of these two sequences, it was noted that the 3D sequence is a perfect match for the stimulatory motif in that the CpG is flanked by two 5' purines and two 3' pyrimidines. However, the bases immediately flanking the CpG in ODN 3D are not optimal; it has a 5' pyrimidine and a 3' purine. Based on further testing, it was found that the sequence requirement for immune stimulation is more stringent for S-ODN than for S-O- or O-ODN. S-ODN with poor matches to the optimal CpG motif cause little or no lymphocyte activation (e.g. Sequence 3D). However, S-ODN with good matches to the motif, most critically at the positions immediately flanking the CpG, are more potent than the corresponding S-O-ODN (e.g. Sequence 3M, Sequences 4 and 6), even though at higher concentrations (greater than 3 μM) the peak effect from the S-O-ODN is greater (Example 10).

$S_2$-O-ODN were remarkably stimulatory, and caused substantially greater lymphocyte activation than the corresponding S-ODN or S-O-ODN at every tested concentration.

The increased B cell stimulation seen with CpG ODN bearing S or $S_2$ substitutions could result from any or all of the following effects: nuclease resistance, increased cellular uptake, increased protein binding, and altered intracellular localization. However, nuclease resistance can not be the only explanation, since the MP-O-ODN were actually less stimulatory than the O-ODN with CpG motifs. Prior studies have shown that ODN uptake by lymphocytes is markedly affected by the backbone chemistry (Zhao et al., (1993) Comparison of cellular binding and uptake of antisense phosphodiester, phosphorothioate, and mixed phosphorothioate and methylphosphonate oligonucleotides. (Antisense Research and Development 3, 53-66; Zhao et al., (1994) Stage specific oligonucleotide uptake in murine bone marrow B cell precursors. Blood 84, 3660-3666.) The highest cell membrane binding and uptake was seen with S-ODN, followed by S-O-ODN, O-ODN, and MP-ODN. This differential uptake correlates well with the degree of immune stimulation.

Unmethylated CpG Containing Oligos have NK Cell Stimulatory Activity

Experiments were conducted to determine whether CpG containing oligonucleotides stimulated the activity of natural killer (NK) cells in addition to B cells. As shown in Table 8, a marked induction of NK activity among spleen cells cultured with CpG ODN 1 and 3Dd was observed. In contrast, there was relatively no induction in effectors that had been treated with non-CpG control ODN.

TABLE 8

Induction Of NK Activity By CpG Oligodeoxynucleotides (ODN)

|  | % YAC-1 Specific Lysis* Effector:Target | | % 2C11 Specific Lysis Effector:Target | |
| --- | --- | --- | --- | --- |
| ODN | 50:1 | 100:1 | 50:1 | 100:1 |
| None | −1.1 | −1.4 | 15.3 | 16.6 |
| 1 | 16.1 | 24.5 | 38.7 | 47.2 |
| 3Dd | 17.1 | 27.0 | 37.0 | 40.0 |
| non-CpG ODN | −1.6 | −1.7 | 14.8 | 15.4 |

Induction of NK Activity by DNA Containing GpG Motifs, but not by Non-CpG DNA.

Bacterial DNA cultured for 18 hrs. at 37° C. and then assayed for killing of K562 (human) or Yac-1 (mouse) target cells induced NK lytic, activity in both mouse spleen cells depleted of B cells and human PBMC, but vertebrate DNA did not (Table 9). To determine whether the stimulatory activity of bacterial DNA may be a consequence of its increased level of unmethylated CpG dinucleotides, the activating properties of more than 50 synthetic ODN containing unmethylated, methylated, or no CpG dinucleotides was tested. The results, summarized in Table 9, demonstrate that synthetic ODN can stimulate significant NK activity, as long as they contain at least one unmethylated CpG dinucleotide. No difference was observed in the stimulatory effects of ODN in which the CpG was within a palindrome (such as ODN 1585, which contains the palindrome AACGTT) from those ODN without palindromes (such as 1613 or 1619), with the caveat that optimal stimulation was generally seen with ODN in which the CpG was flanked by two 5' purines or a 5' GpT dinucleotide and two 3' pyrimidines. Kinetic experiments demonstrated that NK activity peaked around 18 hrs. afer addition of the ODN. The data indicates that the murine NK response is dependent on the prior activation of monocytes by CpG DNA, leading to the production of EL-12, TNF-α, and IFN-α/β (Example 11).

TABLE 9

Induction of NK Activity by DNA Containing CpG Motifs but not by Non-CpG DNA

|  |  |  | LU/10$^6$ | |
| --- | --- | --- | --- | --- |
| DNA or Cytokine Added | | | Mouse Cells | Human Cells |
| Expt. 1 | None | | 0.00 | 0.00 |
|  | IL-2 | | 16.68 | 15.82 |
|  | E. coli DNA | | 7.23 | 5.05 |
|  | Calf thymus DNA | | 0.00 | 0.00 |
| Expt. 2 | None | | 0.00 | 3.28 |
|  | 1585 gggGTCAA<u>C</u>GTTGAgggggG | (SEQ ID NO:12) | 7.38 | 17.98 |
|  | 1629 .......gtc.......... | (SEQ ID NO:50) | 0.00 | 4.4 |
| Expt. 3 | None | | 0.00 | |
|  | 1613 GCTAGA<u>C</u>GTTAGTGT | (SEQ ID NO:51) | 5.22 | |

TABLE 9-continued

Induction of NK Activity by DNA Containing CpG Motifs but not by Non-CpG DNA

| DNA or Cytokine Added | | | LU/10$^6$ | |
|---|---|---|---|---|
| | | | Mouse Cells | Human Cells |
| 1769 .......Z....... | (SEQ ID NO:52) | | 0.02 | ND |
| 1619 TCCATGT<u>CG</u>TTCCTGATGCT | (SEQ ID NO:43) | | 3.35 | |
| 1765 .......Z............ | (SEQ ID NO:53) | | 0.11 | |

CpG dinucleotides in ODN sequences are indicated by underlying;
Z indicates methylcytosine.
Lower case letters indicate nuclease resistant phosphorothioate modified internucleotide linkages which, in titration experiments, were more than 20 times as potent as non-modified ODN, depending on the flanking bases.
Poly G ends (g) were used in some ODN, because they significantly increase the level of ODN uptake.

Figure 6:
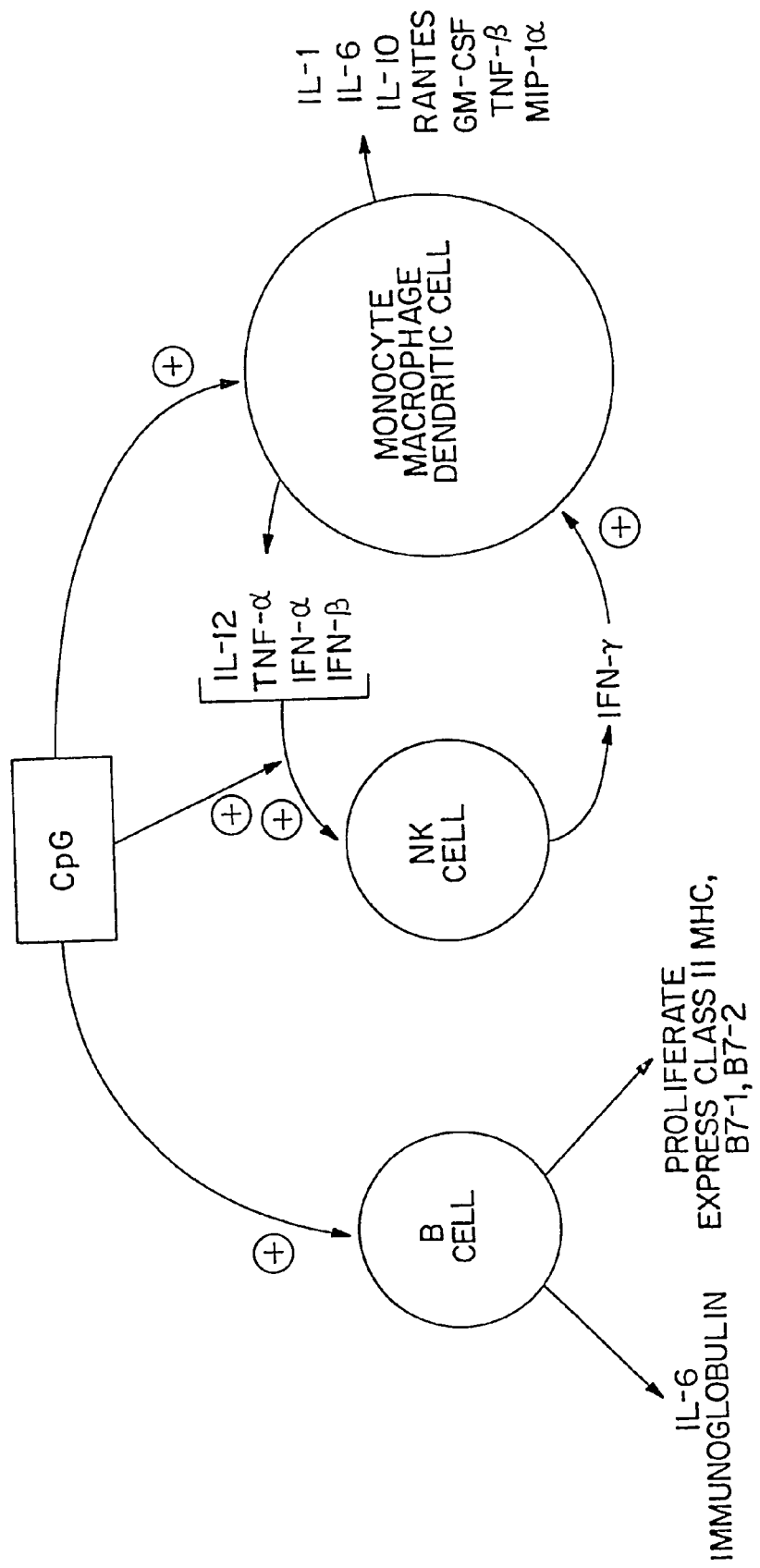
FIG. 6 is a schematic overview of the immune effects of the immunostimulatory unmethylated CpG containing nucleic acids, which can directly activate both B cells and monocytic cells (including macrophages and dendritic cells) as shown. The immunostimulatory oligonucleotides do not directly activate purified NK, cells, but render them competent to respond to IL-12 with a marked increase in their IFN-γ production. By inducing IL-12 production and the subsequent increased IFN-γ secretion by NK cells, the immunostimulatory nucleic acids promote a Th1 type immune response. No direct activation of proliferation of cytokine secretion by highly purified T cells has been found. However, the induction of Th1 cytokine secretion by the immunostimulatory oligonucleotides promotes the development of a cytotoxic lymphocyte response.

From all of these studies, a more complete understanding of the immune effects of CpG DNA has been developed, which is summarized in FIG. 6.

Identification of B Cell and Monocyte/NK Cell-specific Oligonucleotides

As shown in FIG. 6, CpG DNA can directly activate highly purified B cells and monocytic cells. There are many similarities in the mechanism through which CpG DNA activates these cell types. For example, both require NFκB activation as explained further below.

In further studies of different immune effects of CpG DNA, it was found that there is more than one type of CpG motif. Specifically, oligo 1668, with the best mouse B cell motif, is a strong inducer of both B cell and natural killer (NK) cell activation, while oligo 1758 is a weak B cell activator, but still induces excellent NK responses (Table 10).

TABLE 10

Different CpG motifs stimulate optimal murine B cell and NK activation

| ODN Sequence | B cell activation[1] | NK activation[2] |
|---|---|---|
| 1668 TCCATGA<u>CG</u>TTCCTGATGCT (SEQ ID NO:54) | 42,849 | 2.52 |
| 1758 TCTCCCAG<u>CG</u>TG<u>CG</u>CCAT (SEQ ID NO:55) | 1,747 | 6.66 |
| NONE | 367 | 0.00 |

CpG dinucleotides are underlined; oligonucleotides were synthesized with phosphorothioate modified backbones to improve their nuclease resistance.
[1]Measured by $^3$H thymidine incorporation after 48 hr culture with oligodeoxynucleotides at a 200 nM concentration as described in Example 1.
[2]Measured by lytic units.

Teleological Basis of Immunostimulatory, Nucleic Acids

Vertebrate DNA is highly methylated and CpG dinucleotides are underrepresented. However, the stimulatory CpG motif is common in microbial genomic DNA, but quite rare in vertebrate DNA. In addition, bacterial DNA has been reported to induce B cell proliferation and immunoglobulin (Ig) production, while mammalian DNA does not (Messina, J. P. et al., *J. Immunol.* 147:1759 (1991)). Experiments further described in Example 3, in which methylation of bacterial DNA with CpG methylase was found to abolish mitogenicity, demonstrates that the difference in CpG status is the cause of B cell stimulation by bacterial DNA. This data supports the following conclusion: that unmethylated CpG dinucleotides present within bacterial DNA are responsible for the stimulatory effects of bacterial DNA.

Teleologically, it appears likely that lymphocyte activation by the CpG motif represents an immune defense mechanism that can thereby distinguish bacterial from host DNA. Host DNA, which would commonly be present in many anatomic regions and areas of inflammation due to apoptosis (cell death), would generally induce little or no lymphocyte activation due to CpG suppression and methylation. However, the presence of bacterial DNA containing unmethylated CpG motifs can cause lymphocyte activation precisely in infected anatomic regions, where it is beneficial. This novel activation pathway provides a rapid alternative to T cell dependent antigen specific B cell activation. Since the CpG pathway synergizes with B cell activation through the antigen receptor, B cells bearing antigen receptor specific for bacterial antigens would receive one activation signal through cell membrane Ig and a second signal from bacterial DNA, and would therefore tend to be preferentially activated. The interrelationship of this pathway with other pathways of B cell activation provide a physiologic mechanism employing a polyclonal antigen to induce antigen-specific responses.

However, it is likely that B cell activation would not be totally nonspecific. B cells bearing antigen receptors specific for bacterial products could receive one activation signal through cell membrane Ig, and a second from bacterial DNA, thereby more vigorously triggering antigen specific immune responses. As with other immune defense mechanisms, the response to bacterial DNA could have undesirable consequences in some settings. For example, autoimmnune responses to self antigens would also tend to be preferentially triggered by bacterial infections, since autoantigens could also provide a second activation signal to autoreactive B cells triggered by bacterial DNA. Indeed the induction of autoimmunity by bacterial infections is a common clinical observance. For example, the autoimmune disease systemic lupus erythematosus, which is: i) characterized by the production of anti-DNA antibodies; ii) induced by drugs which inhibit DNA methyltransferase (Cornacchia, E. J. et al., *J. Clin. Invest.* 92:38 (1993)); and iii) associated with reduced DNA methylation (Richardson, B. L,. et al., *Arth. Rheum* 35:647 (1992)), is likely triggered at least in part by activation of DNA-specific B cells through stimulatory signals provided by CpG motifs, as well as by binding of bacterial DNA to antigen receptors.

Further, sepsis, which is characterized by high morbidity and mortality due to massive and nonspecific activation of the immune system may be initiated by bacterial DNA and other products released from dying bacteria that reach concentrations sufficient to directly activate many lymphocytes. Further evidence of the role of CpG DNA in the sepsis syndrome is described in Cowdery, J., et. al., (1996) *The Journal of Immunology* 156:4570-4575.

Proposed Mechanisms of Action

Unlike antigens that trigger B cells through their surface Ig receptor, CpG-ODN did not induce any detectable $Ca^{2+}$ flux, changes in protein tyrosine phosphorylation, or IP 3 generation. Flow cytometry with FITC-conjugated ODN with or without a CpG motif was performed as described in Zhao, Q et al., (*Antisense Research and Development* 3:53-66 (1993)), and showed equivalent membrane binding, cellular uptake, efflux, and intracellular localization. This suggests that there may not be cell membrane proteins specific for CpG ODN. Rather than acting through the cell membrane, that data suggests that unmethylated CpG containing oligonucleotides require cell uptake for activity: ODN covalently linked to a solid Teflon support were nonstimulatory, as were biotinylated ODN immobilized on either avidin beads or avidin coated petri dishes. CpG ODN conjugated to either FITC or biotin retained full mitogenic properties, indicating no steric hindrance.

Figure 7:
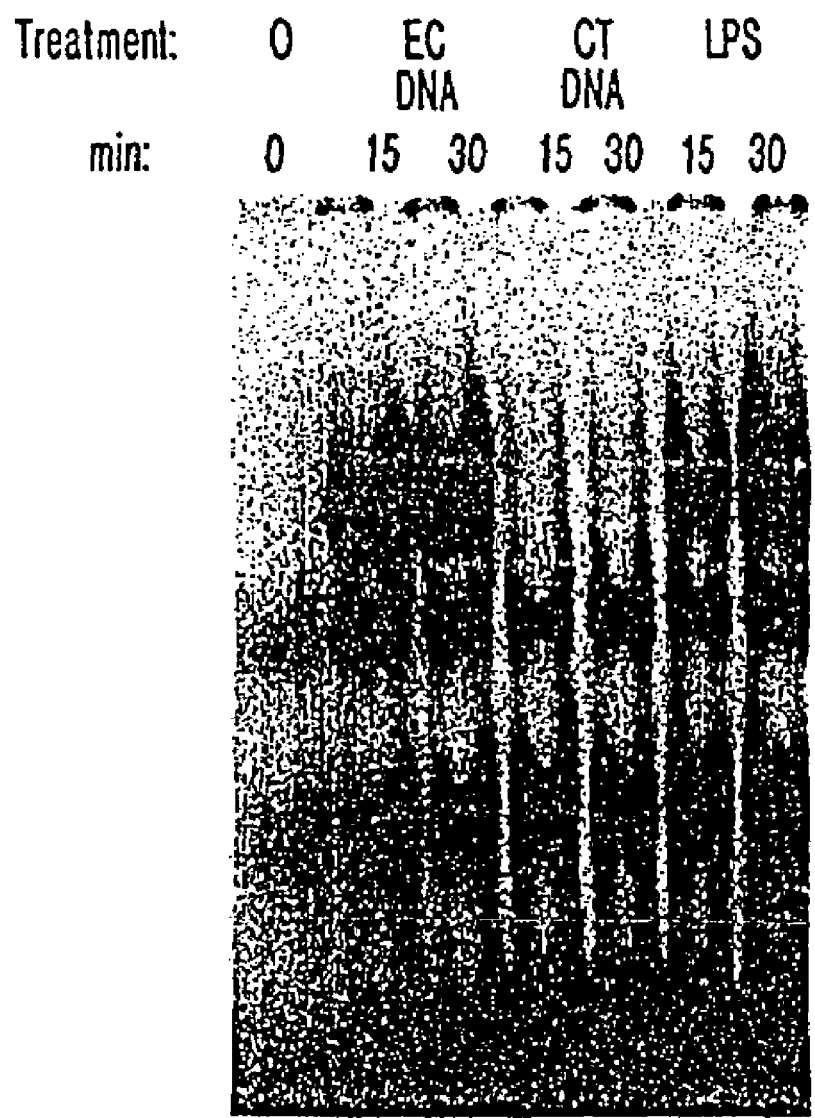
FIG. 7 is an autoradiograph showing NFκB mRNA induction in monocytes treated with E. coli (EC) DNA (containing unmethylated CpG motifs), control (CT) DNA (containing no unmethylated CpG motifs) and lipopolysaccharide (LPS) at various measured times, 15 and 30 minutes after contact.

Recent data indicate the involvement of the transcription factor NFκB as a direct or indirect mediator of the CpG effect. For example, within 15 minutes of treating B cells or monocytes with CpG DNA, the level of NFκB binding activity is increased (FIG. 7). However, it is not increased by DNA that does not contain CpG motifs. In addition, it was found that two different inhibitors of NFκB activation, PDTC and gliotoxin, completely block the lymphocyte stimulation by CpG. DNA as measured by B cell proliferation or monocytic cell cytokine secretion, suggesting that NFκB activation is required for both cell types.

There are several possible mechanisms through which NFκB can be activated. These include through activation of various protein kinases, or through the generation of reactive oxygen species. No evidence for protein kinase activation induced immediately after CpG DNA treatment of B cells or monocytic cells have been found, and inhibitors of protein kinase A, protein kinase C, and protein tyrosine kinases had no effects on the CpG induced activation. However, CpG DNA causes a rapid induction of the production of reactive oxygen species in both B cells and monocytic cells, as detected by the sensitive fluorescent dye dihydrorhodamine 123 as described in Royall, J. A., and Ischiropoulos, H. (*Archives of Biochemistry and Biophysics* 302:348-355 (1993)). Moreover, inhibitors of the generation of these reactive oxygen species completely block the induction of NFκB and the later induction of cell proliferation and cytokine secretion by CpG DNA.

Figure 8A:
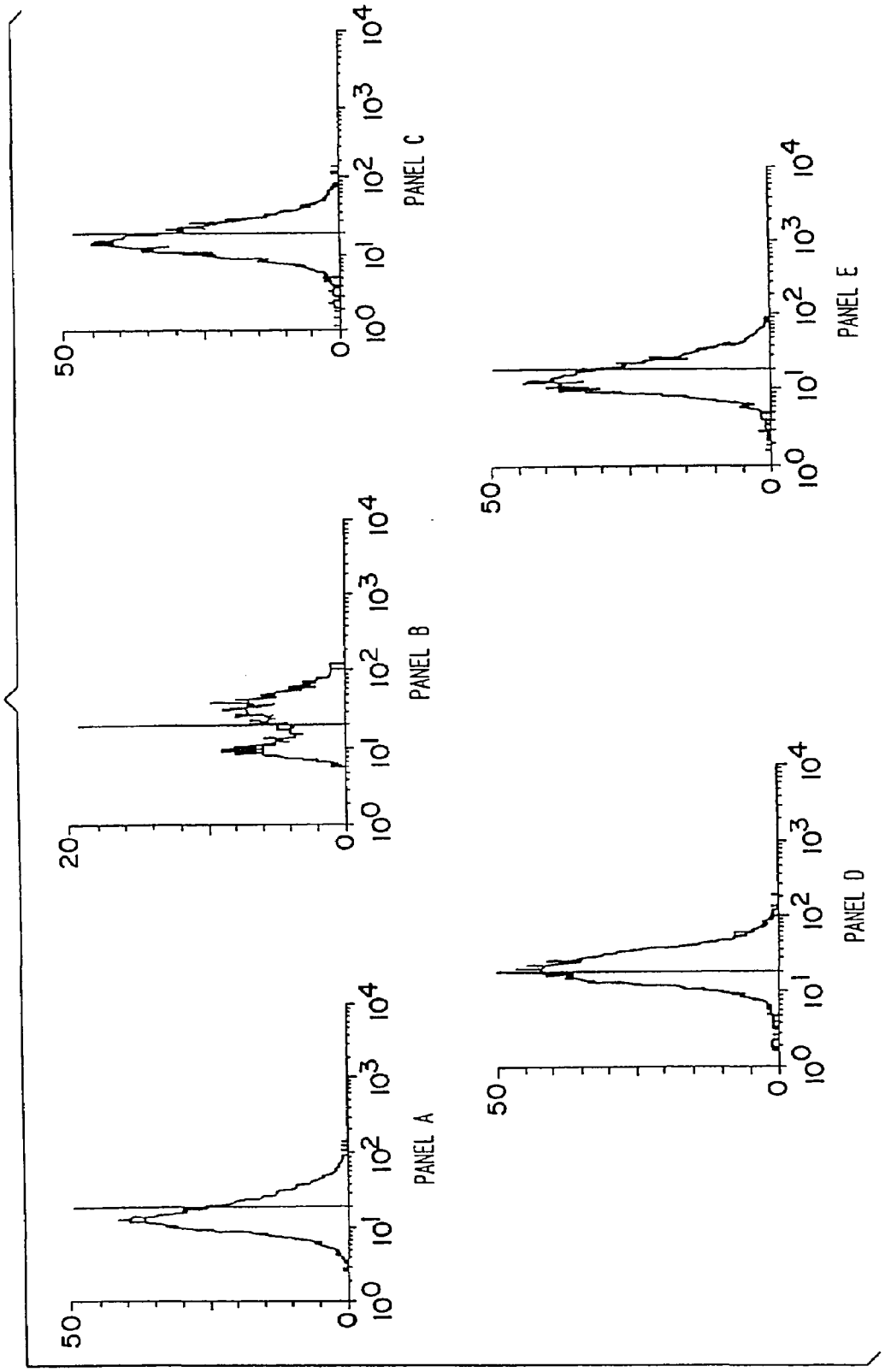
FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. This level of reactive oxygen species was greatly increased to 80% in the cells treated for 20 minutes with PMA and ionomycin, a positive control (Panel B). The cells treated with the CpG oligo (TC-CATGACGTTCCTGACGTT SEQ ID NO:10) also showed an increase in the level of reactive oxygen species such that more than 50% of the cells became positive (Panel D). However, cells treated with an oligonucleotide with the identical sequence except that the CpGs were switched (TCCAT-GAGCTTCCTGAGTGCT SEQ ID NO:11) did not show this significant increase in the level of reactive oxygen species (Panel E).

Working backwards, the next question was how CpG DNA leads to the generation of reactive oxygen species so quickly. Previous studies by the inventors demonstrated that oligonucleotides and plasmid or bacterial DNA are taken up by cells into endosomes. These endosomes rapidly become acidified inside the cell. To determine whether this acidification step may be important in the mechanism through which CpG DNA activates reactive oxygen species) the acidification step was blocked with specific inhibitors of endosome acidification including chloroquine, monensin, and bafilomycin, which work through different mechanisms. FIG. 8A shows the results from a flow cytometry study using mouse B cells with the dihydrorhodamine 123 dye to determine levels of reactive oxygen species. The dye only sample in Panel A of the figure shows the background level of cells positive for the dye at 28.6%. As expected, this level of reactive oxygen species was greatly increased to 80% in the cells treated for 20 minutes with PMA and ionomycin, a positive control (Panel B). The cells treated with the CpG oligo also showed an increase in the level of reactive oxygen species such that more than 50% of the cells became positive (Panel D). However, cells treated with an oligonucleotide with the identical sequence except that the CpG was switched did not show this significant increase in the level of reactive oxygen species (Panel E).

Figure 8B:
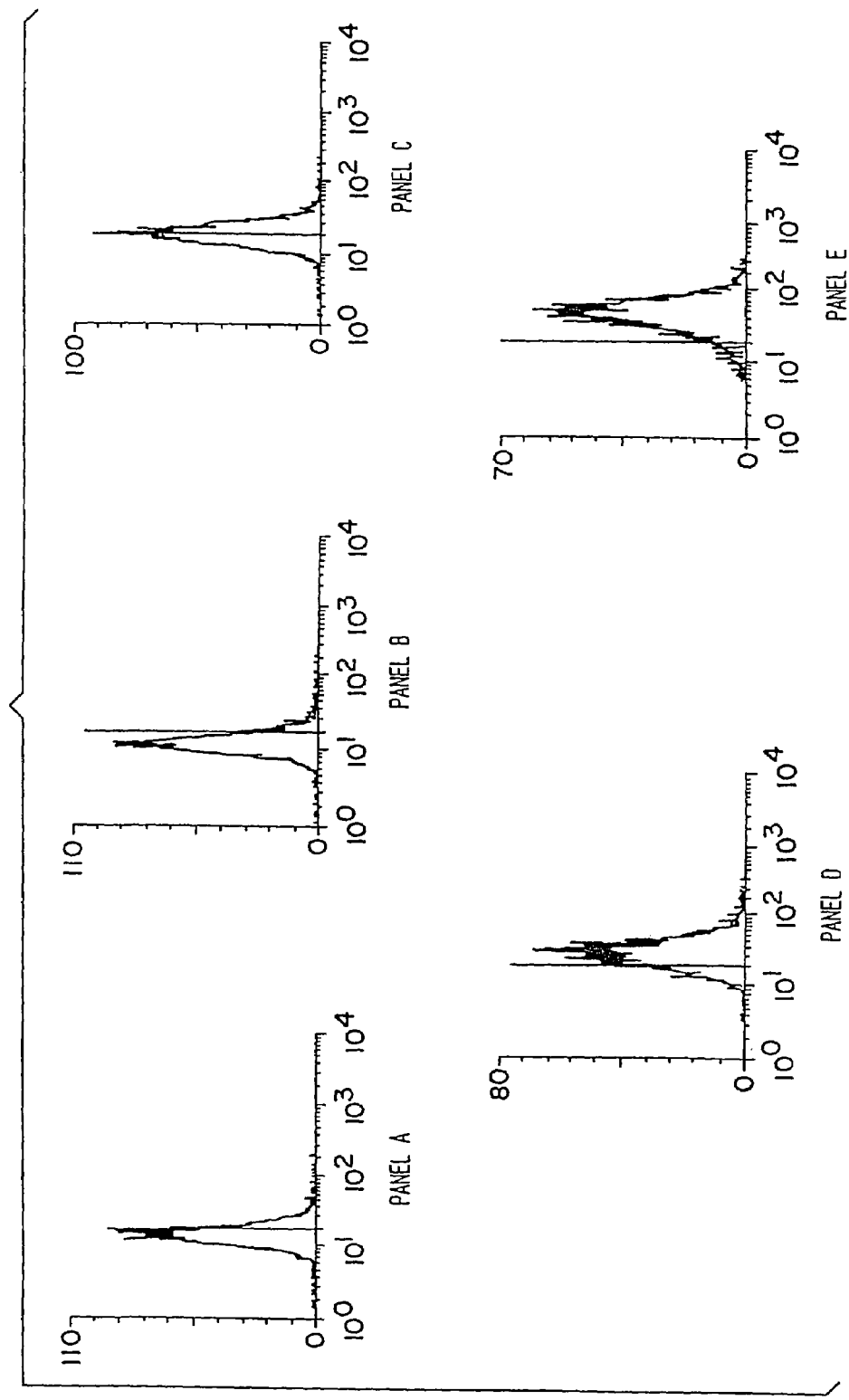
FIG. 8B shows the results from a flow cytometry study using mouse B cells in the presence of chloroquine with the dihydrorhodamine 123 dye to determine levels of reactive oxygen species. Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in the cells treated with PMA and ionomycin (Panel E).

In the presence of chloroquine, the results are very different (FIG. 8B). Chloroquine slightly lowers the background level of reactive oxygen species in the cells such that the untreated cells in Panel A have only 4.3% that are positive. Chloroquine completely abolishes the induction of reactive oxygen species in the cells treated with CpG DNA (Panel B) but does not reduce the level of reactive oxygen species in the cells treated with PMA and ionomycin (Panel E). This demonstrates that unlike the PMA plus ionomycin, the generation of reactive oxygen species following treatment of B cells with CpG DNA requires that the DNA undergo an acidification step in the endosomes. This is a completely novel mechanism of leukocyte activation. Chloroquine, monensin, and bafilomycin also appear to block the activation of NFκB by CpG DNA as well as the subsequent proliferation and induction of cytokine secretion.

Presumably, there is a protein in or near the endosomes that specifically recognizes DNA containing CpG motifs and leads to the generation of reactive oxygen species. To detect any protein in the cell cytoplasm that may specifically bind CpG DNA, we used electrophoretic mobility shift assays (EMSA) with 5' radioactively labeled oligonucleotides with or without CpG motifs. A band was found that appears to represent a protein binding specifically to single stranded oligonucleotides that have CpG motifs, but not to oligonucleotides that lack CpG motifs or to oligonucleotides in which the CpG motif has been methylated. This binding activity is blocked if excess of oligonucleotides that contain the NFκB binding site was added. This suggest that an NFκB or related protein is a component of a protein or protein complex that binds the stimulatory CpG oligonucleotides.

No activation of CREB/ATF proteins was found at time points where NFκB was strongly activated. These data therefore do not provide proof that NFκB proteins actually bind to the CpG nucleic acids, but rather that the proteins are required in some way for the CpG activity. It is possible that a CREB/ATF or related protein may interact in some way with NFk8 B proteins or other proteins thus explaining the remarkable similarity in the binding motifs for CREB proteins and the optimal CpG motif. It remains possible that the oligos bind to a CREB/ATF or related protein, and that this leads to NFκB activation.

Alternatively, it is very possible that the CpG nucleic acids may bind to one of the TRAF proteins that bind to the cytoplasmic region of CD40 and mediate NFκB activation when CD40 is cross-linked. Examples of such TRAF proteins include TRAF-2 and TRAF-5.

Method for Making Immunostimulatory Nucleic Acids

For use in the instant invention, nucleic acids can be synthesized de novo using any of a number of procedures well known in the art. For example, the β-cyanoethyl phosphoramidite method (S. L. Beaucage and M. H. Caruthers, (1981)

Tet. Let. 22:159); nucleoside H-phosphonate method (Garegg et al., (1986) Tet. Let. 27:4051-4054; Froehler et al., (1986) Nucl. Acid. Res. 14: 5399-5407; Garegg et al., (1986) Tet. Let. 27: 4055-4059, Gaffney et al., (1988) Tet. Let. 29:2619-2622). These chemistries can be performed by a variety of automated oligonucleotide synthesizers available in the market. Alternatively, oligonucleotides can be prepared from existing nucleic acid sequences (e.g. genomic or cDNA) using known techniques, such as those employing restriction enzymes, exonucleases or endonucleases.

For use in vivo, nucleic acids are preferably relatively resistant to degradation (e.g. via endo- and exo-nucleases). Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioate may be synthesized using automated techniques employing either phosphoramidate or H-phosphonate chemistries. Aryl- and alkyl-phosphonates can be made e.g. as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents, Methods for making other DNA backbone modifications and substitutions have been described (Uhlmann, E. and Peyman, A. (1990) Chem. Rev. 90:544; Goodchild, J. (1990) Bioconjugate Chem. 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C.

For administration in vivo, nucleic acids may be associated with a molecule that results in higher affinity binding to target cell (e.g. B-cell, monocytic cell and natural killer (NK) cell) surfaces and/or increased cellular uptake by target cells to form a "nucleic acid delivery complex". Nucleic acids can be ionically, or covalently associated with appropriate molecules using techniques which are well known in the art. A variety of coupling or crosslinking agents can be used e.g. protein A, carbodiimide, and N-succinimidyl-3-(2-pyridyldithio) propionate (SPDP). Nucleic acids can alternatively be encapsulated in liposomes or virosomes using well-known techniques.

Therapeutic Uses of Immunostimulatory Nucleic Acid Molecules

Based on their immunostimulatory properties, nucleic acid molecules containing at least one unmethylated CpG dinucleotide can be administered to a subject in vivo to treat an "immune system deficiency". Alternatively, nucleic acid molecules containing at least one unmethylated CpG dinucleotide can be contacted with lymphocytes (e.g. B cells, monocytic cells or NK cells) obtained from a subject having an immune system deficiency ex vivo and activated lymphocytes can then be reimplanted in the subject.

As reported herein, in response to unmethylated CpG containing nucleic acid molecules, an increased number of spleen cells secrete IL-6, IL-12, IFN-γ, IFN-α, IFN-β, IL-1, I3, IL-10, TNF-α, TNF-β, GM-CSF, RANTES, and probably others. The increased IL-6 expression was found to occur in B cells, CD4+ T cells and monocytic cells.

Immunostimulatory nucleic acid molecules can also be administered to a subject in conjunction with a vaccine to boost a subject's immune system and thereby effect a better response from the vaccine. Preferably the immunostimulatory nucleic acid molecule is administered slightly before or at the same time as the vaccine. A conventional adjuvant may optionally be administered in conjunction with the vaccine, which is minimally comprised of an antigen, as the conventional adjuvant may further improve the vaccination by enhancing antigen absorption.

When the vaccine is a DNA vaccine at least two components determine its efficacy. First, the antigen encoded by the vaccine determines the specificity of the immune response. Second, if the backbone of the plasmid contains CpG motifs, it functions as an adjuvant for the vaccine. Thus, CpG DNA acts as an effective "danger signal" and causes the immune system to respond vigorously to new antigens in the area. This mode of action presumably results primarily from the stimulatory local effects of CpG DNA on dendritic cells and other "professional" antigen presenting cells, as well as from the costimulatory effects on B cells.

Immunostimulatory oligonucleotides and unmethylated CpG containing vaccines, which directly activate lymphocytes and co-stimulate an antigen-specific response, are fundamentally different from conventional adjuvants (e.g. aluminum precipitates), which are inert when injected alone and are thought to work through absorbing the antigen and thereby presenting it more effectively to immune cells. Further, conventional adjuvants only work for certain antigens, only induce an antibody (humoral) immune response (Th2), and are very poor at inducing cellular immune responses (Th1). For many pathogens, the humoral response contributes little to protection, and can even be detrimental.

In addition, an immunostimulatory oligonucleotide can be administered prior to, along with or after administration of a chemotherapy or immunotherapy to increase the responsiveness of the malignant cells to subsequent chemotherapy or immunotherapy or to speed the recovery of the bone marrow through induction of restorative cytokines such as GM-CSF. CpG nucleic acids also increase natural killer cell lytic activity and antibody dependent cellular cytotoxicity (ADCC). Induction of NK activity and ADCC may likewise be beneficial in cancer immunotherapy, alone or in conjunction with other treatments.

Another use of the described immunostimulatory nucleic acid molecules is in desensitization therapy for allergies, which are generally caused by IgE antibody generation against harmless allergens. The cytokines that are induced by unmethylated CpG nucleic acids are predominantly of a class called "Th1" which is most marked by a cellular immune response and is associated with IL-12 and IFN-γ. The other major type of immune response is termed a Th2 immune response, which is associated with more of an antibody immune response and with the production of IL-4, IL-5 and IL-10. In general, it appears that allergic diseases are mediated by Th2 type immune responses and autoimmune diseases by Th1 immune response. Based on the ability of the immunostimulatory nucleic acid molecules to shift the immune response in a subject from a Th2 (which is associated with production of IgE, antibodies and allergy) to a Th1 response (which is protective against allergic reactions), an effective dose of an immunostimulatory nucleic acid (or a vector containing a nucleic acid) alone or in conjunction with an allergen can be administered to a subject to treat or prevent an allergy.

Nucleic acids containing unmethylated CpG motifs may also have significant therapeutic utility in the treatment of asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines.

As described in detail in the following Example 12, oligonucleotides containing an unmethylated CpG motif (i.e. TCCATGACGTTCCTGACGTT; SEQ ID NO:10), but not a control oligonucleotide (TCCATGAGCTTCCTGAGTCT; SEQ ID NO:11) prevented the development of an inflammatory cellular infiltrate and eosinophilia in a murine model of asthma. Furthermore, the suppression of eosinophilic inflammation was associated with a suppression of a Th2 response and induction of a Th1 response.

For use in therapy, an effective amount of an appropriate immunostimulatory nucleic acid molecule alone or formulated as a delivery complex can be administered to a subject by any mode allowing the oligonucleotide to be taken up by the appropriate target cells (e.g., B-cells and monocytic cells). Preferred routes of administration include oral and transdermal (e.g., via a patch). Examples of other routes of administration include injection (subcutaneous, intravenous, parenteral, intraperitoneal, intrathecal, etc.). The injection can be in a bolus or a continuous infusion.

A nucleic acid alone or as a nucleic acid delivery complex can be administered in conjunction with a pharmaceutically acceptable carrier. As used herein, the phrase "pharmaceutically acceptable carrier" is intended to include substances that can be coadministered with a nucleic acid or a nucleic acid delivery complex and allows the nucleic acid to perform its indicated function. Examples of such carriers include solutions, solvents, dispersion media, delay agents, emulsions and the like. The use of such media for pharmaceutically active substances are well known in the art. Any other conventional carrier suitable for use with the nucleic acids falls within the scope of the instant invention.

The language "effective amount" of a nucleic acid molecule refers to the amount necessary or sufficient to realize a desired biologic effect. For example, an effective amount of a nucleic acid containing at least one unmethylated CpG for treating an immune system deficiency could be that amount necessary to eliminate a tumor, cancer, or bacterial, viral or fungal infection. An effective amount for use as a vaccine adjuvant could be that amount useful for boosting a subjects immune response to a vaccine. An "effective amount" for treating asthma can be that amount useful for redirecting a Th2 type of immune response that is associated with asthma to a Th1 type of response. The effective amount for any particular application can vary depending on such factors as the disease or condition being treated, the particular nucleic acid being administered (e.g. the number of unmethylated CpG motifs or their location in the nucleic acid), the size of the subject, or the severity of the disease or condition. One of ordinary skill in the art can empirically determine the effective amount of a particular oligonucleotide without necessitating undue experimentation.

The present invention is further illustrated by the following Examples which in no way should be construed as further limiting. The entire contents of all of the references (including literature references, issued patents, published patent applications and co-pending patent applications) cited throughout this application are hereby expressly incorporated by reference.

EXAMPLES

Example 1

Effects of ODNs on B Cell Total RNA Synthesis and Cell Cycle

B cells were purified from spleens obtained from 6-12 wk old specific pathogen free DBA/2 or BXSB mice (bred in the University of Iowa animal care facility; no substantial strain differences were noted) that were depleted of T cells with anti-Thy-1.2 and complement and centrifugation over lympholyte M (Cedarlane Laboratories, Hornby, Ontario, Canada) ("B cells"). B cells contained fewer than 1% CD4$^+$ or CD8$^+$ cells. 8×10$^4$ B cells were dispensed in triplicate into 96 well microtiter plates in 100 μl RPMI containing 10% FBS (heat inactivated to 65° C. for 30 min.), 50 μM 2-mercaptoethanol, 100 U/ml penicillin, 100 ug/ml streptomycin, and 2 mM L-glutamate. 20 μM ODN were added at the start of culture for 20 h at 37° C., cells pulsed with 1 μCi of $^3$H uridine, and harvested and counted 4 hr later. Ig secreting B cells were enumerated using the ELISA spot assay after culture of whole spleen cells with ODN at 20 μM for 48 hr. Data, reported in Table 1, represent the stimulation index compared to cells cultured without ODN. $^3$H thymidine incorporation assays showed similar results, but with some nonspecific inhibition by thymidine released from degraded ODN (Matson. S and A. M. Krieg (1992) Nonspecific suppression of $^3$H-thymidine incorporation by control oligonucleotides. *Antisense Research and Development* 2:325).

Example 2

Effects of ODN on Production of IgM from B Cells

Single cell suspensions from the spleens of freshly killed mice were treated with anti-Thy1, anti-CD4, and anti-CD8 and complement by the method of Leibson et al., *J. Exp. Med.* 154:1681 (1981)). Resting B cells (<02% T cell contamination) were isolated from the 63-70% band of a discontinuous Percoll gradient by the procedure of DeFranco et al, *J. Exp. Med.* 155:1523 (1982). These were cultured as described above in 30 μM ODN or 20 μg/ml LPS for 48 hr. The number of B cells actively secreting IgM was maximal at this time point, as determined by ELIspot assay (Klinman, D. M. et al. *J. Immunol.* 144:506 (1990)). In that assay, B cells were incubated for 6 hrs on anti-Ig coated microtiter plates. The Ig they produced (>99% IgM) was detected using phosphatase-labelled anti-Ig (Southern Biotechnology Associated, Birmingham, Ala). The antibodies produced by individual B cells were visualized by addition of BCIP (Sigma Chemical Co., St. Louis Mo.) which forms an insoluble blue precipitate in the presence of phosphatase. The dilution of cells producing 20-40 spots/well was used to determine the total number of antibody-secreting B cells/sample. All assays were performed in triplicate (data reported in Table 1). In some experiments, culture supernatants were assayed for IgM by ELISA, and showed similar increases in response to CpG-ODN.

Example 3

B cell Stimulation by Bacterial DNA

DBA/2 B cells were cultured with no DNA or 50 µg/ml of a) Micrococcus lysodeikticus; b) NZB/N mouse spleen; and c) NFS/N mouse spleen genomic DNAs for 48 hours, then pulsed with $^3$H thymidine for 4 hours prior to cell harvest. Duplicate DNA samples were digested with DNAse I for 30 minutes at 37 C prior to addition to cell cultures. E. coli DNA also induced an 8.8 fold increase in the number of IgM secreting B cells by 48 hours using the ELISA-spot assay.

DBA/2 B cells were cultured with either no additive, 50 µg/ml LPS or the ODN 1; 1a; 4; or 4a at 20 uM. Cells were cultured and harvested at 4, 8, 24 and 48 hours. BXSB cells were cultured as in Example 1 with 5, 10, 20, 40 or 80 µM of ODN 1; 1a; 4; or 4a or LPS. In this experiment, wells with no ODN had 3833 cpm. Each experiment was performed at least three times with similar results. Standard deviations of the triplicate wells were <5%.

Example 4

Effects of ODN on Natural Killer (NK) Activity $10 \times 10^6$ C57BL/6 spleen cells were cultured in two ml RPMI (supplemented as described for Example 1) with or without 40 µM CpG or non-CpG ODN for forty-eight hours. Cells were washed, and then used as effector cells in a short term $^{51}$Cr release assay with YAC-1 and 2C11, two NK sensitive target cell lines (Ballas, Z. K. et al. (1993) J. Immunol. 150:17). Effector cells were added at various concentrations to $10^4$ $^{51}$Cr-labeled target cells in V-bottom microtiter plates in 0.2 ml, and incubated in 5% $CO_2$ for 4 hr. at 37° C. Plates were then centrifuged, and an aliquot of the supernatant counted for radioactivity. Percent specific lysis was determined by calculating the ratio of the $^{51}$Cr released in the presence of effector cells minus the $^{51}$Cr released when the target cells are cultured alone, over the total counts released after cell lysis in 2% acetic acid minus the $^{51}$Cr cpm released when the cells are cultured alone.

Example 5

In Vivo Studies with CpG Phosphorothioate ODN

Mice were weighed and injected IP with 0.25 ml of sterile PBS or the indicated phophorothioate ODN dissolved in PBS. Twenty four hours later, spleen cells were harvested, washed, and stained for flow cytometry using phycoerythrin conjugated 6B2 to gate on B cells in conjunction with biotin conjugated anti Ly-6A/E or anti-Ia$^d$ (Pharmingen, San Diego, Calif.) or anti-Bla-1 (Hardy, R. R. et al., J. Exp. Med. 159: 1169 (1984). Two mice were studied for each condition and analyzed individually.

Example 6

Titration of Phosphorothioate ODN for B Cell Stimulation

B cells were cultured with phosphorothioate ODN with the sequence of control ODN 1a or the CpG ODN 1d and 3Db and then either pulsed after 20 hr with $^3$H uridine or after 44 hr with $^3$H thymidine before harvesting and determining cpm.

Example 7

Rescue of B Cells From Apoptosis

WEHI-231 cells ($5 \times 10^4$/well) were cultured for 1 hr. at 37 C in the presence or absence of LPS or the control ODN 1a or the CpG ODN 1d and 3Db before addition of anti-IgM (1 µ/ml). Cells were cultured for a further 20 hr. before a 4 hr. pulse with 2 µCi/well $^3$H thymidine. In this experiment, cells with no ODN or anti-IgM gave $90.4 \times 10^3$ cpm of $^3$H thymidine incorporation by addition of anti-IgM. The phosphodiester ODN shown in Table 1 gave similar protection, though with some nonspecific suppression due to ODN degradation. Each experiment was repeated at least 3 times with similar results.

Example 8

In Vivo Induction of Murine IL-6

DBA/2 female mice (2 mos. old) were injected IP with 500 µg CpG or control phosphorothioate ODN. At various time points after injection, the mice were bled. Two mice were studied for each time point. IL-6 was measured by Elisa, and IL-6 concentration was calculated by comparison to a standard curve generated using recombinant IL-6. The sensitivity of the assay was 10 pg/ml. Levels were undetectable after 8 hr.

Example 9

Systemic Induction of Murine IL-6 Transcription

Mice and cell lines. DBA/2, BALB/c, and C3H/HeJ mice at 5-10 wk of age were used as a source of lymphocytes. All mice were obtained from The Jackson Laboratory (Bar Harbor, Me.), and bred and maintained under specific pathogen-free conditions in the university of Iowa Animal Care Unit. The mouse B cell line CH12.LX was kindly provided by Dr. G. Bishop (University of Iowa, Iowa City).

Cell preparation. Mice were killed by cervical dislocation. Single cell suspensions were prepared aseptically from the spleens from mice. T cell depleted mouse splenocytes were prepared by using anti-Thy-1.2 and complement and centrifugation over lympholyte M (Cedarlane Laboratories, Hornby, Ontario, Canada) as described (Krieg, A. M. et al., (1989) A role for endogenous retroviral sequences in the regulation of lymphocyte activation. J. Immunol. 143:2448).

ODN and DNA. Phosphodiester oligonucleotides (O-ODN) and the backbone modified phosphorothioate oligonucleotides (S-ODN) were obtained from the DNA Core facility at the University of Iowa or from Operon Technologies (Alameda, Calif.). E. coli DNA (Strain B) and calf thymus DNA were purchased from Sigma (St. Louis, Mo.). All DNA and ODN were purified by extraction with phenol: chloroform:isoamyl alcohol (25:24:1) and/or ethanol precipitation. E. coli and calf thymus DNA were single stranded prior to use by boiling for 10 min. followed by cooling on ice for 5 min. For some experiments, E. coli and calf thymus DNA were digested with DNAse I (2U/µg of DNA) at 37° C. for 2 hr in 1×SSC with 5 mM $MgCl_2$. To methylate the cytosine in CpG dinucleotides in E. coli DNA, E. coli DNA was treated with CpG methylase (M. SssI; 2U/1µg of DNA) in NEBuffer 2 supplemented with 160 µM S-adenosyl methionine and incubated overnight at 37° C. Methylated DNA was purified as above. Efficiency of methylation was confirmed by Hpa II digestion followed by analysis by gel electrophoresis. All enzymes were purchased from New England Biolabs (Beverly, Mass.). LPS level in ODN was less than 12.5 ng/mg and *E. coli* and calf thymus DNA contained less than 2.5 ng of LPS/mg of DNA by Limulus assay.

Cell Culture. All cells were cultured at 37° C. in a 5% $CO_2$ humidified incubator maintained in RPMI-1640 supplemented with 10% (v/v) heat inactivated fetal calf serum (FCS), 1.5 nM L-glutamine, 50 µg/ml), CpG or non-CpG phosphodiester ODN (O-ODN) (20 µM), phosphorothioate ODN (S-ODN) (0.5 µM), or *E. coli* or calf thymus DNA (50 µg/ml) at 37° C. for 24 hr. (for IL-6 production) or 5 days (for IgM production). Concentrations of stimulants were chosen based on preliminary studies with titrations. In some cases, cells were treated with CpG O-ODN along with various concentrations (1-10 µg/ml) of neutralizing rat IgG1 antibody against murine IL-6 (hybridoma MP5-20F3) or control rat IgG1 mAb to *E. coli* β-galactosidase (hybridoma GL113; ATCC, Rockville, Md.) (20) for 5 days. At the end of incubation, culture supernatant fractions were analyzed by ELISA as below.

In vivo induction of IL-6 and IgM. BALB/c Mice were injected intravenously (iv) with PBS, calf thymus DNA (200 µg/100 µl PBS/mouse), *E. coli* DNA (200 µg/100 µl PBS/mouse), or CpG or non-CpG S-ODN (200 µg/100 µl PBS/mouse). Mice (two/group) were bled by retroorbital puncture and sacrificed by cervical dislocation at various time points. Liver, spleen, thymus, and bone marrow were removed and RNA was prepared from those organs using RNAzol B (Tel-Test, Friendswood, Tex.) according to the manufacturers protocol.

ELISA. Flat-bottomed Immun 1 plates (Dynatech Labbratories, Inc., Chantilly, Va.) were coated with 100 µl /well of anti-mouse IL-6 mAb (MP5-20F3) (2 µg/ml) or anti-mouse IgM µ-chain specific (5 µg/ml; Sigma, St. Louis, Mo.) in carbonate-bicarbonate, pH 9.6 buffer (15 nM $Na_2CO_3$, 35 mM $NaHCO_3$) overnight at 4° C. The plates were then washed with TPBS (0.5 mM $MgCl_2 \cdot 6H_2O$, 2.68 mM KCl, 1.47 mM $KH_2PO_4$, 0.14 M NaCl, 6.6 mM $K_2HPO_4$, 0.5% Tween 20) and blocked with 10% FCS in TPBS for 2 hr at room temperature and then washed again. Culture supernatants, mouse sera, recombinant mouse IL-6 (Pharmingen, San Diego, Calif.) or purified mouse IgM (Calbiochem, San Diego, Calif.) were appropriately diluted in 10% FCS and incubated in triplicate wells for 6 hr at room temperature. The plates were washed and 100 µl/well of biotinylated rat anti-mouse IL-6 monoclonal antibodies (MP5-32C11, Pharmingen, San Diego, Calif.) (1 µg/ml in 10% FCS) or biotinylated anti-mouse Ig (Sigma, St. Louis, Mo.) were added and incubated for 45 min. at room temperature following washes with TPBS. Horseradish peroxidase (HRP) conjugated avidin (Bio-rad Laboratories, Hercules, Calif.) at 1:4000 dilution In 10% FCS (100 µl/well) was added and incubated at room temperature for 30 min. The plates were washed and developed with o-phenylendiamine dihydrochloride (OPD; Sigma, St. Louis Mo.) 0.05 M phosphate-citrate buffer, pH 5.0, for 30 min. The reaction was stopped with 0.67 N $H_2SO_4$ and plates were read on a microplate reader (Cambridge Technology, Inc., Watertown, Mass.) at 490-600 nm. The results are shown in FIGS. 1 and 2.

Figure 3:
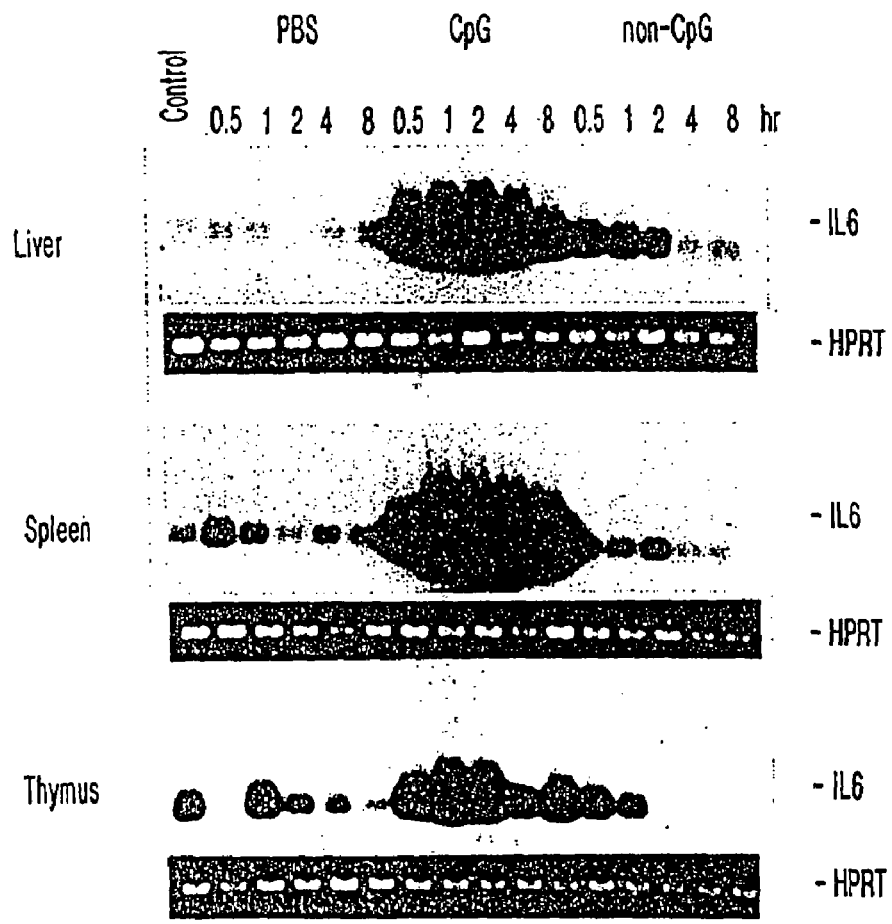
FIG. 3 is an autoradiograph showing IL-6 mRNA expression as determined by reverse transcription polymerase chain reaction in liver, spleen, and thymus at various time periods after in vivo stimulation of BALB/c mice (two mice/group) injected iv with 100 µl of PBS, 200 µg of CpG phosphorothioate ODN 5' TCCATGACGTTCCTGATGCT 3' (SEQ ID NO:7) or non-CpG phosphorothioate ODN 5' TCCAT-GAGCTTCCTGAGTCT 3' (SEQ ID NO:8).

RT-PCR. A sense primer, an antisense primer, and an internal oligonucleotide probe for IL-6 were synthesized using published sequences (Montgomery, R. A. and M. S. Dallman (1991), Analysis of cytokine gene expression during fetal thymic ontogeny using the polymerase chain reaction (*J. Immunol.*) 147:554). cDNA synthesis and IL-6 PCR was done essentially as described by Montgomery and Dallman (Montgomery, R. A. and M. S. Dallman (1991), Analysis of cytokine gene expression during fetal thymic ontogeny using the polymerase chain reaction (*J. Immunol.*) 147:554) using RT-PCR reagents from Perkin-Elmer Corp. (Hayward, Calif.). Samples were analyzed after 30 cycles of amplification by gel electrophoresis followed by unblot analysis (Stoye, J. P. et al., (1991) DNA hybridization in dried gels with fragmented probes: an improvement over blotting techniques, Techniques 3:123). Briefly, the gel was hybridized at room temperature for 30 min. in denaturation buffer (0.05 M NaOH, 1.5M NaCl) followed by incubation for 30 min. in renaturation buffer (1.5 M NaCl, 1 M Tris, pH 8) and a 30 min. wash in double distilled water. The gel was dried and prehybridized at 47° C. for 2 hr. hybridization buffer (5× SSPE, 0.1% SDS) containing 10 µg/ml denatured salmon sperm DNA. The gel was hybridized with $2 \times 10^6$ cpm/ml γ-[$^{32}$P]ATP end-labeled internal oligonucleotide probe for IL-6 (5'CATTTCCACGATTTCCCA3') SEQ ID NO:56) overnight at 47° C., washed 4 times (2×SSC, 0.2% SDS) at room temperature and autoradiographed. The results are shown in FIG. 3.

Cell Proliferation assay. DBA/2 mice spleen B cells ($5 \times 10^4$ cells/100 µl/well) were treated with media, CpG or non-CpG S-ODN (0.5 µM) or O-ODN (20 µM) for 24 hr at 37° C. Cells were pulsed for the last four hr. with either [$^3$H] Thymidine or [$^3$H] Uridine (1 µCi/well). Amounts of [$^3$H] incorporated were measured using Liquid Scintillation Analyzer (Packard Instrument Co., Downers Grove, Ill.).

Transfections and CAT assays. WEHI-231 cells ($10^7$ cells) were electroporated with 20 µg of control or human IL-6 promoter-CAT construct (kindly provided by S. Manolagas, Univ. of Arkansas) (Pottratz, S. T. et al., (1994) 17B-estradiol inhibits expression of human interleukin-6 promoter-reporter constructs by a receptor-dependent mechanism. *J. Clin. Invest.* 93:944) at 250 mV and 960 µF. Cells were stimulated with various concentrations or CpG or non-CpG ODN after electroporation. Chloramphenicol acetyltransferase (CAT) activity was measured by a solution assay (Seed, B. and J. Y. Sheen (1988) A single phase-extraction assay for chloramphenicol acetyl transferase activity. *Gene* 76:271) 16 hr. after transfection. The results are presented in FIG. 5.

Example 10

Oligodeoxynucleotide Modifications Determine the Magnitude of B Cell Stimulation by CpG Motifs ODN were synthesized on an Applied Biosystems Inc. (Foster City, Calif.) model 380A, 380B, or 394 DNA synthesizer using standard procedures (Beacage and Caruthers (1981) Deoxynucleoside phosphoramidites—A new class of key intermediates for deoxypolynucleotide synthesis. Tetrahedron Letters 22, 1859-1862.). Phosphodiester ODN were synthesized using standard beta-cyanoethyl phosphoramidite chemistry. Phosphorothioate linkages were introduced by oxidizing the phosphite linkage with elemental sulfur instead of the standard iodine oxidation. The four common nucleoside phosphoramidites were purchased from Applied Biosystems. All phosphodiester and thioate containing ODN were deprotected by treatment with concentrated ammonia at 55° C. for 12 hours. The ODN were purified by gel exclusion chromatography and lyophilized to dryness prior to use. Phosphorodithioate linkages were introduced by using deoxynucleoside S-(b-benzoylmercaptoethyl) pyrrolidino thiophosphoramidites (Wiesler, W. T. et al., (1993) In Methods in Molecular Biology: Protocols for Oligonucleotides and Analogs-Synthesis and Properties, Agrawal, S. (ed.), Humana Press, 191-206.). Dithioate containing ODN were deprotected by treatment with concentrated ammonia at 55° C. for 12 hours followed by reverse phase HPLC purification.

In order to synthesize oligomers containing methylphosphonothioates or methylphosphonates as well as phosphodiesters at any desired internucleotide linkage, two different synthetic cycles were used. The major synthetic differences in the two cycles are the coupling reagent where dialkylaminomethylnucleoside phosphines are used and the oxidation reagents in the case of methylphosphonothioates. In order to synthesize either derivative, the condensation time has been increased for the dialkylaminomethylnucleoside phosphines due to the slower kinetics of coupling (Jager and Engels, (1984) Synthesis of deoxynucleoside methylphosphonates via a phosphonamidite approach. Tetrahedron Letters 24, 1437-1440). After the coupling step has been completed, the methylphosphinodiester is treated with the sulfurizing reagent (5% elemental sulfur, 100 millimolar N,N-diamethylaminopyridine in carbon disulfide/pyridine/triethylamine), four consecutive times for 450 seconds each to produce methylphosphonothioates. To produce methylphosphonate linkages, the methylphosphinodiester is treated with standard oxidizing reagent (0.1 M iodine in tetrahydrofuran/2,6-lutidine/water).

The silica gel bound oligomer was treated with distilled pyridine/concentrated ammonia, 1:1, (v/v) for four days at 4 degrees centigrade. The supernatant was dried in vacuo, dissolved in water and chromatographed on a G50/50 Sephadex column.

As used herein, O-ODN refers to ODN which are phosphodiester; S-ODN are completely phosphorothioate modified; S-O-ODN are chimeric ODN in which the central linkages are phosphodiester, but the two 5' and five 3' linkages are phosphorothioate modified; $S_2$-O-ODN are chimeric ODN in which the central linkages are phosphodiester, but the two 5' and five 3' linkages are phosphorodithioate modified; and MP-O-ODN are chimeric ODN in which the central linkages are phosphodiester, but the two 5' and five 3' linkages are methylphosphonate modified. The ODN sequences studied (with CpG dinucleotides indicated by underlining) include:

```
3D   (5' GAGAACGCTGGACCTTCCAT),   (SEQ ID NO:14);

3M   (5' TCCATGTCGGTCCTGATGCT),   (SEQ ID NO:22);

5    (5' GGCGTTATTCCTGACTCGCC),   (SEQ ID NO:57);

and 6    (5' CCTACGTTGTATGCGCCCAGCT), (SEQ ID NO:58).
```

These sequences are representative of literally hundreds of CpG and non-CpG ODN that have been tested in the course of these studies.

Mice. DBA/2, or BXSB mice obtained from The Jackson Laboratory (Bar Harbor, Me.), and maintained under specific pathogen-free conditions were used as a source of lymphocytes at 5-10 wk of age with essentially identical results.

Cell proliferation assay. For cell proliferation assays, mouse spleen cells ($5 \times 10^4$ cells/100 µl/well) were cultured at 37° C. in a 5% $CO_2$ humidified incubator in RPMI-1640 supplemented with 10% (v/v) heat inactivated fetal calf serum heated to 65° C. for experiments using O-ODN, or 56° C. for experiments using only modified ODN), 1.5 µM L-glutamine, 50 µM 2-mercaptoethanol, 100 U/ml penicillin and 100 µg/ml streptomycin for 24 hr or 48 hr as indicated. 1 µCi of $^3H$ uridine or thymidine (as indicated) was added to each well, and the cells harvested after an additional 4 hours of culture. Filters were counted by scintillation counting. Standard deviations of the triplicate wells were <5%. The results are presented in FIGS. 6-8.

Example 11

Induction of NK Activity

Phosphodiester ODN were purchased from Operon Technologies (Alameda, Calif.). Phosphorothioate ODN were purchased from the DNA core facility, University of Iowa, or from The Midland Certified Reagent Company (Midland Tex.). E.coli (strain B) DNA and calf thymus DNA were purchased from Sigma (St. Louis, Mo.). All DNA and ODN were purified by extraction with phenol:chloroform:isoamyl alcohol (25:24:1) and/or ethanol precipitation. The LPS level in ODN was less than 12.5 ng/mg and E.coli and calf thymus DNA contained less than 2.5 ng of LPS/mg of DNA by Limulus assay.

Virus-free, 4-6 week old, DBA/2, C57BL/6 (B6) and congenitally athymic BALB/C mice were obtained on contract through the Veterans Affairs from the National Cancer Institute (Bethesda, Md.). C57BL/6 SCID mice were bred in the SPF barrier facility at the University of Iowa Animal Care Unit.

Human peripheral mononuclear blood leukocytes (PBMC) were obtained as previously described (Ballas, Z. K; et al., (1990) *J. Allergy Clin. Immunol.* 85:453; Ballas, Z. K. and W. Rasmussen (1990) *J. Immunol.* 145:1039; Ballas, Z. K. and W. Rasmussen (1993) *J. Immunol.* 150:17). Human or murine cells were cultured at $5 \times 10^6$/well, at 37° C. in a 5% $CO_2$ humidified atmosphere in 24-well plates (Ballas, Z. K. et al., (1990) *J. Allergy Clin. Immunol.* 85:453; Ballas, Z. K. and W. Rasmussen (1990) *J. Immunol* 145:1039; and Ballas, Z. K. and W. Rasmussen (1993) *J. Immunol*, 150:17), with medium alone or with CpG or non-CpG ODN at the indicated concentrations, or with E.coli or calf thymus (50 µg/ml) at 37° C. for 24 hr. All cultures were harvested at 18 hr. and the cells were used as effectors in a standard 4 hr. $^{51}Cr$-release assay against K562 (human) or YAC-1 (mouse) target cells as previously described. For calculation of lytic units (LU), 1 LU was defined as the number of cells needed to effect 30% specific lysis. Where indicated, neutralizing antibodies against IFN-β (Lee Biomolecular, San Diego, Calif.) or IL-12 (C15.1, C15.6, C17.8, and C17.15; provided by Dr. Giorgio Trinchieri, The Wistar Institute, Philadelphia, Pa.) or their isotype controls were added at the initiation of cultures to a concentration of 10 µg/ml. For anti-IL-12 addition, 10 µg of each of the 4 MAB (or isotype controls) were added simultaneously. Recombinant human IL-2 was used at a concentration of 100 U/ml.

Example 12

Prevention of the Development of an Inflammatory Cellular Infiltrate and Eosinophilia in a Murine Model of Asthma 6-8 week old C56BL/6 mice (from The Jackson Laboratory, Bar Harbor, Me.) were immunized with 5,000 *Schistosoma mansoni* eggs by intraperitoneal (i.p.) injection on days 0 and 7. *Schistosoma mansoni* eggs contain an antigen (*Schistosoma mansoni* egg antigen (SEA)) that induces a Th2 immune response (e.g. production of IgE antibody). IgE antibody production is known to be an important cause of asthma.

The immunized mice were then treated with oligonucleotides (30 µg in 200 µl saline by i.p.injection), which either contained an unmethylated CpG motif (i.e. TCCATGACGTTCCTGACGTT; SEQ D NO.10) or did not (i.e. control, TCCATGAGCTTCCTGAGTCT; SEQ ID NO.11). Soluble SEA (10 µg in 25 µl of saline) was administered by intranasal instillation on days 14 and 21. Saline was used as a control.

Mice were sacrificed at various times after airway challenge. Whole lung lavage was performed to harvest airway and alveolar inflammatory cells. Cytokine levels were measured from lavage fluid by ELISA. RNA was isolated from whole lung for Northern analysis and RT-PCR studies using CsCl gradients. Lungs were inflated and perfused with 4% paraformaldehyde for histologic examination.

Figure 9:
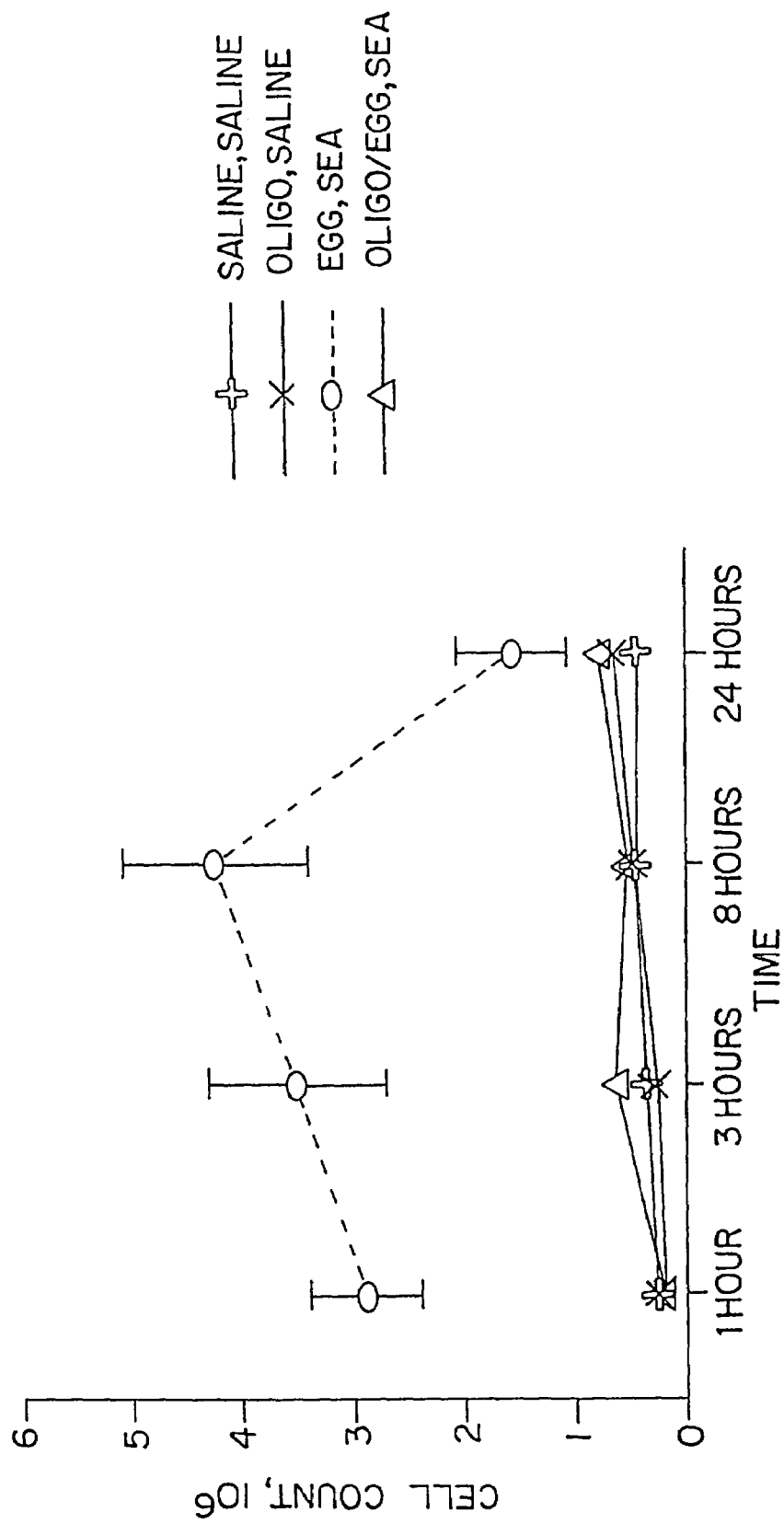
FIG. 9 is a graph plotting lung lavage cell count over time. The graph shows that when the mice are initially injected with Schistosoma mansoni eggs "egg", which induces a Th2 immune response, and subsequently inhale Schistosoma mansoni egg antigen "SEA" (open circle), many inflammatory cells are present in the lungs. However, when the mice are initially given CpG oligo (SEQ ID NO:10) along with egg, the inflammatory cells in the lung are not increased by subsequent inhalation of SEA (open triangles).

FIG. 9 shows that when the mice are initially injected with the eggs i.p., and then inhale the egg antigen (open circle), many inflammatory cells are present in the lungs. However, when the mice are initially given a nucleic acid containing an unmethylated CpG motif along with the eggs, the inflammatory cells in the lung are not increased by subsequent inhalation of the egg antigen (open triangles).

Figure 10:
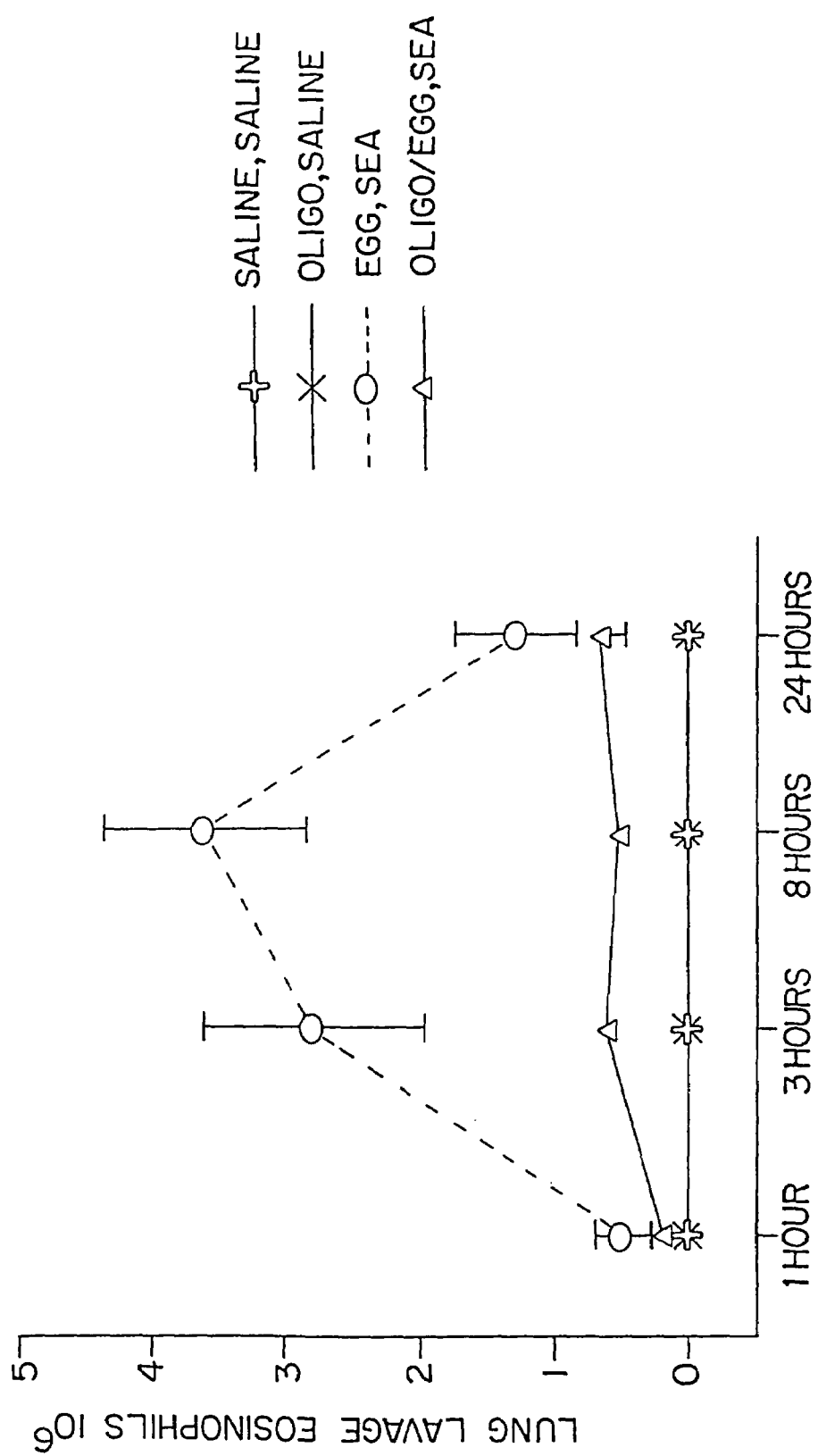
FIG 10 is a graph plotting lung lavage eosinophil count over time. Again, the graph shows that when the mice are initially injected with egg and subsequently inhale SEA (open circle), many eosinophils are present in the lungs. However, when the mice are initially given CpG oligo (SEQ ID NO:10) along with egg, the inflammatory cells in the lung are not increased by subsequent inhalation of the SEA (open triangles).

FIG. 10 shows that the same results are obtained when only eosinophils present in the lung lavage are measured. Eosinophils are the type of inflammatory cell most closely associated with asthma.

Figure 11:
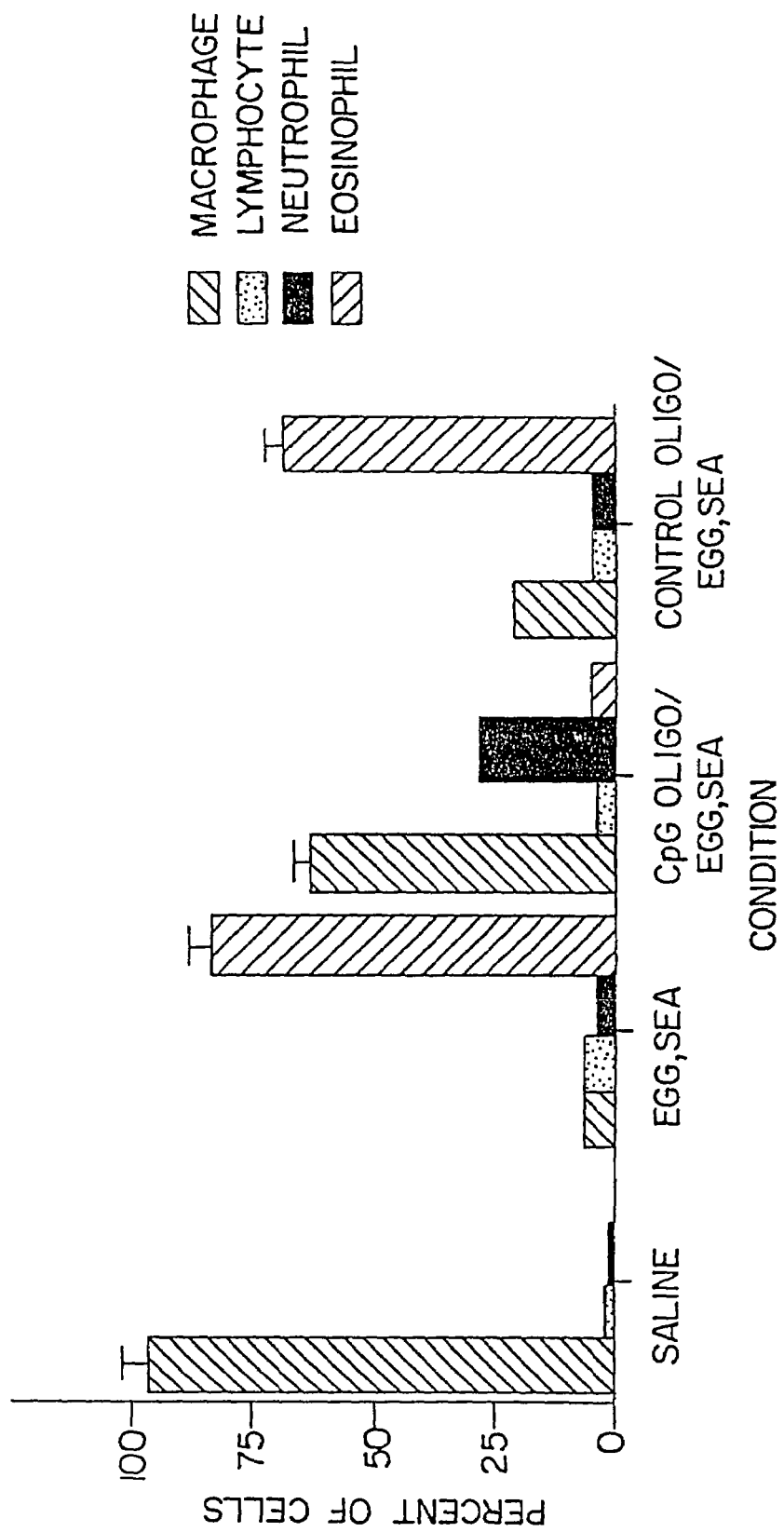
FIG. 11 is a bar graph plotting the effect on the percentage of macrophage, lymphocyte, neutrophil and eosinophil cells induced by exposure to saline alone; egg, then SEA; egg and SEQ ID NO:11, then SEA; and egg and control oligo (SEQ ID NO:11), then SEA. When the mice are treated with the control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

FIG. 11 shows that when the mice are treated with a control oligo at the time of the initial exposure to the egg, there is little effect on the subsequent influx of eosinophils into the lungs after inhalation of SEA. Thus, when mice inhale the eggs on days 14 or 21, they develop an acute inflammatory response in the lungs. However, giving a CpG oligo along with the eggs at the time of initial antigen exposure on days 0 and 7 almost completely abolishes the increase in eosinophils when the mice inhale the egg antigen on day 14.

Figure 12:
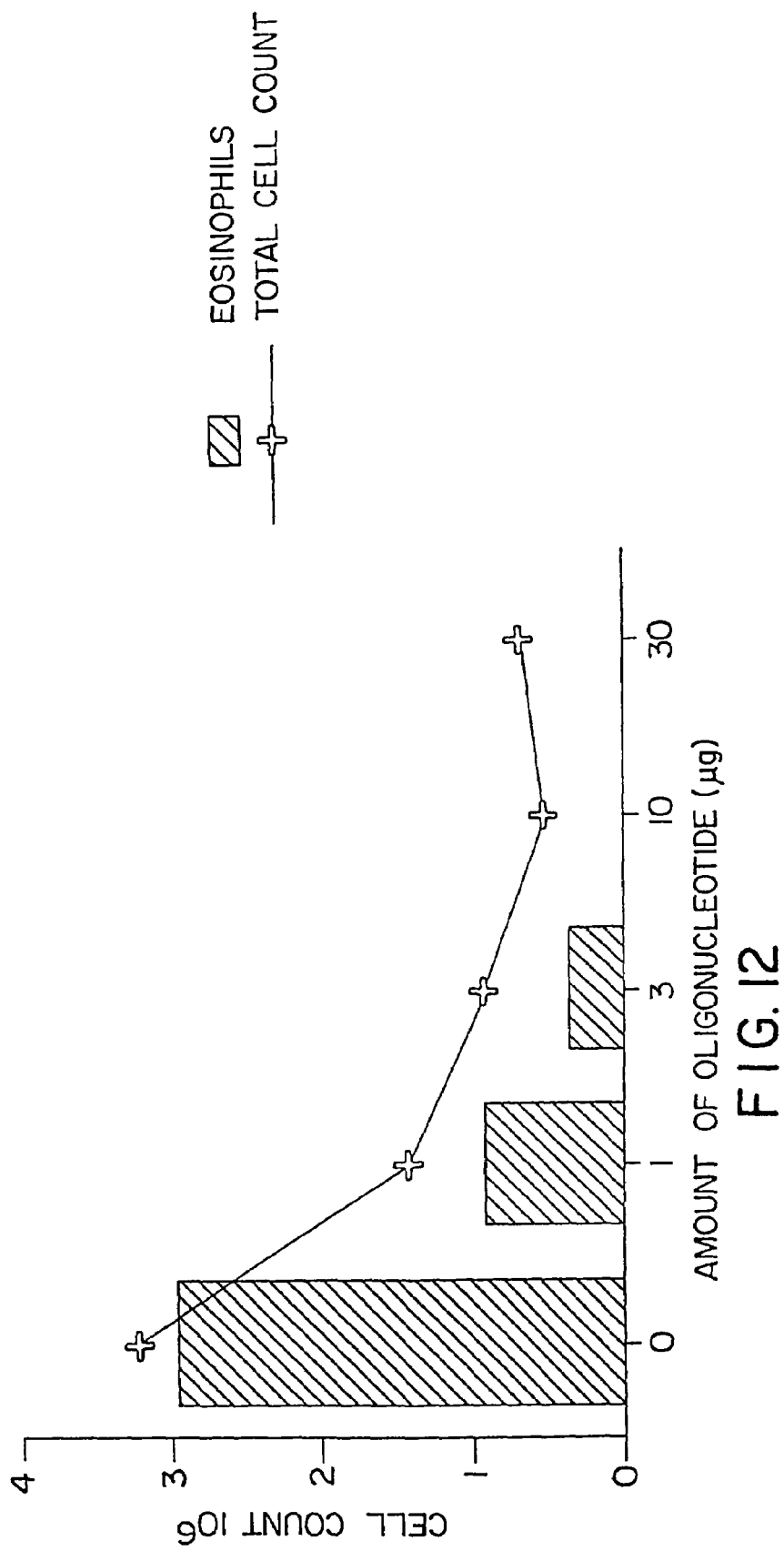
FIG. 12 is a bar graph plotting eosinophil count in response to injection of various amounts of the protective oligo SEQ ID NO:10.

FIG. 12 shows that very low doses of oligonucleotide (<1 µg) can give this protection.

Figure 13:
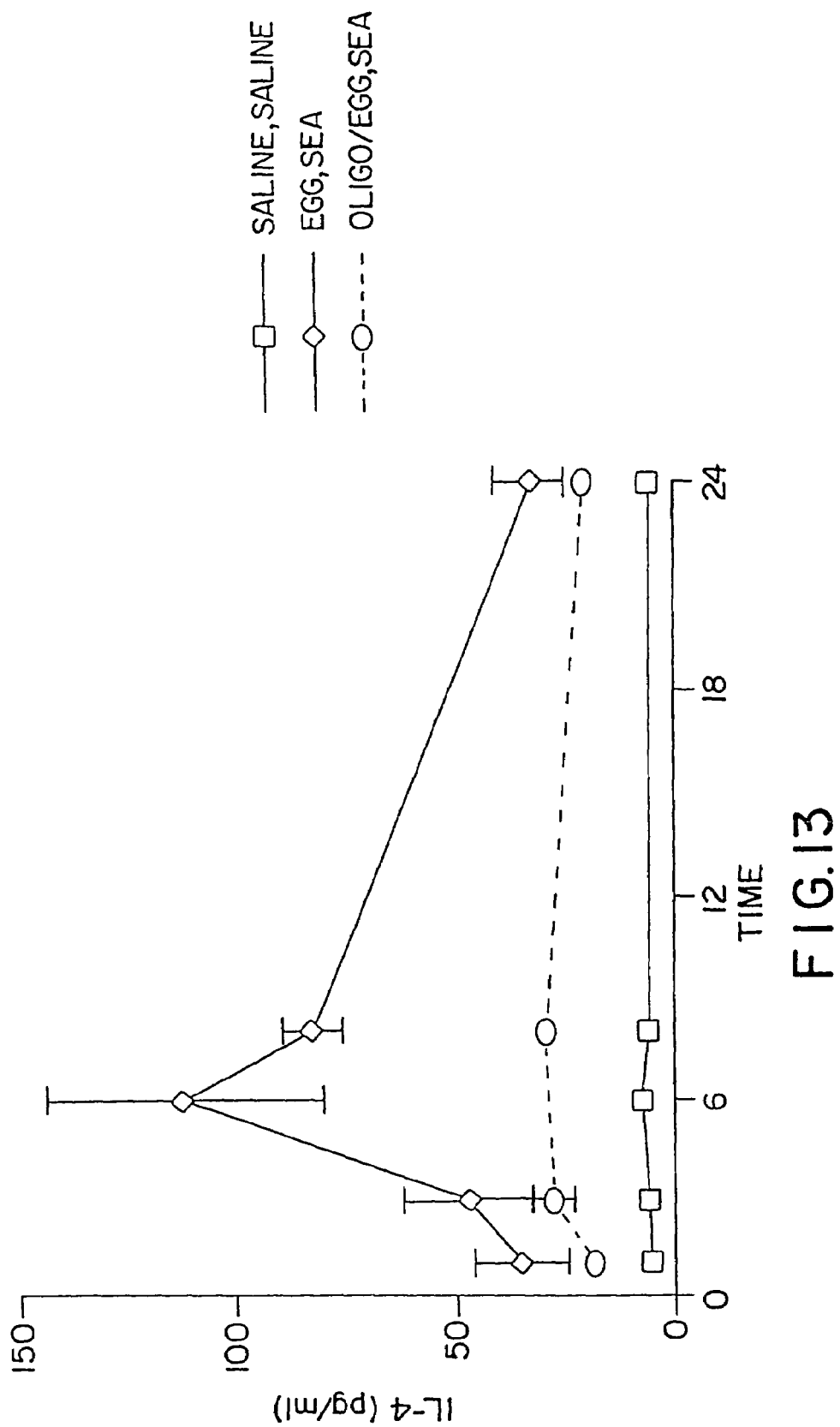
FIG. 13 is a graph plotting interleukin 4 (IL-4) production (pg/ml) in mice over time in response to injection of egg, then SEA (open diamond); egg and SEQ ID NO:10, then SEA (open circle); or saline, then saline (open square). The graph shows that the resultant inflammatory response correlates with the levels of the Th2 cytokine IL4 in the lung.

FIG. 13 shows that the resultant inflammatory response correlates with the levels of the Th2 cytokine IL-4 in the lung.

Figure 14:
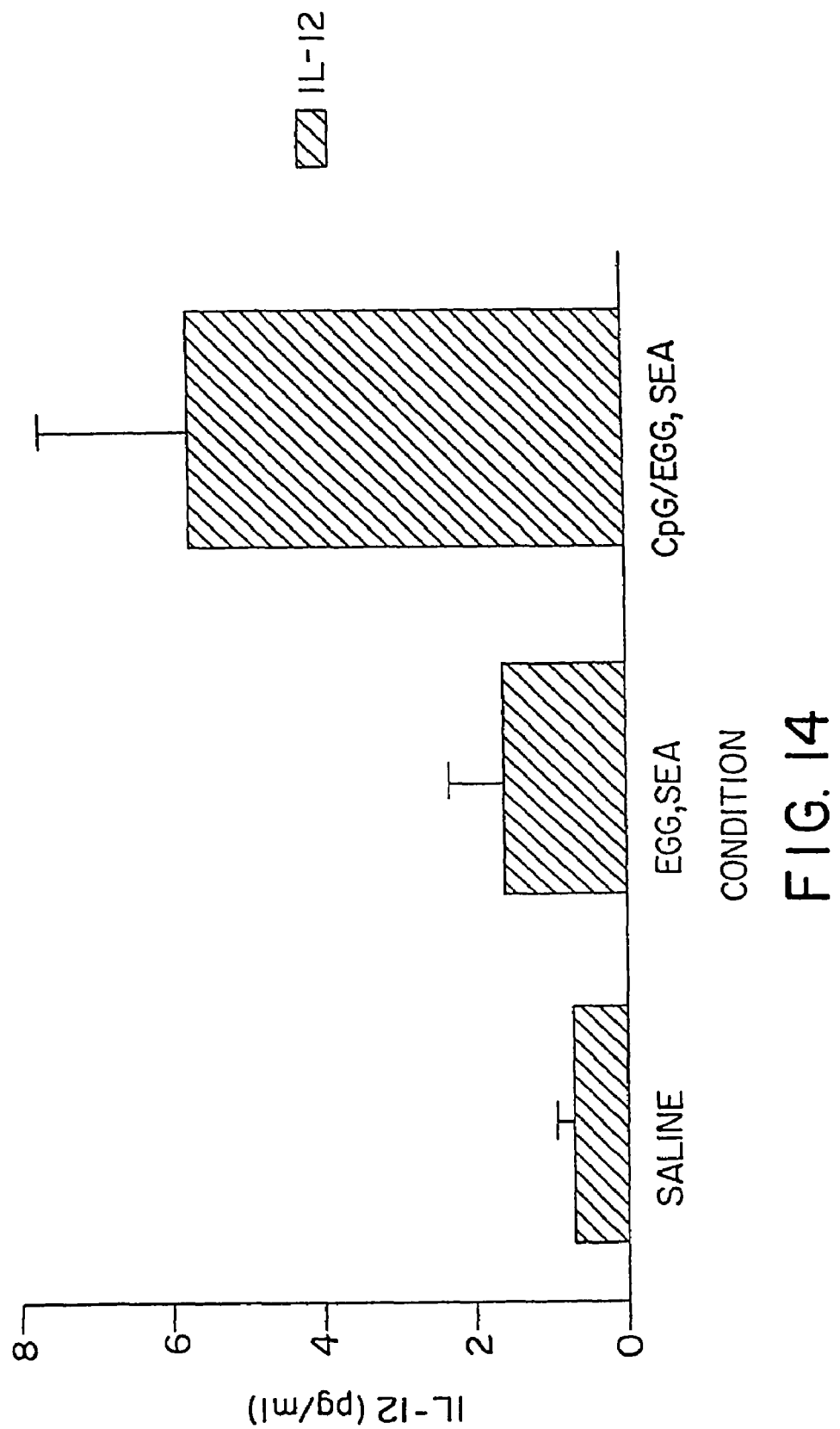
FIG. 14 is a bar graph plotting interleukin 12 (IL-12) production (pg/ml) in mice overtime in response to injection of saline; egg, the SEA; or SEQ ID NO:10 and egg, then SEA. The graph shows that administration of an oligonucleotide containing an unmethylated CpG motif can actually redirect the cytokine response of the lung to production of IL-12, indicating a Th1 type of immune response.

FIG. 14 shows that administration of an oligonucleotide containing an unmethylated CpG motif can actually redirect the cytokine response of the lung to production of Il-12, indicating a Th1 type of immune response.

Figure 15:
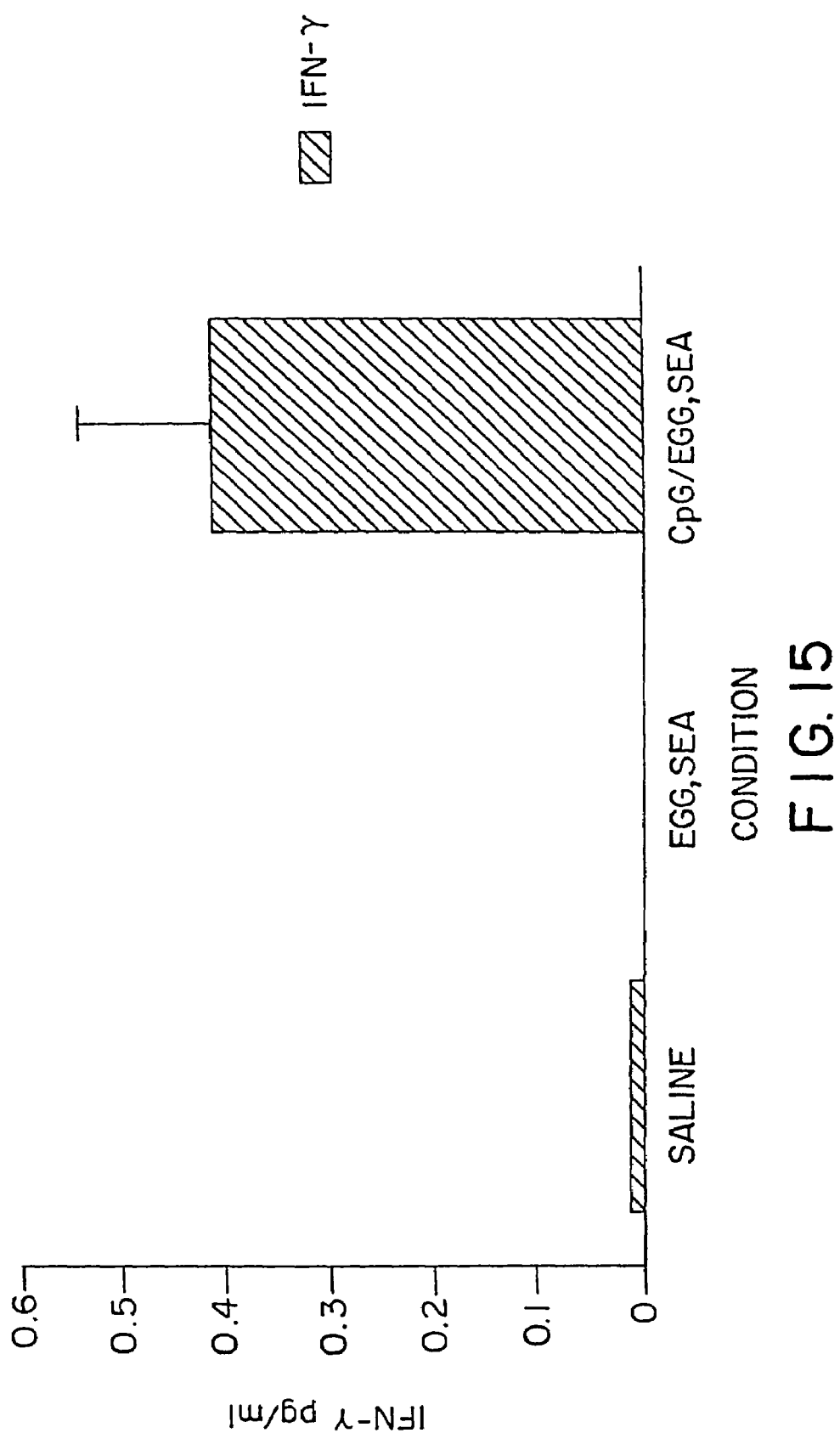
FIG. 15 is a bar graph plotting interferon gamma (IFN-γ) production (pg/ml) in mice over time in response to injection of saline; egg, then saline; or SEQ ID NO:10 and egg, then SEA. The graph shows that administration of an oligonucleotide containing an unmethylated CpG motif can also redirect the cytokine response of the lung to production of IFN-γ, indicating a Th1 type of immune response.

FIG. 15 shows that administration of an oligonucleotide containing an unmethylated CpG motif can also redirect the cytokine response of the lung to production of IFN-γ, indicating a Th1 type of immune response.

Example 13

CpG Oligonucleotides Induce Human PBMC to Secrete Cytokines

Human PBMC were prepared from whole blood by standard centrifugation over ficoll hypaque. Cells ($5\times10^5$/ml) were cultured in 10% autologous serum in 96 well microtiter plates with CpG or control oligodeoxynucleotides (24 µg/ml for phosphodiester oligonucleotides; 6 µg/ml for nuclease resistant phosphorothioate oligonucleotides) for 4 hr in the case of TNF-α or 24 hr. for the other cytokines before supernatant harvest and assay, measured by ELISA using Quantikine lits or reagents from R&D Systems (pg/ml) or cytokine ELISA kits from Biosource (for IL-12 assay). Assays were performed as per the manufacturer's instructions. Data are presented in Table 6 as the level of cytokine above that in wells with no added Oligodeoxynucleotide.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method of decreasing IgE in a subject who has been exposed to an allergen comprising administering to the subject an immunostimulatory oligonucleotide/delivery complex, said delivery complex comprising an oligonucleotide linked to a biodegradable delivery complex, wherein the oligonucleotide comprises the sequence 5'-C, G-3', wherein the immunostimulatory oligonucleotide is 8 to 40 nucleotides in length and comprises: 5' $X_1X_2CGX_3X_4$ 3', wherein C and G are unmethylated and $X_1$, $X_2$, $X_3$, and $X_4$ are nucleotides, in an amount sufficient to decrease IgE in the subject, wherein the decrease in IgE is relative to that observed in the subject who has been exposed to an allergen but is not treated with an immunostimulatory oligonucleotide/delivery complex.

2. The method of claim 1, wherein said complex is antigen-free.

3. The method of claim 1, wherein said complex further comprises an antigen.

4. The method of claim 1, wherein said delivery complex is a liquid phase microcarrier.

5. The method of claim 1, wherein said immunostimulatory oligonucleotide is covalently linked to said delivery complex.

6. The method of claim 1, wherein said immunostimulatory oligonucleotide is non-covalently linked to said delivery complex.

7. The method of claim 1, wherein said immunostimulatory oligonucleotide comprises a phosphate backbone modification.

8. The method of claim 7, wherein said phosphate backbone modification is a phosphorothioate.

9. The method of claim 1, wherein the immunostimulatory oligonucleotide does not include a GCG trinucleotide at a 5' and/or 3' terminal.

10. The method of claim 1 wherein the immunostimulatory oligonucleotide does not contain a $5'X_1X_2CGX_3X_4 3'$ palindrome.

11. The method of claim 1, wherein said oligonucleotide comprises the sequence 5'-T, C, G-3'.

12. The method of claim 1, wherein the individual has a viral infection.

* * * * *

SEQUENCE LISTING

```
<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
atggaaggtc cagtgttctc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
atcgacctac gtgcgttctc                                              20

<210> SEQ ID NO 3
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 3
tccataacgt tcctgatgct                                                    20

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 4
gctagatgtt agcgt                                                         15

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
gagaacgtcg accttcgat                                                     19

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
gcatgacgtt gagct                                                         15

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tccatgacgt tcctgatgct                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
tccatgagct tcctgagtct                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tccaagacgt tcctgatgct                                                    20
```

-continued

```
<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tccatgacgt tcctgacgtt                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
tccatgagct tcctgagtgc t                                                 21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ggggtcaacg ttgagggggg                                                   20

<210> SEQ ID NO 13
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 13
gctagacgtt agcgt                                                        15

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)...(7)
<223> OTHER INFORMATION: m5c

<400> SEQUENCE: 14
gctagacgtt agcgt                                                        15

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)...(7)
<223> OTHER INFORMATION: m5c
<220> FEATURE:
<221> NAME/KEY: modified_base
<222> LOCATION: (13)...(13)
```

```
<223> OTHER INFORMATION: m5c

<400> SEQUENCE: 15
gctagacgtt agcgt                                                      15

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 16
gcatgacgtt gagct                                                      15

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
atggaaggtc cagcgttctc                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
atcgactctc gagcgttctc                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 19
atcgactctc gagcgttctc                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)...(3)
<223> OTHER INFORMATION: m5c

<400> SEQUENCE: 20
```

```
atcgactctc gagcgttctc                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)...(18)
<223> OTHER INFORMATION: m5c

<400> SEQUENCE: 21
atcgactctc gagcgttctc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
atggaaggtc caacgttctc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gagaacgctg gaccttccat                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gagaacgctc gaccttccat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gagaacgctc gaccttcgat                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gagcaagctg gaccttccat                                              20
```

```
<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)...(6)
<223> OTHER INFORMATION: m5c

<400> SEQUENCE: 27
gagaacgctg gaccttccat                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (14)...(14)
<223> OTHER INFORMATION: m5c

<400> SEQUENCE: 28
gagaacgctg gaccttccat                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gagaacgatg gaccttccat                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gagaacgctc cagcactgat                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
tccatgtcgg tcctgatgct                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tccatgctgg tcctgatgct                                          20
```

```
<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)...(8)
<223> OTHER INFORMATION: m5c

<400> SEQUENCE: 33
tccatgtcgg tcctgatgct                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (12)...(12)
<223> OTHER INFORMATION: m5c

<400> SEQUENCE: 34
tccatgtcgg tcctgatgct                                             20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
tccatgacgt tcctgatgct                                             20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
tccatgtcgg tcctgctgat                                             20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
tccatgtcgg tcctgatgct                                             20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
```
tccatgccgg tcctgatgct 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tccatggcgg tcctgatgct 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tccatgacgg tcctgatgct 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
tccatgtcga tcctgatgct 20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tccatgtcgc tcctgatgct 20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
tccatgtcgt tcctgatgct 20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
tccatgacgt tcctgatgct 20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
tccataacgt tcctgatgct                     20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
tccatgacgt ccctgatgct                     20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tccatcacgt gcctgatgct                     20

<210> SEQ ID NO 48
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 48
gcatgacgtt gagct                          15

<210> SEQ ID NO 49
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 49
gctagatgtt agcgt                          15

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggggtcaagt ctgaggggggg                    20

<210> SEQ ID NO 51
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 51
gctagacgtt agtgt                          15

```
<210> SEQ ID NO 52
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)...(8)
<223> OTHER INFORMATION: m5c

<400> SEQUENCE: 52
gctagacctt agtgt                                                    15

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)...(8)
<223> OTHER INFORMATION: m5c

<400> SEQUENCE: 53
tccatgtcgt tcctgatgct                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
tccatgacgt tcctgatgct                                               20

<210> SEQ ID NO 55
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 55
tctcccagcg tgcgccat                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 56
catttccacg atttccca                                                 18
```